(12) United States Patent
Kakadiaris et al.

(10) Patent No.: US 9,965,592 B2
(45) Date of Patent: May 8, 2018

(54) METHODS OF COMPUTING PERICARDIAL AND ABDOMINAL FAT AND METHODS FOR MOTION COMPENSATION

(71) Applicant: The University of Houston System, Houston, TX (US)

(72) Inventors: Ioannis A. Kakadiaris, Houston, TX (US); Morteza Naghavi, Houston, TX (US)

(73) Assignee: THE UNIVERSITY of HOUSTON SYSTEM, Houston, TX (US)

( * ) Notice: Subject to any disclaimer, the term of this patent is extended or adjusted under 35 U.S.C. 154(b) by 0 days. days.

(21) Appl. No.: 14/444,445

(22) Filed: Jul. 28, 2014

(65) Prior Publication Data
US 2017/0337343 A1    Nov. 23, 2017

Related U.S. Application Data

(62) Division of application No. 12/084,757, filed on Jul. 16, 2010.

(51) Int. Cl.
*G06K 9/00*    (2006.01)
*G06F 19/00*    (2018.01)

(52) U.S. Cl.
CPC ........ *G06F 19/3437* (2013.01); *G06F 19/345* (2013.01); *G06F 19/3431* (2013.01)

(58) Field of Classification Search
None
See application file for complete search history.

(56) References Cited

U.S. PATENT DOCUMENTS

2009/0010516 A1 *   1/2009   Boese ................... A61B 90/36
                                                                    382/131

* cited by examiner

*Primary Examiner* — Atiba O Fitzpatrick
(74) *Attorney, Agent, or Firm* — Robert W. Strozier

(57) ABSTRACT

A new cardiac risk factors are disclosed along with method for deriving the components of the factors, for developing the factors and for using the factors. Methods for computing pericardial fat and abdominal fat are also disclosed as well as methods for motion compensation.

6 Claims, 48 Drawing Sheets

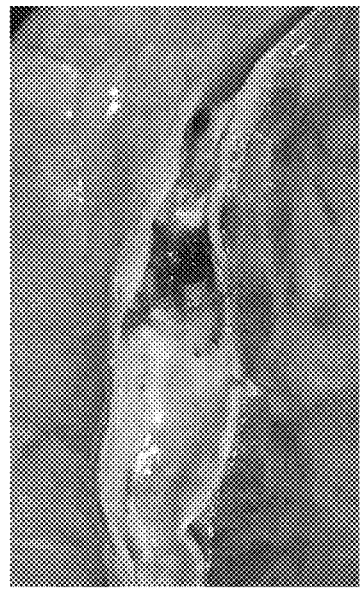
FIG. 7
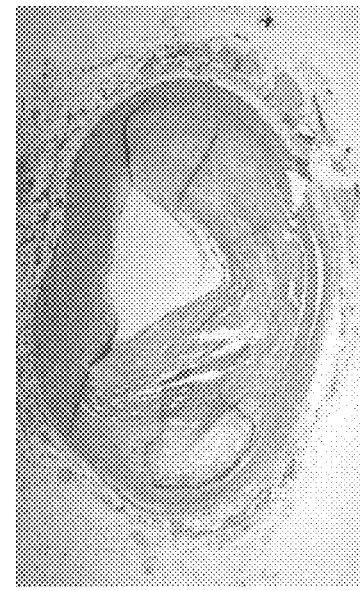
FIG. 8
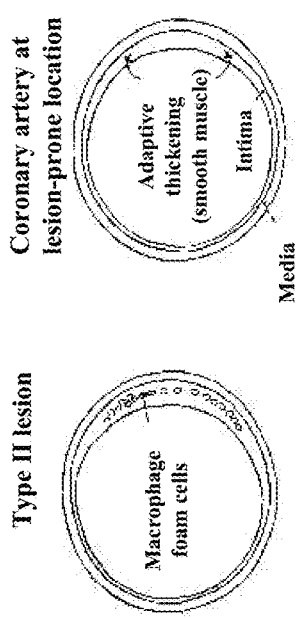
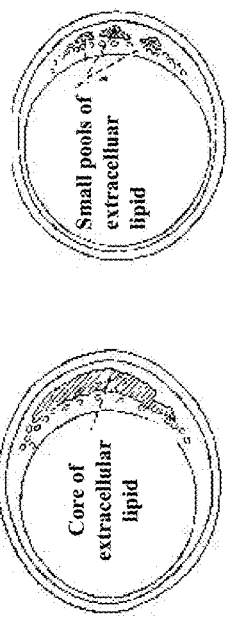
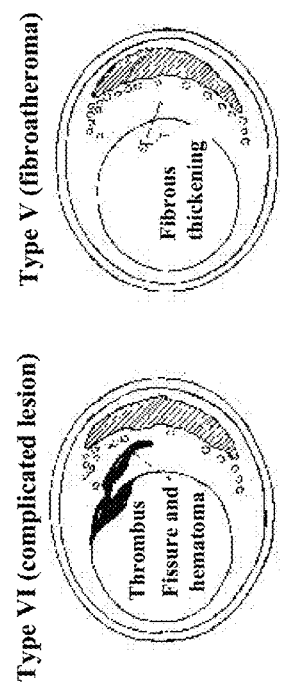
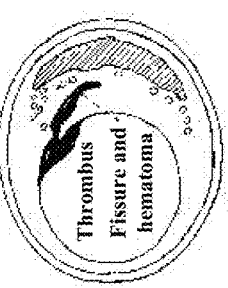
FIG. 9A-E

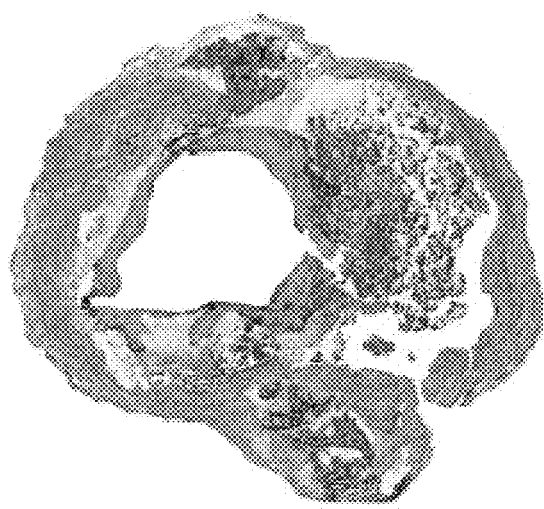
FIG. 11
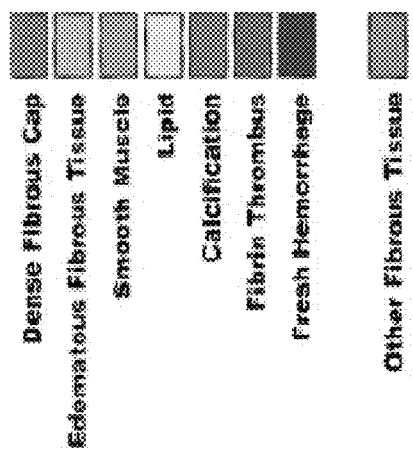
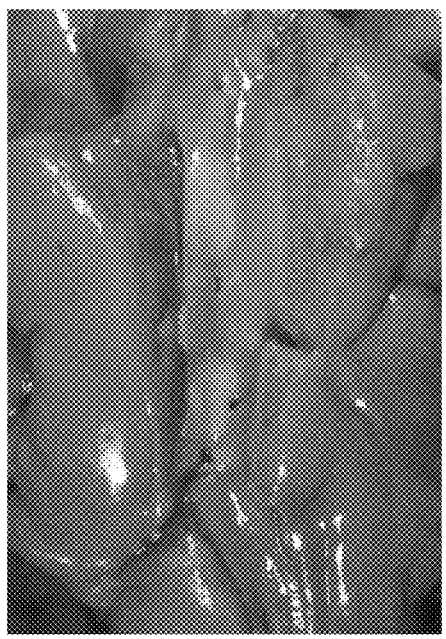
FIG. 10

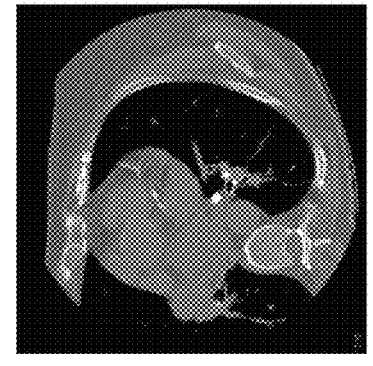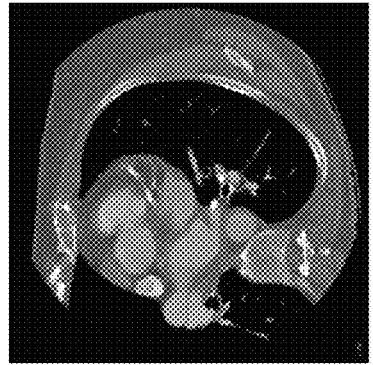
FIG. 18A  FIG. 18B  FIG. 18C  FIG. 18D
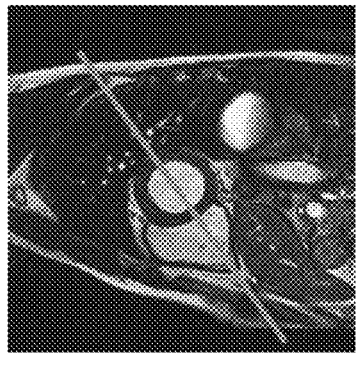
FIG. 22
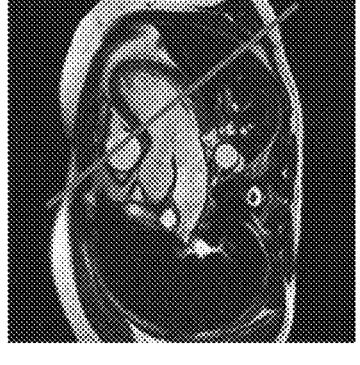
FIG. 21
FIG. 20
FIG. 19

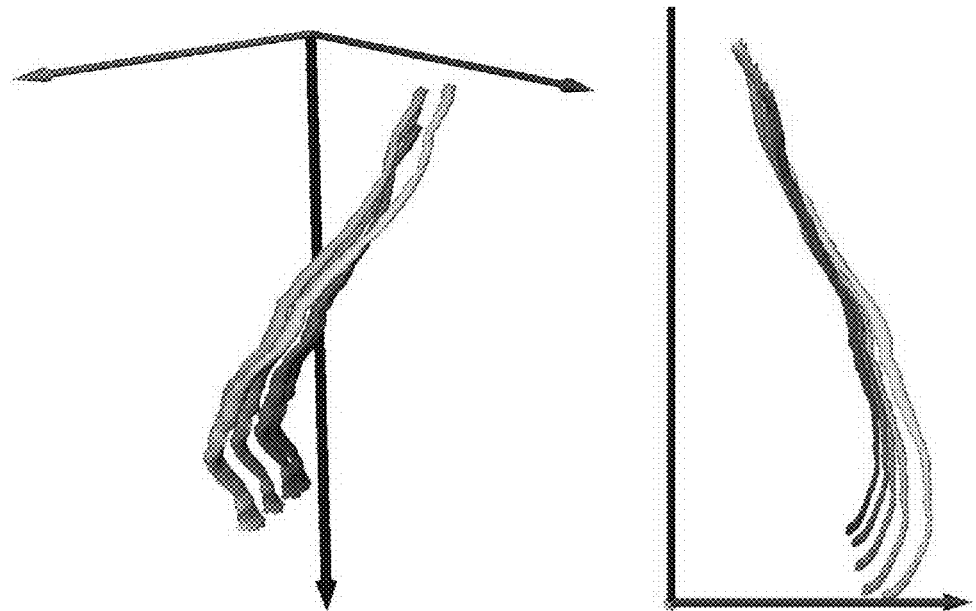
FIG. 33H  FIG. 33I
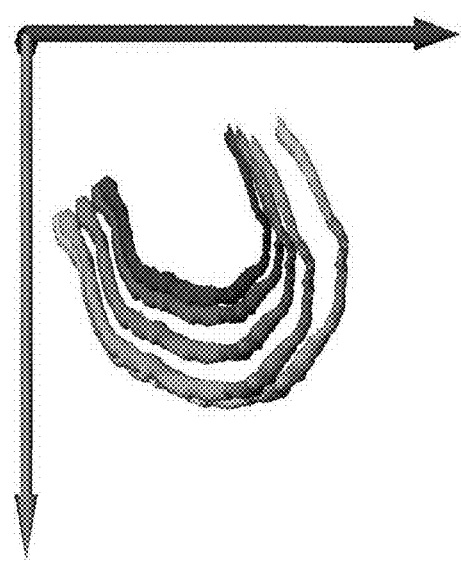
FIG. 33J

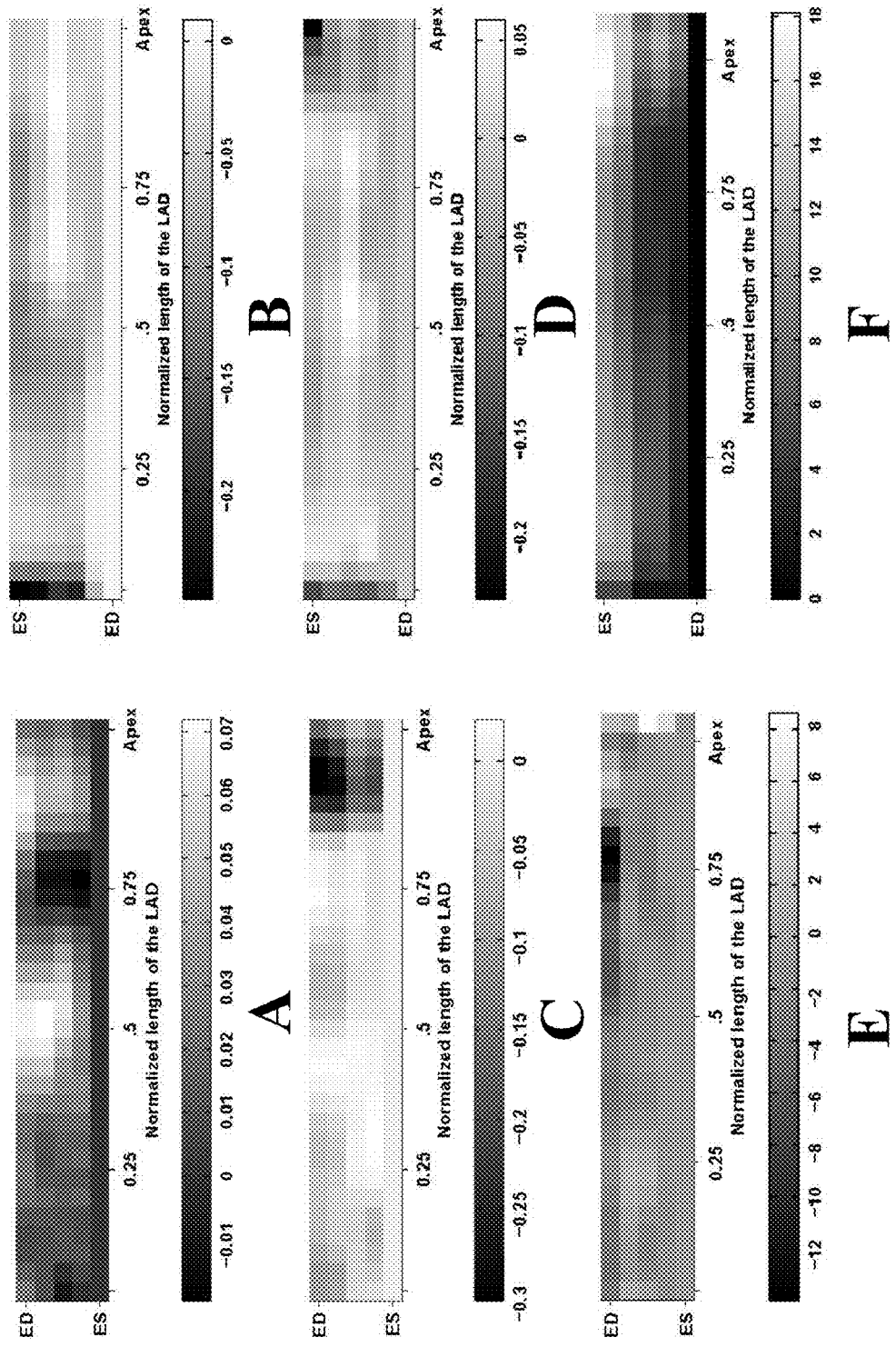
FIG. 36A-F

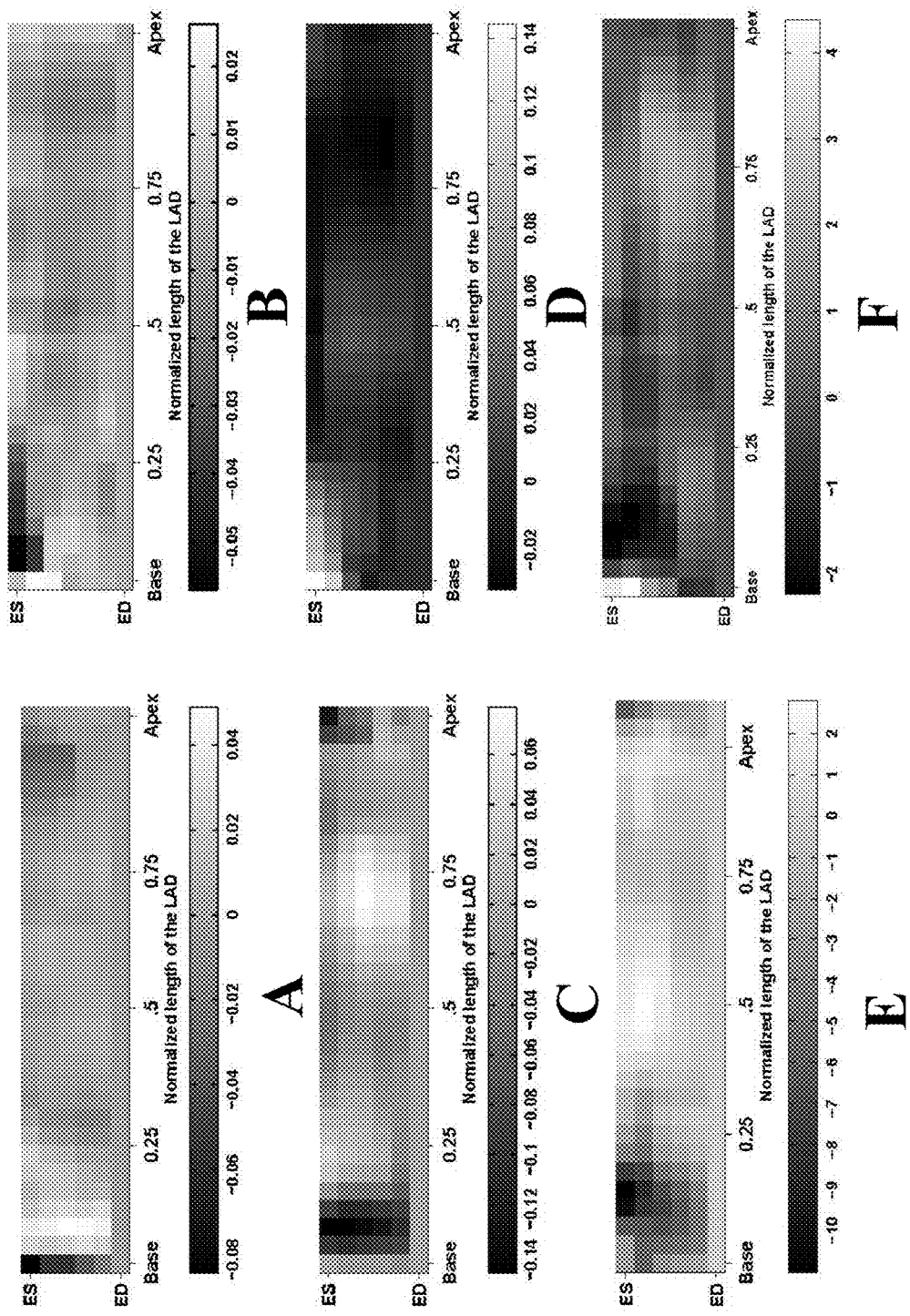
FIG. 37A-F

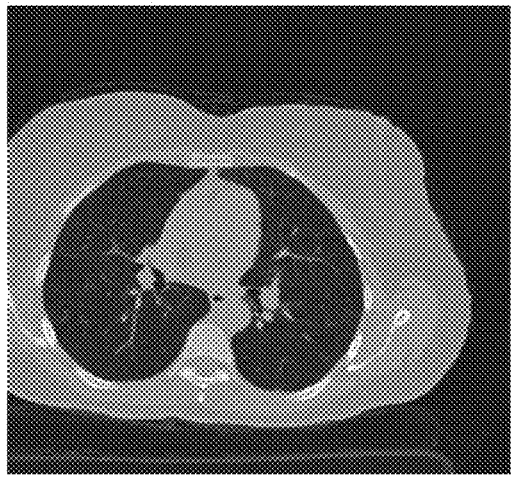
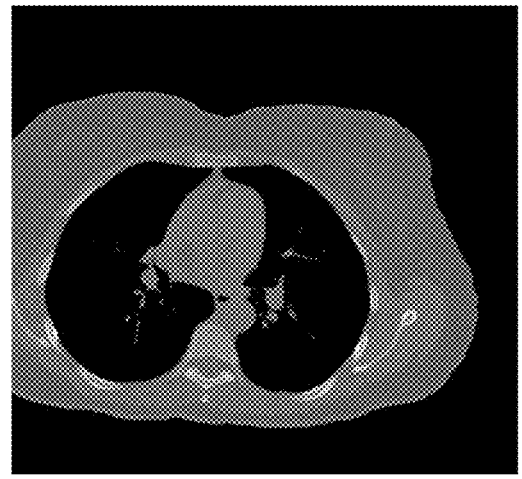
FIG. 38A  FIG. 38B
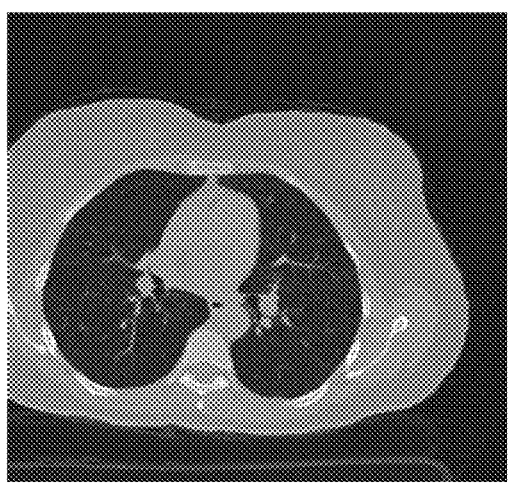
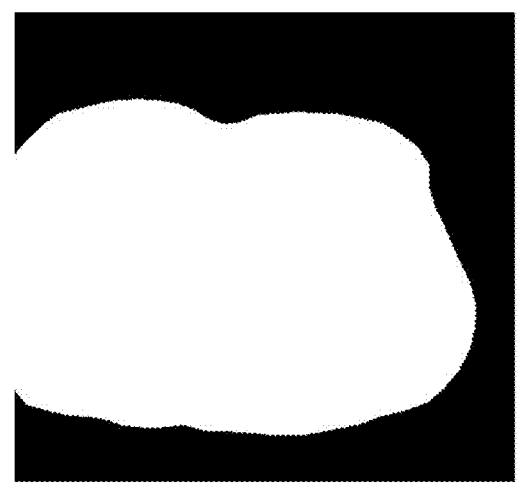
FIG. 39A  FIG. 39B

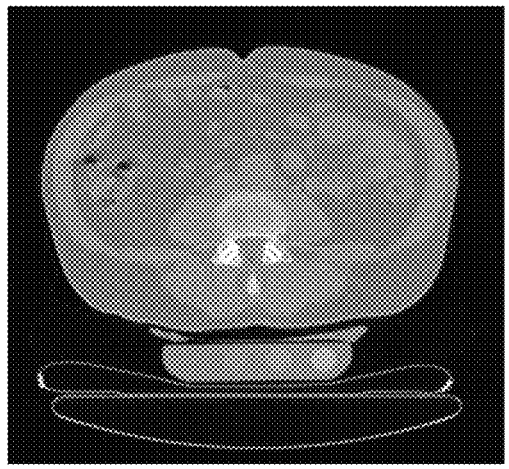
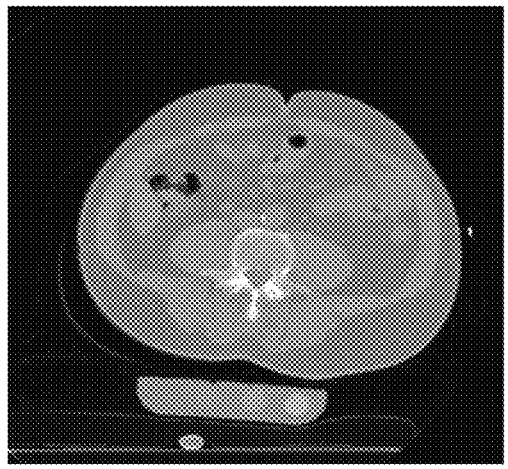
FIG. 61A  FIG. 61B
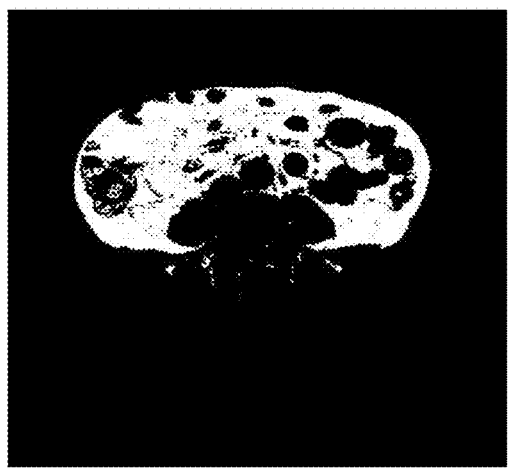
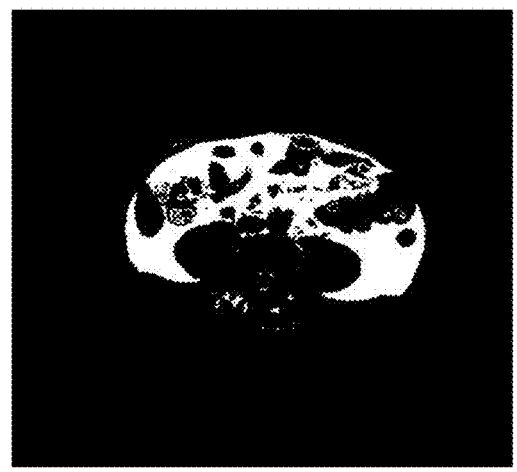
FIG. 61C  FIG. 61D

METHODS OF COMPUTING PERICARDIAL AND ABDOMINAL FAT AND METHODS FOR MOTION COMPENSATION

RELATED APPLICATIONS

This invention is a divisional of U.S. patent application Ser. No. 12/084,757 filed Jul. 16, 2010 (16 Jul. 2010), which is a Nationalization of PCT Patent Application Serial No. PCT/US06/43916, filed Nov. 13, 2006, published as WO2007/058997 on May 24, 2007, which claims priority to and the benefit of U.S. Provisional Patent Application Ser. Nos. 60/736,037 filed 11 Nov. 2005 and 60/812,714 filed 8 Jun. 2006.

GOVERNMENT SPONSORSHIP

This invention was made with government support from the National Science Foundation. This work was supported in part by National Science Foundation under Grants IIS-9985482 and IIS-0335578 NSF and IIS-0431144.

BACKGROUND OF THE INVENTION

1. Field of the Invention

The present invention relates generally to a scoring method for vulnerable patients and a scoring rate for ranking a patient's risk.

More particularly, the present invention relates to a scoring method for vulnerable patients, such as cardiovascular vulnerability, and a scoring rate for ranking a patient's risk of a problem, such as a cardiovascular event or stroke, where the scoring rate includes data obtained from imaging apparatuses that are capable of discerning body fat, plaques, and other factors that place a patient at risk for problems such as a cardiovascular event or stroke. The fat and plaque data include density and at least one additional factor, where the additional factor is selected from the group consisting of distribution, location, size, shape and compositional variation.

2. Description of the Related Art

Fast computed tomography (CT) is rapidly emerging as the first line noninvasive imaging screening tool for detection of cardiovascular vulnerable patients. Electron beam CT (EBCT) has been utilized over a decade for imaging calcification in coronary arteries. More recently fast spiral CT has shown capabilities nearly equal to EBCT for imaging calcification in the heart as well as for noninvasive coronary angiography. Each of these imaging techniques offers certain strengths which currently justify their limited clinical value. Despite the controversy around the diagnostic value and accuracy of a calcium score for prediction of future cardiovascular events, imaging coronary calcification provides valuable information for risk stratification and assessment for patients with respect to future cardiovascular events, particularly, in asymptomatic patient populations and has recently received much credence.

However, it has been known among pioneering calcium imaging investigators that the existing scoring system for quantification of calcium is complicated by significant problems of reproducibility between different centers and manufacturers as well as within the same center. More importantly, the current calcium scoring technique under utilizes the range of data that can currently be obtained by CT coronary imaging or can be derived from the CT coronary images.

In summary, the current calcium scoring technique is hampered by: 1) a lack of equipment and software standardization resulting in unaccepted standard deviations between and within studies; and 2) it's inability to utilize additional information available from the imaging techniques to improve calcium scoring.

Thus, there is a need in the art for a different scoring technique that combines traditional calcium scoring with other more refined calcium data and/or fat data to produce a risk stratification scoring index for vulnerable patients.

SUMMARY OF THE INVENTION

The present invention provides a method for ranking patients based on a scoring rate derived from imaging-based data, where the data includes information on fat, plaques, and/or other physiologically image-discernible structures (vasa vasorum, other micro-vascularizations, etc.) and where the scoring rate ranks patients with respect to their vulnerability to cardiovascular events such as heart attacks, strokes or other similar cardiovascular events. The scoring rate includes density data of fat, plaques, and/or other physiologically image-discernible structures and at least one additional type of data, where the additional type of data is selected from the group consisting of distribution, location, size, shape and compositional variation of fat, plaque, and/or other physiologically image-discernible structures.

The present invention also provides a scoring rate or ranking system derived from imaging-based data, where the system includes data concerning bodily fat, plaques, and/or other physiologically image-discernible structures (vasa vasorum, other micro-vascularizations, etc.) and where the scoring rate ranks patients with respect to their vulnerability to cardiovascular events such as heart attacks, strokes or other similar cardiovascular events. The ranking system includes a scoring rate having fat, plaques, and/or other physiologically image-discernible structure density data and at least one additional type of data, where the additional type of data is selected from the group consisting of distribution, location, size, shape and compositional variation of fat, plaque, and/or other physiologically image-discernible structures.

The present invention provides a method for determining the data needed to rank patients with respect to their vulnerability to events such as heart attacks, strokes or other critical events, including the step of imaging a portion of a patient's body and determining a density of fat, plaques, and/or other physiologically image-discernible structures to form an image data set and at least one additional factor selected from the group consisting of distribution, location, size, shape and compositional variation of fat, plaques, and/or other physiologically image-discernible structures from the image data set.

The present invention also provides a method for determining the data needed to rank patients with respect to their vulnerability to events such as heart attacks, strokes or other critical events, including the step of imaging a portion of a patient's body to form a first image data set, imaging the same portion of the patient's body to form a second image data set, and determining a density of fat, plaques, and/or other physiologically image-discernible structures and at least one additional factor selected from the group consisting of distribution, location, size, shape and compositional variation of fat, plaques, and/or other physiologically image-discernible structures from the image data sets.

The present invention provides a method for determining the data needed to rank patients with respect to their vulnerability to events such as heart attacks, strokes or other critical events, including the step of imaging a portion of a patient's body, injecting a contrast agent into a patient, imaging the same portion of the patient's body to form a second image data set, and determining a density of fat, plaques, and/or other physiologically image-discernible structures and at least one additional factor selected from the group consisting of distribution, location, size, shape and compositional variation of fat, plaques, and/or other physiologically image-discernible structures from the image data sets.

The method and algorithms to compute fat automatically are described in the Evaluation of Abdominal Fat Burden Quantification in CT section herein and the Automatic Segmentation of Abdominal Fat from CT Data section herein.

The algorithms to model the shape and motion of arteries of the coronary artery tree are described in the Functional Morphology Analysis of the Left Anterior Descending Coronary Artery in EBCT Images section herein.

New Vulnerability Scoring Indices

The present invention provides a scoring index derived from data collected from CT, PETCT and/or MRI soft tissue characterizations as well as data collected patient specific data and data from physician observations.

Coronary Scoring Index

The present invention provides a scoring index derived from imaging data comprising coronary calcium data. The coronary calcium data include: (1) overall coronary calcium density data, (2) coronary calcium distribution data, (3) coronary calcium location data, (4) coronary calcium shape data, (5) coronary calcium size data, (6) coronary calcium structural data and/or (7) coronary calcium pattern data.

The coronary calcium data can optionally include: (1) overall coronary plaque density, (2) coronary plaque distribution data, (3) coronary plaque location data, (4) coronary plaque shape data, (5) coronary plaque size data, (6) coronary plaque structural data and/or (7) coronary plaque pattern data.

Whole Heart Scoring Index

The present invention provides a scoring index derived from imaging data comprising coronary calcium data, and non-coronary arterial and/or veinal data.

Coronary Calcium Data

The coronary calcium data include: (1) overall coronary calcium density data, (2) coronary calcium distribution data, (3) coronary calcium location data, (4) coronary calcium shape data, (5) coronary calcium size data, (6) coronary calcium structural data, and/or (7) coronary calcium pattern data.

The coronary calcium data can optionally include: (1) overall coronary plaque density, (2) coronary plaque distribution data, (3) coronary plaque location data, (4) coronary plaque shape data, (5) coronary plaque size data, (6) coronary plaque structural data and/or (7) coronary plaque pattern data.

Non-Coronary Data

The non-coronary data includes (1) non-coronary calcium data, (2) non-coronary plaque data, (3) heart structural data, (4) microvascularization data, and/or (5) pericardial fat data.

The non-coronary calcium data include: (a) overall non-coronary arterial and/or veinal calcium density data, (b) non-coronary arterial and/or veinal calcium distribution data, (c) non-coronary arterial and/or veinal calcium location data, (d) non-coronary arterial and/or veinal calcium shape data, (e) non-coronary arterial and/or veinal calcium size data, (f) non-coronary arterial and/or veinal calcium structural data, and/or (g) non-coronary calcium pattern data.

The non-coronary plaque data include: (a) overall non-coronary arterial and/or veinal plaque density, (b) non-coronary arterial and/or veinal plaque distribution data, (c) non-coronary arterial and/or veinal plaque location data, (d) non-coronary arterial and/or veinal plaque shape data, (e) non-coronary arterial and/or veinal plaque size data, (f) non-coronary arterial and/or veinal plaque structural data and/or (g) non-coronary arterial and/or veinal plaque pattern data.

The heart structural data include: (a) muscle thickness, and/or (b) valve structure.

The microvascularization data include: (a) overall cardial microvascularization density, (b) cardial microvascularization distribution data, (c) cardial microvascularization location data, (d) cardial microvascularization shape data, (e) cardial microvascularization size data, (f) cardial microvascularization structural data and/or (g) cardial microvascularization pattern data.

The pericardial fat data include: (a) overall pericardial fat density data, (b) pericardial fat distribution data, (c) pericardial fat location data, (d) pericardial fat shape data, (e) pericardial fat size data, (f) pericardial fat structural, and/or (g) pericardial fat data.

Hip-to-Lips Scoring Index

The present invention provides a scoring index derived from imaging data comprising coronary calcium data, non-coronary data, and non-cardiac data.

Coronary Calcium Data

The coronary calcium data include: (1) overall coronary calcium density data, (2) coronary calcium distribution data, (3) coronary calcium location data, (4) coronary calcium shape data, (5) coronary calcium size data, (6) coronary calcium structural data, and/or (7) coronary calcium pattern data.

The coronary calcium data can optionally include: (1) overall coronary plaque density, (2) coronary plaque distribution data, (3) coronary plaque location data, (4) coronary plaque shape data, (5) coronary plaque size data, (6) coronary plaque structural data and/or (7) coronary plaque pattern data.

Non-Coronary Data

The non-coronary data include: (1) non-coronary calcium data, (2) non-coronary plaque data, (3) heart structural data, (4) microvascularization data, and/or (5) pericardial fat data.

The non-coronary calcium data include: (a) overall non-coronary arterial and/or veinal calcium density data, (b) non-coronary arterial and/or veinal calcium distribution data, (c) non-coronary arterial and/or veinal calcium location data, (d) non-coronary arterial and/or veinal calcium shape data, (e) non-coronary arterial and/or veinal calcium size data, (f) non-coronary arterial and/or veinal calcium structural data, and/or (g) non-coronary calcium pattern data.

The non-coronary plaque data include: (a) overall non-coronary arterial and/or veinal plaque density, (b) non-coronary arterial and/or veinal plaque distribution data, (c) non-coronary arterial and/or veinal plaque location data, (d) non-coronary arterial and/or veinal plaque shape data, (e) non-coronary arterial and/or veinal plaque size data, (f)

non-coronary arterial and/or veinal plaque structural data and/or (g) non-coronary arterial and/or veinal plaque pattern data.

The heart structural data include: (a) muscle thickness, and/or (b) valve structure;

The microvascularization data including (a) overall cardial microvascularization density, (b) cardial microvascularization distribution data, (c) cardial microvascularization location data, (d) cardial microvascularization shape data, (e) cardial microvascularization size data, (f) cardial microvascularization structural data and/or (g) cardial microvascularization pattern data; and/or The pericardial fat data include: (a) overall pericardial fat density data, (b) pericardial fat distribution data, (c) pericardial fat location data, (d) pericardial fat shape data, (e) pericardial fat size data, (f) pericardial fat structural, and/or (g) pericardial fat data.

Non-Cardiac Data

The non-cardiac data include: (1) non-cardiac arterial and/or veinal calcium data, (2) non-cardiac arterial and/or veinal plaque data, (3) organ structural data, (4) non-cardiac microvascularization data, and/or (5) non-cardiac fat data.

The non-cardiac arterial and/or veinal calcium data include: (a) overall non-cardiac arterial and/or veinal calcium density data. (b) non-cardiac arterial and/or veinal calcium distribution data. (c) non-cardiac arterial and/or veinal calcium location data, (d) non-cardiac arterial and/or veinal calcium shape data, (e) non-cardiac arterial and/or veinal calcium size data, (f) non-cardiac arterial and/or veinal calcium structural data, and/or (g) non-cardiac arterial and/or veinal calcium pattern data.

The non-cardiac arterial and/or veinal plaque data include: (a) overall non-cardiac arterial and/or veinal plaque density, (b) non-cardiac arterial and/or veinal plaque distribution data, (c) non-cardiac arterial and/or veinal plaque location data, (d) non-cardiac arterial and/or veinal plaque shape data, (e) non-cardiac arterial and/or veinal plaque size data, (f) non-cardiac arterial and/or veinal plaque structural data and/or (g) non-cardiac arterial and/or veinal plaque pattern data.

The organ structural data include: (a) gross morphologic data, (b) histological data, (c) defect data, and/or (d) abnormality data.

The non-cardiac microvascularization data include: (a) overall non-cardiac microvascularization density, (b) non-cardiac microvascularization distribution data, (c) non-cardiac microvascularization location data, (d) non-cardiac microvascularization shape data, (e) non-cardiac microvascularization size data, (f) non-cardiac microvascularization structural data and/or (g) non-cardiac microvascularization pattern data.

The non-cardiac fat data include: (a) overall epicardial, thoracic and/or visceral fat density data, (b) epicardial, thoracic and/or visceral fat distribution data, (c) epicardial, thoracic and/or visceral fat location data, (d) epicardial, thoracic and/or visceral fat shape data, (c) epicardial, thoracic and/or visceral fat size data, (f) epicardial, thoracic and/or visceral fat structural data, and/or (g) epicardial, thoracic and/or visceral fat data.

Whole Body Scoring Index

The present invention provides a scoring index derived from imaging data comprising coronary calcium data, non-coronary data, non-cardiac data, and non-hip-to-lip data.

Coronary Calcium Data

The coronary calcium data include: (1) overall coronary calcium density data, (2) coronary calcium distribution data, (3) coronary calcium location data, (4) coronary calcium shape data, (5) coronary calcium size data, (6) coronary calcium structural data, and/or (7) coronary calcium pattern data.

The coronary calcium data can optionally include: (1) overall coronary plaque density, (2) coronary plaque distribution data, (3) coronary plaque location data, (4) coronary plaque shape data, (5) coronary plaque size data, (6) coronary plaque structural data and/or (7) coronary plaque pattern data.

Non-Coronary Data

The non-coronary data include: (1) non-coronary calcium data, (2) non-coronary plaque data, (3) heart structural data, (4) microvascularization data, and/or (5) pericardial fat data.

The non-coronary calcium data include: (a) overall non-coronary arterial and/or veinal calcium density data, (b) non-coronary arterial and/or veinal calcium distribution data, (c) non-coronary arterial and/or veinal calcium location data, (d) non-coronary arterial and/or veinal calcium shape data, (e) non-coronary arterial and/or veinal calcium size data, (f) non-coronary arterial and/or veinal calcium structural data, and/or (g) non-coronary calcium pattern data.

The non-coronary plaque data include: (a) overall non-coronary arterial and/or veinal plaque density, (b) non-coronary arterial and/or veinal plaque distribution data, (c) non-coronary arterial and/or veinal plaque location data, (d) non-coronary arterial and/or veinal plaque shape data, (e) non-coronary arterial and/or veinal plaque size data, (f) non-coronary arterial and/or veinal plaque structural data and/or (g) non-coronary arterial and/or veinal plaque pattern data.

The heart structural data include: (a) muscle thickness, and/or (b) valve structure:

The microvascularization data including (a) overall cardial microvascularization density, (b) cardial microvascularization distribution data, (c) cardial microvascularization location data, (d) cardial microvascularization shape data, (e) cardial microvascularization size data, (f) cardial microvascularization structural data and/or (g) cardial microvascularization pattern data; and/or The pericardial fat data include: (a) overall pericardial fat density data, (b) pericardial fat distribution data, (c) pericardial fat location data, (d) pericardial fat shape data, (e) pericardial fat size data, (f) pericardial fat structural, and/or (g) pericardial fat data.

Non-Cardiac Data

The non-cardiac data include: (1) non-cardiac arterial and/or veinal calcium data, (2) non-cardiac arterial and/or veinal plaque data, (3) organ structural data, (4) non-cardiac microvascularization data, and/or (5) non-cardiac fat data.

The non-cardiac arterial and/or veinal calcium data include: (a) overall non-cardiac arterial and/or veinal calcium density data, (b) non-cardiac arterial and/or veinal calcium distribution data, (c) non-cardiac arterial and/or veinal calcium location data, (d) non-cardiac arterial and/or veinal calcium shape data, (e) non-cardiac arterial and/or veinal calcium size data, (f) non-cardiac arterial and/or veinal calcium structural data, and/or (g) non-cardiac arterial and/or veinal calcium pattern data.

The non-cardiac arterial and/or veinal plaque data include: (a) overall non-cardiac arterial and/or veinal plaque density, (b) non-cardiac arterial and/or veinal plaque distribution data, (c) non-cardiac arterial and/or veinal plaque location data, (d) non-cardiac arterial and/or veinal plaque shape data, (e) non-cardiac arterial and/or veinal plaque size data, (f) non-cardiac arterial and/or veinal plaque structural data and/or (g) non-cardiac arterial and/or veinal plaque pattern data.

The organ structural data include: (a) gross morphologic data, (b) histological data, (c) defect data, and/or (d) abnormality data.

The non-cardiac microvascularization data include: (a) overall non-cardiac microvascularization density, (b) non-cardiac microvascularization distribution data, (c) non-cardiac microvascularization location data, (d) non-cardiac microvascularization shape data, (e) non-cardiac microvascularization size data, (f) non-cardiac microvascularization structural data and/or (g) non-cardiac microvascularization pattern data.

The non-cardiac fat data include: (a) overall epicardial, thoracic and/or visceral fat density data, (b) epicardial, thoracic and/or visceral fat distribution data, (c) epicardial, thoracic and/or visceral fat location data, (d) epicardial, thoracic and/or visceral fat shape data, (e) epicardial, thoracic and/or visceral fat size data, (f) epicardial, thoracic and/or visceral fat structural data, and/or (g) epicardial, thoracic and/or visceral fat data.

Non-Hip-to-Lip Data

The non-hip-to-lip data include: (a) overall muscle structure, (b) overall tendon and ligament structure, (c) bone density and structure, (d) neurological density and structure, and (e) cancer density, location and structure.

Whole Patient Scoring Index

The present invention provides a scoring index derived from imaging data comprising coronary calcium data, non-coronary data, non-cardiac data, non-hip-to-lip data, and general patient data.

Coronary Calcium Data

The coronary calcium data include: (1) overall coronary calcium density data, (2) coronary calcium distribution data, (3) coronary calcium location data, (4) coronary calcium shape data, (5) coronary calcium size data, (6) coronary calcium structural data, and/or (7) coronary calcium pattern data.

The coronary calcium data can optionally include: (1) overall coronary plaque density, (2) coronary plaque distribution data, (3) coronary plaque location data, (4) coronary plaque shape data, (5) coronary plaque size data, (6) coronary plaque structural data and/or (7) coronary plaque pattern data.

Non-Coronary Data

The non-coronary data include: (1) non-coronary calcium data, (2) non-coronary plaque data, (3) heart structural data, (4) microvascularization data, and/or (5) pericardial fat data.

The non-coronary calcium data include: (a) overall non-coronary arterial and/or veinal calcium density data, (b) non-coronary arterial and/or veinal calcium distribution data, (c) non-coronary arterial and/or veinal calcium location data, (d) non-coronary arterial and/or veinal calcium shape data, (e) non-coronary arterial and/or veinal calcium size data, (f) non-coronary arterial and/or veinal calcium structural data, and/or (g) non-coronary calcium pattern data.

The non-coronary plaque data include: (a) overall non-coronary arterial and/or veinal plaque density, (b) non-coronary arterial and/or veinal plaque distribution data, (c) non-coronary arterial and/or veinal plaque location data, (d) non-coronary arterial and/or veinal plaque shape data, (e) non-coronary arterial and/or veinal plaque size data, (f) non-coronary arterial and/or veinal plaque structural data and/or (g) non-coronary arterial and/or veinal plaque pattern data.

The heart structural data include: (a) muscle thickness, and/or (b) valve structure;

The microvascularization data including (a) overall cardial microvascularization density, (b) cardial microvascularization distribution data, (c) cardial microvascularization location data, (d) cardial microvascularization shape data, (e) cardial microvascularization size data, (f) cardial microvascularization structural data and/or (g) cardial microvascularization pattern data; and/or The pericardial fat data include: (a) overall pericardial fat density data, (b) pericardial fat distribution data, (c) pericardial fat location data, (d) pericardial fat shape data, (e) pericardial fat size data, (f) pericardial fat structural, and/or (g) pericardial fat data.

Non-Cardiac Data

The non-cardiac data include: (1) non-cardiac arterial and/or veinal calcium data, (2) non-cardiac arterial and/or veinal plaque data, (3) organ structural data, (4) non-cardiac microvascularization data, and/or (5) non-cardiac fat data.

The non-cardiac arterial and/or veinal calcium data include: (a) overall non-cardiac arterial and/or veinal calcium density data, (b) non-cardiac arterial and/or veinal calcium distribution data, (c) non-cardiac arterial and/or veinal calcium location data, (d) non-cardiac arterial and/or veinal calcium shape data, (e) non-cardiac arterial and/or veinal calcium size data, (f) non-cardiac arterial and/or veinal calcium structural data, and/or (g) non-cardiac arterial and/or veinal calcium pattern data.

The non-cardiac arterial and/or veinal plaque data include: (a) overall non-cardiac arterial and/or veinal plaque density, (b) non-cardiac arterial and/or veinal plaque distribution data, (c) non-cardiac arterial and/or veinal plaque location data, (d) non-cardiac arterial and/or veinal plaque shape data, (e) non-cardiac arterial and/or veinal plaque size data, (f) non-cardiac arterial and/or veinal plaque structural data and/or (g) non-cardiac arterial and/or veinal plaque pattern data.

The organ structural data include: (a) gross morphologic data, (b) histological data, (c) defect data, and/or (d) abnormality data.

The non-cardiac microvascularization data include: (a) overall non-cardiac microvascularization density, (b) non-cardiac microvascularization distribution data, (c) non-cardiac microvascularization location data, (d) non-cardiac microvascularization shape data, (e) non-cardiac microvascularization size data, (f) non-cardiac microvascularization structural data and/or (g) non-cardiac microvascularization pattern data.

The non-cardiac fat data include: (a) overall epicardial, thoracic and/or visceral fat density data, (b) epicardial, thoracic and/or visceral fat distribution data, (c) epicardial, thoracic and/or visceral fat location data, (d) epicardial, thoracic and/or visceral fat shape data, (e) epicardial, thoracic and/or visceral fat size data, (f) epicardial, thoracic and/or visceral fat structural data, and/or (g) epicardial, thoracic and/or visceral fat data.

Non-Hip-to-Lip Data

The non-hip-to-lip data include: (a) overall muscle structure, (b) overall tendon and ligament structure, (c) bone density and structure, (d) neurological density and structure, and (e) cancer density, location and structure.

General Patient Data

The general patient data include: (a) age, weight, (b) height, (c) medical history, (d) family medical history, (e) education, (f) eating habits, (g) diet, (h) exercise.

Formulas

The present invention provides a scoring index given by the formula:

$$Score = \sum_i w_i D_i$$

where:
i is an integer having a value between 1 and 5,
$D_1$ is a coronary calcium sub-score,
$D_2$ is a non-coronary sub-score,
$D_3$ is a non-cardiac sub-score,
$D_4$ is a non-hip-to-lip sub-score,
$D_5$ is a general patient sub-score,
$w_1$ is a weighting factor for the $D_1$ sub-score,
$w_2$ is a weighting factor for the $D_2$ sub-score,
$w_3$ is a weighting factor for the $D_3$ sub-score,
$w_4$ is a weighting factor for the $D_4$ sub-score, and
$w_5$ is a weighting factor for the $D_5$ sub-score.

The present invention provides a coronary calcium sub-score given by the formula:

$$D_1 = \sum_j w_j CC_j$$

where
each $CC_j$ is a type of coronary calcium data and each corresponding $w_j$ is a weighting factor for each type of coronary calcium data.

The present invention provides a non-coronary calcium sub-score given by the formula:

$$D_2 = \sum_k w_k NCC_k$$

where
each $NCC_k$ is a type of non-coronary calcium data and each corresponding $w_k$ is a weighting factor for each type of coronary calcium data.

The present invention provides a non-cardiac calcium sub-score given by the formula:

$$D_3 = \sum_l w_l NH_l$$

where
each $NH_l$ is a type of non-cardiac calcium data and each corresponding $w_l$ is a weighting factor for each type of non-cardiac calcium data.

The present invention provides a non-cardiac calcium sub-score given by the formula:

$$D_4 = \sum_m w_m NHL_m$$

where
each $NHL_m$ is a type of non-cardiac calcium data and each corresponding $w_m$ is a weighting factor for each type of non-cardiac calcium data.

The present invention provides a non-cardiac calcium sub-score given by the formula:

$$D_5 = \sum_n w_n GP_n$$

where
each $GP_n$ is a type of non-cardiac calcium data and each corresponding $w_n$ is a weighting factor for each type of non-cardiac calcium data.

The present invention provides a scoring index given by the formula:

$$Score = \sum_i w_i \sum_{n_i} w_{n_i} PD_{n_i}$$

where:
each $PD_{n_i}$ is a specific class of patient data selected from the group consisting of coronary calcium data, non-coronary data, non-cardiac data, non-hip-to-lip data, and general patient data,
$w_i$ is a weighting factor for each class of patient data $PD_{n_i}$,
each $w_i$ is a weighting factor for each type of data within each class of patient data $PD_{n_i}$,
i is an integer having a value between 1 and 5, and
each $n_i$ is an integer having a value that ranges over a number of data types within between each data class.

The present invention provides a scoring index given by the formula:

$$Score = \sum_i w_i DT_i$$

where:
i is an integer having a value between 1 and 5,
$DT_i$ is a patient data type selected from the group consisting of coronary calcium data types, non-coronary data types, non-cardiac data types, non-hip-to-lip data types, and general patient data types.

The above scoring indexes can also include exo-cardiac data such as arteries—arota, femeral, illac characteristic data, non-artery data such as fat (abdominal; subcutaneous—under skin: visceral—organ or tissue related) and thoracic—chest cavity, lung diseases, kidney diseases, bone density.

Epicardial and/or pericardial fat, thoracic fat including peri-aortic fat and peradvential fat (coronary, carotid, aorta, etc.) can also be measured to further evaluate and improve the risk assessment. Moreover, total visceral fat including chest (pericardial etc.) and abdominal fat can be sued as an indicator of a metabolic syndrome and be combined with calcium scoring to enhance coronary risk assessment.

The data for the above scoring indices can be derived from one time imagining identifying the above information, contrast enhanced imagining, dual absorption imaging—two scan with different energetic X-ray fields—low energy for fat characterization, high energy for all other characterizations normal and higher energy for bone density characterization.

BRIEF DESCRIPTION OF THE DRAWINGS

The invention can be better understood with reference to the following detailed description together with the appended illustrative drawings in which like elements are numbered the same:

FIG. 7 depicts a coronary artery with atherosclerotic plaques. There is hemorrhage into the plaque in the middle of this photograph;

FIG. 8 depicts cross-section of the coronary artery with occlusion with slight calcification in the right;

FIGS. 9A-E depict the formation procedure of the plaque along with the numerical classification;

FIG. 10 depicts a fatty dot or streak that are identified as yellow spots;

FIG. 11 depicts an image of a segmentation map of a section of the atherosclerotic plaque;

FIGS. 18A-D depict a beginning of left atrio-ventricular groove marks LCX in the left two figures (non-contrast enhanced, contrast enhanced), and a heart end 4-5 slices after lever first appears in the scan in the right two figures (non-contrast enhanced, contrast enhanced);

FIG. 19 depicts the determination of an RAO axis from transverse slices;

FIG. 20 depicts the determination of approximate 4-CH axis from RAO slices;

FIG. 21 depicts the determination of short axis of the heart from approximate 4-ch slices;

FIGS. 22 and 23 depict the determination of 4-CH axis from SA slices;

FIGS. 33A-J depict model constructions: (A) Geometric heart model (Qc Visible Productions™, LLC), (B) Geometric model and motion data of a human subject's heart extracted using MRI-SPAMM [33], [34], (C-G) Frames from the animated heart model, from ES to ED, and (H-J) LAD deformations from ED to ES;

FIGS. 36A-F depict estimated shape-motion parameters of the LAD for subjects S3 and S4: (A,B) logλ, longitudinal displacement with respect to the long axis of the heart; (C,D) logρ, radial displacement with respect to the long axis of the heart; and (E,F) θ, angular displacement with respect to the long axis of the heart (in degrees);

FIGS. 37A-F depict estimated shape-motion parameters of the LAD for subjects S1 and S2: (A,B) logλ, longitudinal displacement with respect to the long axis of the heart; (C,D) logρ, radial displacement with respect to the long axis of the heart; and (E,F) θ, angular displacement with respect to the long axis of the heart (in degrees);

FIGS. 38A-B depict removal of equipment-related artifacts: (A) original CT image, and (B) after artifact (e.g., table, wire) removal;

FIGS. 39A-B depict human body contour detection: (A) original CT image, and (B) filled human contour;

FIGS. 61A-H depict a series of CT images: (A,B) Original CT images from Subject-1 and Subject-2, respectively. (C,D) Estimated visceral fat using AFACT. (E,F) Estimated subcutaneous fat using AFACT. (G,H) Estimated total fat using AFACT.

DETAILED DESCRIPTION OF THE INVENTION

Figure 3:
FIG. 3 depicts a photomicrograph of atheroma (type IV lesion) in proximal left anterior descending coronary artery.

A new risk assessment scoring index can be derived from imaging data of a patients heart or chest cavity and preferably imaging data of a patient hip to lip region. CT imaging techniques can provide data about calcification density, a measure of a total amount of calcification within an image region, and also produce data on the distribution of calcification, the size, shape and location of individual calcium deposits, the shade, size and location of calcified plaques and the distribution, size, shape and location of fat deposits in the chest cavity, abdomen, and in, on and around various organs such as the heart, liver, kidneys, etc. that can be imaged in a "hip to lip" CT image or image session. The inventors have also found that a new method for analyzing CT image data can be implemented for the determination and/or construction of various new cardiovascular patient risk assessment scoring.

The present invention broadly relates to a method for acquiring risk assessment data from a imaging device, including the step of acquiring imaging data from a patient at least from the patient's chest cavity including the heart and preferably data from a hip to lip scan. The acquired data is then analyzed to determine calcium density, location, shape and size. From the calcium data, a refined calcium score is derived. Optionally, the acquired data can be analyzed to determine fat density, location, shape and size and producing a score derived from both fat and calcium data. Moreover, a first set of imaging data can be acquire prior to the introduction of a contrast agent into the patient and a second and potentially third set of imaging data, during and/or after contract agent introduction. The contrast enhanced images will allow difference data to be derived and to image structures that are either invisible in the absence of the contrast agent to are very difficult to quantify in the absence of a contrast agent. Generally, the second data set is acquired over a time frame that permits the contrast agent to infiltrate the desired structures. Such infiltration permits the imaging of microvascularizations such as vaso vasora and other structure such as arterial plaques or plaques in critical veins.

The present invention also relates to scoring indices including calcium only imaging derived data, fat only imaging derived data, or a combination of imaging derived calcium and fat data. One preferred class of scoring indices includes global and/or site specific calcium density data, global and/or site specific calcium distribution data, and site specific size, shape and location calcification data. Another preferred class of scoring indices include global and/or site specific calcium density data and global and/or site specific fat density data. Another preferred class of scoring indices include global and/or site specific calcium density data, global and/or site specific fat density data, and global and/or site specific fat distribution. Another preferred class of scoring indices include global and/or site specific calcium density data, global and/or site specific fat density data, global and/or site specific fat distribution, and site specific fat deposits size, shape and location data. Another preferred class of scoring indices includes global and/or site specific calcium density data, global and/or site specific calcium distribution data, site specific size, shape and location calcification data and at least one of global and/or site specific fat density data, global and/or site specific fat distribution, or site specific fat deposits size, shape and location data. Another preferred class of scoring indices include global and/or site specific fat density data, global and/or site specific fat distribution, or site specific fat deposits size, shape and location data. To these scoring indices, other factors can also be included such as dietary habits, weight, height, age, other body fat measurements, medical history, EKG data, etc.

Risk Scoring
Pericardial Fat

CT, EBCT, and/or MRI scans can be used to measure fat around the heart both epicardial and pericardial (under pericardium and outside of pericardium). The data cannot only be of a global nature, but also of a site specific nature, where both global and site specific data being preferred. The data can be used in alone or in conjunction with plaque/calcium data for coronary risk assessment. The epicardial and/or pericardial fat can be an indicator of inflammatory stimuli around the artery and can also provide a direct link to the presence of a metabolic syndrome. Usually, a pericardial fat layer can be visualized if careful administration and interpretation of the test is being done. Such a procedure can be automated by sophisticated software. As stated previously, a combination of plaque/calcium data and fat data can be used to develop a new coronary risk assessment scoring or ranking methodology, which is different from existing methodologies and is expected to be better than existing methodologies because not only is the global density be analyzed, but the distribution and site specific characteristics are being analyzed as well.

Besides epicardial and/or pericardial fat, thoracic fat including peri-aortic fat and peradvential fat (coronary, carotid, aorta, etc.) can also be measured to further evaluate and improve the risk assessment. Moreover, total visceral fat including chest (pericardial etc.) and abdominal fat can be used as an indicator of a metabolic syndrome and be combined with calcium scoring to enhance coronary risk assessment.

The present invention also relates to CT detection of microvascularizations such as vasa vasorum by subtracting images of regions of interest of pre and post contrast agent administration, e.g., extra vascular administration. The present invention also relates to CT detection of cap thickness by subtracting images of regions of interest pre and post contrast agent administration, e.g., intra luminal administration. The present invention also relates to CT detection of remodeling.

The present invention also relates to a method for extracting additional information from existing non-contrast CT, EBCT and/or MRI cardiac imaging data or non-contrast CT, EBCT and/or MRI "hip to lip" imagining data, where the additional data is used to the Agatston cumulative score or to produce a new cumulative score. The present invention also relates to a method for obtaining corresponding data or a "blush sign" using a contrast agent to permit identification of plaques, plaques with inflammation, leaking angiogenesis, permeable cap, intraplaque hemorrhage, and recently or silently ruptured plaques.

The present invention also relates to a graphical model of a portion of a human body including at least the cardiovascular system, especially the heart, which is registered to corresponding imaging data. The model and the data are then used to construct a template of the imaged body portion including a heart to extract region of interest (ROI) from imaging data including ROIs associated with the coronary arterial tree (CAT).

First, non contrast-enhanced imaging data such as CT imaging data is obtained from a patient. The imaging data can include data related to the cardiovascular system including some or all of carotid arteries, coronary arteries, the aorta and the femoral arteries. The imaging data can also include data related to myocardium to detect myocardial perfusion. The imaging data can also include data related to fat distribution in the abdomen versus other areas. The imaging data can also include data related to energy discrimination obtained at different energy levels. Once non-contrast imaging data is obtained, the data can be used to modify existing scoring formulas and as well, and preferably, for constructing new scoring formulas.

Second, contrast-enhanced imaging data such as CT imaging data is obtained from a patient. The imaging data can include data related to the cardiovascular system including some or all of carotid arteries, coronary arteries, the aorta and the femoral arteries. The imaging data can also include data related to myocardium to detect myocardial perfusion. The imaging data can also include data related to fat distribution in the abdomen versus other areas. The imaging data can also include data related to energy discrimination. Once non-contrast imaging data is obtained, the data can be used to modify existing scoring formulas and as well, and preferably, for constructing new scoring formulas.

Background and Significance

In the last century, the treatment and research for cardiovascular diseases (CVD), including coronary heart diseases (CHD), stroke and other CVDs have played a significant role in the improvement of the life style in the American Population, and is reflected in the 60% of decline in the mortality from CVD and CHD over the last five decades. However, despite this major effort CHD is still the major cause of death in most of the developed countries, including America, and constitute a major obstacle to reach the Healthy People 2010 Objectives set for the American People. Indeed CHD represents the major cause of death in men and women belong to the aged 60 years and older.

However, a brief history of the CVD's trends over the last 5 decades in the United States show that CVD has been the major cause of death, with heart disease ranking in first place and stroke ranking in the third place. In fact, CVD accounts more than 900,000 deaths annually only in the United States and about 12 million Americans have one kind of CVD. Moreover, 4 million Americans have had a stroke.

The mortality from CHD in the United States has continuously decline between 1968 and 1997. In fact, between 1985 and 1997, CHD mortality declined approximate 30% in both men and women. Prevention is one of the factors that contributed with up to 29% to decline number of cases of CHD.

Formation of Plaque

Atherogenesis or the formation of plaque starts at a very early age and the initial stages are silent. This stage is usually the formation of "fatty streaks." Fatty streaks are smooth raised plaques located beneath the endothelium (the blood vessel wall). They are composed primarily of foam cells (lipid laden macrophages) and may regress, remain dormant or progress to a more complicated atherosclerotic lesion.

Fibrous plaque represents the second phase of plaque development. As the fatty streak progresses, smooth muscle cells (not normally present in the subendothelial space) migrate from the media to the subendothelial space, where they proliferate and produce connective tissue to form a fibrous cap. The final phase in plaque development is the formation of a complicated lesion, which can manifest calcification, hemorrhage, ulceration and/or thrombosis. Cholesterol, particularly low-density lipoprotein (LDL), forms a fatty substance called plaque, which builds up on the arterial walls. Smaller plaques remain soft, but older, larger plaques tend to develop fibrous caps with calcium deposits.

Invasive Techniques for Evaluation of the Atherosclerotic Vulnerable Plaques

High-Frequency Intravascular Ultrasound (20 to 40 MHz)

This imaging technique is the only one that provides images in which the arterial geometry can be analyzed in vivo. However, the resolution of the ultrasound system is limited to its frequency. Also histopathologic research reported low sensitivities for intravascular ultrasound in detecting lipid-rich lesions; nevertheless ultrasound radiofrequency signal analysis might improve tissue characterization.

Angioscopy

Angioscopy has a high sensitivity to plaque visualization and thrombus, but its main constraint is its incapability to analyze layers in the arterial wall and to give a good estimation of cap thickness or lipid content.

Thermography

Studies have determined a strong correlation between histopathological specimens of ruptured atherosclerotic plaques and the presence activated macrophages in the plaque. Also it has been demonstrated that temperature heterogeneity can be used to determine plaque composition and macrophage mass. In general, coronary sinus thermography is not completely developed, but appears to be a very promising technique for a global evaluation of the vulnerable coronary arterial bed and the vulnerable patient.

IVUS Elastography

IVUS elastography is based on the assumption that tissue components have different hardness due to their histopathological composition and are expected to be compressed differently if a defined pressure is applied thereto. The main advantage of this technique is the ability for it to discriminate between soft and hard materials with the description of the properties of the vessel wall, and has the potential to identify plaque vulnerability. However, its major problem is the acquisition of in vivo data in a pulsating artery located in a contracting heart.

Optical Coherence Tomography (OCT)

Optical coherence tomography (OCT) is a laser based technique, which allows the visualization of atherosclerotic lesions and is capable of differentiating lipid tissue from water-based tissues. However, there exist limitations in in vivo intravascular imaging concerning image quality in the case of imaging through blood or large volumes of tissue and the rate of data acquisition time and multiple scattering.

Raman Spectroscopy

Raman spectroscopy is highly suitable for the identification of gross chemical changes in tissue, such as atherosclerosis but this technique is still is its early stages of development and one of its main advantages is the ability to discriminate in vivo among lipid-rich, calcified fibrotic plaques but it imposes the limitation of strong background fluorescence and the laser light absorption by the blood.

Near-Infrared (NIR) Spectroscopy

Near-infrared (NIR) spectroscopy has been used to determinate the chemical content of biological specimens, is based on the light absorption by organic molecules, and allows a detailed analysis of chemical composition. Its main advantage is the deeper penetration into the atherosclerotic plaque, but until now, NIR spectroscopy has been applied to in vitro studies. Non-invasive Techniques Non-Invasive Techniques for Evaluation of the Atherosclerotic Vulnerable Plaques Ultra Fast Computed Tomography (UFCT)

The main advantage of UFCT over regular CT is that it requires less time in the data acquisition process. Moreover, its remarkable achievements are the elimination of respiratory artifacts in the imaging acquisition. Histological UFCT studies support the correlation of calcified plaques with tissues densities >130 Hounsifield units. On the other hand, high-risk plaques usually lack calcium. This imposes challenging problem predicting coronary calcification and makes high calcium scoring highly sensitive.

Magnetic Resonance Imaging (MR)

High resolution MRI is one of the best techniques to detect vulnerable plaques during visualization of atherosclerotic plaques in vivo. Nevertheless, to detect vulnerable plaques, MRI lacks sufficient resolution for accurate measurements of plaque cap thickness and characterization of atherosclerotic lesions in the coronary circulation. An intravascular MRI technique has shown up to 80% of agreement with histopathology in analysis of intimal thickness and accurately determines the size of plaques. The disadvantages of this technique are acquisition time, ineligibility of patients with metal prostheses, requirement of claustrophobic patients for sedation or anesthesia, and cost.

Quantifying Coronary Calcium

Calcium in the coronary arteries can be quantified from CT images by using different scoring algorithms. Some of the current scoring methods are: (1) Conventional Agatston scoring with a 130-H threshold, (2) Modified Agatston with a 90-H threshold, (3) Calcium volume scoring, and (4) Calcium mass scoring.

Conventional Agatston with a 130-H Threshold

Agatston scoring is a method for quantifying coronary calcium with EBCT. The method is based on the maximum X-ray attenuation coefficient, or CT number (measured in Hounsfield units [HU]), and the area of calcium deposits. First, calcified lesions are identified on CT images by applying a threshold of 130 HU to the entire image set; tissues with densities equal to or greater than the threshold are considered to correspond to calcium.

For each coronary artery, i, a region of interest (ROI) is drawn around each calcified lesion, j. The maximum CT number, $CT_{ij}^{max}$, of the ROI is determined and used to assign a weighting factor, $w_{ij}$. The area, $A_{ij}$, of the ROI is also determined. The Agatston score, $S_{ij}$, is computed as the product of the weighting factor and the area as shown in equation (1):

$$s_{ij} = w_{ij} * A_{ij}$$

where, $$w_{ij} = \begin{cases} 1 & \text{if } 130HU \leq CT_{ij}^{max} < 200HU \\ 2 & \text{if } 200HU \leq CT_{ij}^{max} < 300HU \\ 3 & \text{if } 300HU \leq CT_{ij}^{max} < 400HU \\ 4 & \text{if } 400HU \leq CT_{ij}^{max} \end{cases}$$

The score for all lesions in all coronary arteries is summed to determine the total calcium burden:

$$s_{tot} = \sum_{i,j} S_{ij}$$

This method has many limitations: (1) the Agatston score was designed for a special modality and protocol and is not invariant with respect to image parameters, such as slice thickness, absolute CT numbers and reconstruction kernels, (2) it has a strong dependence on noise because it relies on the maximum CT number; (3) because weighting factors are used, the score increases nonlinearly with increasing amounts of calcium; (4) the Agatston score was originally based on data from contiguous, nonoverlapping, 3-mm slices acquired with EBCT, the score as calculated using the above equations must be adjusted for non-3-mm slices and overlapping slices; and (5) the score does not correspond to a physical measure.

Modified Agatston with a 90-H Threshold

Figure 1:
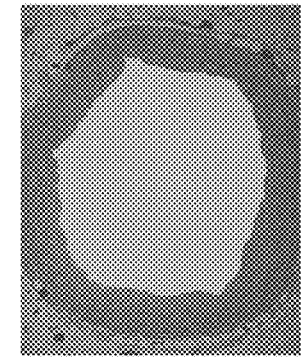
FIG. 1 depicts a normal coronary artery with no atherosclerosis and a widely patent lumen that can carry as much blood as the myocardium requires.

A Modified Agatston score using a lower threshold of 90-H, which has been used previously with helical CT, was calculated to take advantage of the greater signal-to-noise ratio of helical CT. FIG. 1 shows a correlations between Modified Agatston scoring with Helical CT and 130-H and 90-H thresholds. Regions of interest were defined by vessel and slice, and the appropriate weighting factor was applied to determine total scores and scores by vessel. For helical CT, calcifications were not enumerated by lesion as with the original Agatston method because of the bias introduced by vessels that course both within and through the cross-sectional slice of the heart, as has been previously noted.

TABLE I

Modified Agatston Scoring with Helical
CT and 130-H and 90-H Thresholds

| Weight Factor | Helical CT Threshold | |
|---|---|---|
| | 130 H | 90 H |
| 0 | <130 | <90 |
| 1 | 130-199 | 90-199 |
| 2 | 200-299 | 200-299 |
| 3 | 300-399 | 300-399 |
| 4 | >399 | >399 |

Table I shows a correlation between Modified Agatston scoring with helical CT and 130 H and 90 H thresholds.

Volume Scoring

This method uses volumetric measures to determine the calcium score. Similar to the Agatston scoring, a threshold of 130 HU is applied and ROIs are drawn around each calcified lesion. For each ROI, the number of voxels exceeding the threshold is summed. The volume score is simply calculated as the product of the number of voxels containing calcium, Nvoxel, and the volume of one voxel, Vvoxel $$V_{ij} = Vvoxel \cdot Nvoxel$$

Again, the volume score of individual lesions is summed to obtain a total volume score:

$$V_{tot} = \sum_{i,j} V_{ij}$$

Volume scoring provides more reproducible results than Agatston scoring, although it too has limitations: (1) volume score is vulnerable to overestimation of lesion size owing to partial volume effects; objects smaller than one voxel contribute to the score with the entire voxel volume; and (2) volume score does not necessarily represent the true volume of calcium, which depends on the applied threshold; and (3) the volume score is not a true physical measure.

Mass Scoring

This method uses absolute mass to get the calcium score. To obtain absolute values for calcium mass, a calibration measurement of a calcification with known hydroxyapatite density has to be performed and a calibration factor determined. The calibration factor. $c_{HA}$ is calculated as $$c_{HA} = \frac{\rho_{HA}}{\overline{CT_{HA}} - \overline{CT_{water}}}$$

where $\rho_{HA}$ is the density of the known calcification, $\overline{CT_{HA}}$ is the mean CT number of the known calcification, and $\overline{CT_{water}}$ is the mean CT number of water. Because the CT number of all materials except water depends on the X-ray spectrum, a specific calibration factor exists for each scanner and each scan protocol. The product of the calibration factor ($c_{HA}$), the volume, $V_{ij}$ as calculated above, and the mean CT number for each lesion ($\overline{CT_{ij}}$) gives the mass score ($m_{ij}$).

$$m_{ij} = c_{HA} * V_{ij} * \overline{CT_{ij}}$$

The total mass score is then the sum of the mass of all individual lesions:

$$m_{ij} = \sum_{i,j} m_{ij}$$

The mass score is given in milligrams and is a true physical measure. Initial results have shown mass scoring to be more reproducible than Agatston scoring, but it too has limitations: (1) the determined HA mass can only be the mass above the threshold used for segmentation; (2) the lower the threshold can be chosen, the more exactly the HA mass can be determined; (3) apart from effects due to fact that calcifications may contain non-calcium components, the calcium mass automatically corrects for linear partial volume effects, as objects smaller than the slice thickness are displayed with accordingly decreased mean CT numbers.

The Screening Pyramid

There are 140 Million Americans over the age of 35 years and 12.9 Million Americans have Coronary Heart Disease. This year 1.1 Million new cases of CHD will de diagnosed. Of the 140 Million Americans over the age of 35: 17.4% males between ages of 35-44 have CHD (24,360,000) and 13.6% females between the ages of 35-44 have CHD (Ser. No. 19/040,000). 50-60 Million people with CHD may not nave clinically evident disease, but they will have risk factors including: race, sex, family history, HTN, Diabetes, biological markers, etc. These people will be screened by simple questionnaires and non invasive blood tests in office based setting. 40-50 Million people with CHD have no symptoms, but they have risk factors, biological markers and lesions in their coronary arteries which are not severe enough to cause symptoms. These lesions may be progressing. This group of people will be screened by above questionnaire and blood tests and non invasive imaging study (CT). 2-3 Million people screened by above modalities will have significant lesions in their coronary arteries and will undergo interventional treatment.

Plaque Neovascularization/Aniogenesis—"Blush Sign"

X-ray angiography studies on plaque "blush sign", an angiographic sign of vulnerable plaques, which identifies plaques that retained die after a first pass of a contrast agent.

The inventors have previously correlated plaque blush sign with follow up clinical outcome in patients with repeated coronary angiography. The inventors found that blush sign was able to independently predict the future site of coronary occlusion. Blush sign identifies plaques with extensive leaking neovascularization and permeable surface both of which are indicators of plaque vulnerability.

Specifically, it has been very well established that the degree of stenosis of coronary arteries does not predict clinical events. Actually 50% of the acute coronary events occur in patients who have lesions less than 70% stenosed. Hence, in half of the patients with acute coronary events, one does not find a clinically significant lesion detected by angiography. The visible lesion on angiography is only the tip of the iceberg and represents only about 20% of the actual lesion. Various features of the plaque obtained by angiography such as, irregularity of the surface, the turbulence of flow, eccentricity and calcification do not predict the progression of the plaque.

The inventors discovered that neovascularization occurs within plaque and is a time related phenomenon. It translates into chronicity and progression of the atherosclerotic plaque. Because the pattern of atherosclerotic progression is non linear, affected by various variables, detection of plaque angiogenesis or Blush Sign may play a vital role in screening patients with clinically silent disease, yet having atherosclerosis which is progressing over time. Various features of plaque have been associated with progression. This includes the location of plaque mainly in the right coronary, left main and left anterior descending coronary arteries, the morphological feature of plaque, irregular and long plaques associated with progression.

Plaque angiogenesis is characterized by venules and capillaries that, until they mature, are hyperpermeable and leaky. Several studies have suggested that neovascularization in the walls of coronary arteries is associated with the presence of atherosclerotic plaque. Although the mechanisms responsible for the formation of these intraplaque microvessels are not well understood, intraplaque angiogenesis was found to play an important role in the development and progression of coronary arterial lesions. The factors responsible for plaque angiogenesis mainly are tissue hypoxia and inflammation. Blush Sign represents an area along the vessel wall which retains dye for a few seconds, while the rest of the dye has passed beyond the lesion. Although gravity may play a role in retention of dye in some lesions, this phenomenon has been seen in lesions located superiorly along the vessel wall. Hence, the inventors believe that the dye gains access to the lesion due to the leakiness of the cap or angiogenesis. In the previous studies, the inventors studied various features of the plaque including: plaque Blush Sign, calcification, morphological pattern of plaque including irregularity, eccentricity, overhanging edges, branch point lesion, and TIMI flow. The inventors defined plaque progression as >20% increase in size of the lesion on angiography. Fifty percent of the plaques which had progressed exhibited the Blush Sign in contrast to only 7% non-progressing plaques. The inventors have shown plaques with positive Blush Sign progress faster and are likely to cause near future events. In logistic regression, plaque Blush Sign (P=0.002), calcification (P=0.024), and a branch point location (P=0.001) predicted plaque progression. The odds ratio for plaque progression (ORp) was calculated as:

$$ORp = e^{2.5*BL + 1.8*CA + 2.6*BR}$$

Using an ORp of ⅓, the model has 81% sensitivity and 77% specificity. A second analysis in which each progressive lesion was compared to proximal and distal lesions, and to one in a different coronary artery, yielded similar results.

Experimental Section of the Invention

In this application, the inventors examined 22 relatively high risk, yet asymptomatic patients with multi-slice helical CT. Six of these patients showed indications of positive Blush Sign.

Atherosclerotic Plaque: Histology & Classification

Atherosclerosis is a gradual process that leads to a complete arterial occlusion and consequently leads to myocardial infarction. There have been studies that establish the role of inflammation in the initiation, progression and rupture of the vulnerable plaque. The focus is now on detecting such plaque, minimizing inflammation and thereby preventing myocardial infarction. However, because these lesions are usually moderate in size and buried inside the arterial wall, they are hard to detect and with many modalities being currently used, it is imperative to classify these plaques at various stages of their developments. Also necessary is the need to understand, what is known about the composition and structure of human atherosclerotic lesions and about the arterial sites at which they develop. On the basis of autopsy studies, The American Heart Association (AHA) has defined a standard for these lesions at different levels of their growth. These results threw some new light on the compositions of lesions and on the diversity of the mechanisms used.

The AHA decided to recommend the use of a standard numerical nomenclature of precisely defined lesion types to replace a variety of duplicate and vague terms. This nomenclature was necessary to have in place a template for each type of lesion, to serve as a reference to the many images being generated by invasive and non invasive techniques.

The AHA-recommended classification had been originally developed and used to convey the results of an inquiry into the compositions of atherosclerotic lesions as they silently develop over much of a lifetime in a population.

Referring now to FIG. 1, a normal coronary artery is shown with no atherosclerosis and a widely patent lumen that can carry as much blood as the myocardium requires. Anatomy of Vulnerable Plaque shows a cross-section of a normal artery with no atherosclerosis. This is the region of interest in finding out the anatomy of vulnerable plaque.

The Vulnerable Plaque has been defined as containing the five following elements: (1) large lipid core, (2) thin fibrous cap, (3) inflammatory changes at the shoulder of the fibrous cap, (4) decreased smooth muscle cells within the fibrous cap, and (5) increased angiogenesis within the intima and media.

Figure 2:
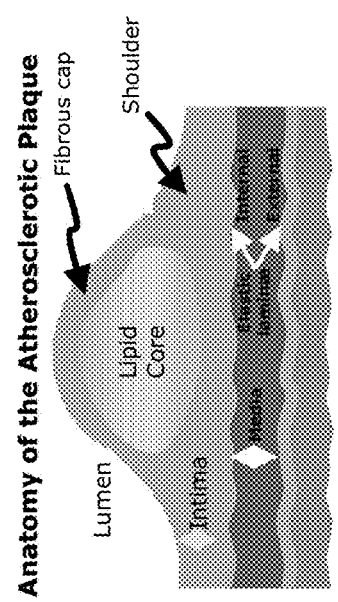
FIG. 2 shows the anatomy of a atherosclerotic plaque, which summarizes plaque structure.

Referring now to FIG. 2, the anatomy of an atherosclerotic plaque is shown, which summarizes plaque structure. However, this formation is not a sudden one, and takes place over many years. The AHA classification is based on the timeline of plaque development, from initial inflammation and formation of macrophages to the dense calcified plaque that lead to myocardial infarction.

Classification of Vulnerable Plaque as Recommended by the American Heart Association The AHA based classification deals with numerical classification of lesions. These are as follows:

Type I Lesions

A Type I or initial lesion contains enough atherogenic lipoprotein to elicit an increase in macrophages and formation of scattered macrophage foam cells. As in subsequent lesion types, the changes are more marked in locations of arteries with adaptive intimal thickening, which are present at constant locations in everyone from birth, do not obstruct the lumen and represent adaptations to local mechanical forces.

Type II Lesions

Type II lesions consist primarily of layers of macrophage foam cells and lipid-laden smooth muscle cells and include lesions grossly designated as fatty streaks. In the original classification, Ttype II lesions are subdivided into those at highly susceptible sites of arteries and prone to further development (type IIa) and those at moderately susceptible sites that develop slowly, late, or not at all (type IIb). A lesion's position within the vascular tree and thus, the mechanical forces and the nature of the vessel wall at that point, determine, in large part, how a lesion is constituted. The characteristics of early lesions at highly susceptible sites lie in their greater content of lipid and macrophages and in the greater thickness of the intima at these sites.

Type III Lesions

Type III is the intermediate stage between type II and type IV (atheroma, a lesion that is potentially symptom-producing). In addition to the lipid-laden cells of type II, type III lesions contain scattered collections of extracellular lipid droplets and particles that disrupt the coherence of some intimal smooth muscle cells. This extracellular lipid is the immediate precursor of the larger, confluent, and more disruptive core of extracellular lipid that characterizes Type IV lesions.

Referring now to FIG. 3, a photomicrograph of atheroma (type IV lesion) in proximal left anterior descending coronary artery is shown. Extra cellular lipid forms a confluent core in the musculoelastic layer of eccentric adaptive thickening that is always present in this location. The region between the core and the endothelial surface contains macrophages and macrophage foam cells (fc), but an increase in smooth muscle cells or collagenous fibers is not marked. A indicates adventitia; M, media. From a 23-year-old man. Homicide was the cause of death. Fixation by pressure-perfusion with glutaraldehyde. Maraglas embedding. One-micron thick section. Magnification about ×55.

Type IV Lesions

In type IV lesions, the cap still constitutes only preexisting intima, which at highly susceptible artery sites is relatively thick (adaptive intimal thickening). Thus, depending on location in the vascular tree, the thickness of the cap of type IV lesions varies somewhat. However, cap composition is like that of normal intima as shown in FIG. 3. Because in type IV lesions, the lesion cap represents the thickness of the intima at the affected intimal site, it is primarily the amount of lipid that is segregated at the core that determines the degree to which the lumen will be narrowed at this stage of development. In most people, a type IV lesion will not obstruct the lumen much, in part because of the vessel wall's ability, at this stage, for outward expansion. However, when blood lipid levels are very high and a large amount of lipid accumulates quickly, this lesion type, too, may narrow a lumen Type V Lesions Type V lesions, on the other hand, are defined as those in which major parts of the fibromuscular cap represent replacement of tissue disrupted by accumulated lipid and hematoma or organized thrombotic deposits. Cap portions or layers generated by disease and added to the preexisting part have a greater proportion of rough endoplasmic reticulum-rich smooth muscle cells. These cells do not follow the alignments usual of the normal intima (including adaptive thickening), and the caps contain a greater proportion of collagen fibers. The new layers oppose outward expansion of the vessel wall, and narrowing (loss) of the lumen is a prominent feature of type V lesions.

Beginning around the fourth decade of life, lesions that usually have a lipid core may also contain thick layers of fibrous connective tissue (type V lesion) and/or fissure, hematoma, and thrombus (type VI lesion). Some type V lesions are largely calcified (type Vb), and some consist mainly of fibrous connective tissue and little or no accumulated lipid or calcium (type Vc).

Figure 4:
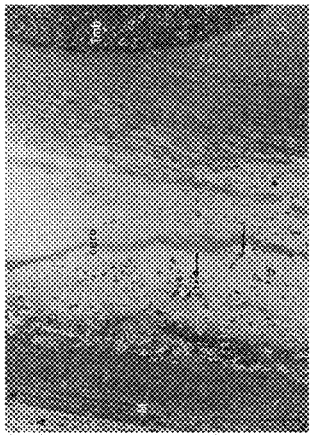
FIG. 4 depicts photomicrograph of type VI lesion in left anterior descending coronary artery about 2 cm distal to main bifurcation.

Referring now to FIG. 4, a photomicrograph of type VI lesion in left anterior descending coronary artery about 2 cm distal to main bifurcation is shown. The type VI lesion is, in this case, formed by a recent thrombus on the surface of a fibroatheroma. The region between the lipid core and thrombus (Tmb) consists of closely layered smooth muscle cells. The lipid core also contains cholesterol crystals and dark staining aggregates of microcrystalline calcium (arrows). A indicates adventitia; M, media. From a 23-year-old man who committed suicide. Fixation by pressure-perfusion with glutaraldehyde. Maraglas embedding. One-micron thick section. Magnification about ×115.

Type VI Lesions

Numerous pathological studies indicate that clinical manifestations and fatal outcomes are most often associated with processes included under the type VI lesion (although even these processes may remain silent) (see FIG. 4). The criteria for the type VI histology include one or more of surface defect, hematoma, and thrombosis. The three processes are often interrelated, although sometimes only one or two are present. For example, a fissure may produce hematoma but little or no superimposed thrombus; occlusive thrombi may form on a surface lacking an apparent defect; ulcerated lesions without much of either hematoma or thrombus may be present.

Figure 5:
FIG. 5 depicts a cross-section of the coronary artery with atherosclerotic plaques.

Referring now to FIG. 5, a cross-section of the coronary artery with an atherosclerotic plaque is shown. There is hemorrhage or thrombosis in the plaque in the middle of this photograph.

TABLE II

| Nomenclature and Main Histology | Sequences in Progress | Main Growth Mechanism | Earliest Onset | Clinical Correlation |
|---|---|---|---|---|
| Type I (initial) lesion isolated macrophage foam cells | I | growth mainly by lipid accumulation | from first decade | clinically silent |
| Type II (fatty streak) lesion mainly intracellular lipid accumulation | II | | | |
| Type III (intermediate) lesion Type II changes & small extracellular lipid pools | III | | from third decade | |
| Type IV (atheroma) lesion Type II changes & core of extracellular lipid | IV | accelerated smooth muscle and collagen increase | | clinically silent or overt |
| Type V (fibroatheroma) lesion lipid core & fibrotic layer, or multiple lipid cores & fibrotic layers, or mainly calcific, or mainly fibrotic | V | | from fourth decade | |
| Type VI (complicated) lesion surface defect, hematoma-hemorrhage, thrombus | VI | thrombosis hematoma | | |

Table II summarizes the sequential progress in the formation of the plaque and also gives the numerical classification on the recommendations of the AHA.

Figures 6A, 6B:
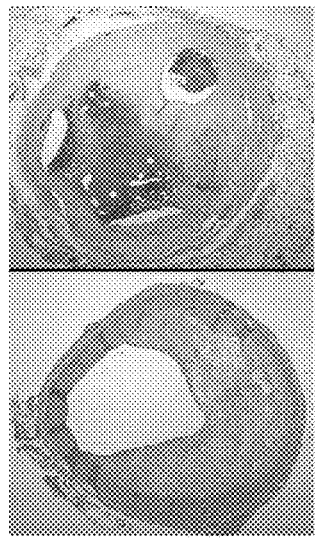
FIGS. 6A&B depict comparative images of type I and type VI lesions.

Referring now to FIGS. 6A&B, comparative images of Type I and Type VI lesions are shown. Referring now to FIG. 7, a coronary artery with atherosclerotic plaques is shown. There is hemorrhage into the plaque in the middle of this photograph. This is one of the complications of atherosclerosis, such hemorrhage could acutely narrow the lumen. Referring now to FIG. 8, a cross-section of the coronary artery with occlusion with slight calcification in the right is shown. Referring now to FIGS. 9A-E, the formation procedure of a plaque along with its numerical classification is shown.

Except for lesion types I through III, which are always small and clinically silent, there is no certain correlation between a lesion's composition and size on one hand and the degree of lumen obstruction and clinical manifestations on the other. Thus, lesion types IV through VI may obstruct the lumen of a medium-size artery to the point of producing a clinical event, even a fatal one, or lesions of the same histologies may exist without significantly obstructing the lumen.

Clinical manifestations may emerge and fatal outcomes occur in the presence of lesions of type IV or V, when these reach a size that is sufficiently obstructive. Lesions at the type IV or type V stage contain a lipid core, but they differ from each other in the derivation and thus, the nature of the fibromuscular layer that faces the lumen above the lipid core, the "cap" of the lesion.

Lesions containing fissures, a small hematoma, and thrombotic deposits are found in young adults. Thus, increases in lesion thickness through processes additional to lipid accumulation begin relatively early in life.

Comparison of post mortem coronary angiograms with histological sections has defined the pathological significance of these morphological descriptors. Histologically advanced lesions with intact lumen surfaces (types IV and V) have smooth borders and regular configurations on postmortem angiography. Lesions with rupture, hemorrhage, hematoma, superimposed partially occluding thrombus (type VI), or organized thrombus have irregular angiographic borders and intraluminal lucencies due to thrombus. Specific characteristics associated with thrombus include intraluminal defects partly surrounded by contrast medium, and contrast pooling at the site of abrupt occlusion. While the hallmark of thrombus is an intraluminal defect, it may contribute to other aspects of the lesion, such as irregular, roughened, or ill-defined borders.

Atherosclerotic lesions result from a variety of pathogenetic processes, including macrophage foam cell formation and death, accumulation of extracellular lipid, displacement and reduction of structural intercellular matrix and smooth muscle cells, generation of mineral deposits, chronic inflammation, neovascularization, disruptions of the lesion surface, and formation and transformation of hematoma and thrombus to fibromuscular tissue. One or the other processes may dominate (or be lacking) in lesion development and progression. Some may continue for the duration of the disease, while others are added at various stages. At later stages of lesion progression, many of the processes may run synchronously.

In the AHA-recommended classification including the updated form, the preferred temporal sequence of typical histological morphologies is denoted with roman numerals. Steps in the development and progression of a disease are normally designated with numerals in medical writing. The AHA Committee had agreed that numerals that stood for strictly defined lesion types were preferable to the continued use of the large variety of traditional terms. To facilitate transition from existing gross pathological nomenclatures to the numerical one, frequently used terms that, though imprecise, seemed closest were appended to the precisely defined roman numerals. Because preferred sequences do exist, the use of consecutive numerals is not only justified but, indeed, mandated.

Classification of Plaque on Visual Basis

The initial lesion or the Type I lesion appears to the unaided eye just as a fatty dot or a streak as shown in FIG. 10. This lesion progresses to the progression-prone Type II lesion, which to the unaided eye still remains a fatty dot, but improves in texture and density. These types of lesions are identified as early lesions, which are shown in FIG. 10 as yellow spots.

Type III lesions, intermediate lesions, Type IV lesions, atheroma lesions, and Type Va lesions, Fibroatheroma lesion, all appear to the unaided eye as atheromatous fibrous plaque. Type Vb lesions appear as calcific lesions and Type Vc lesions appear as fibrotic lesions. Type VI lesions appear to have surface defects and/or hematoma-hemorrhages and/or thrombotic deposits. These legions are called complicated lesions. These are all classified as advanced lesions or raised lesions. These are the classification of plaque, both by a reference standard provided by the AHA and the visual significance of each type as seen with the unaided eye.

Due to the intrinsic heterogeneity of the human plaques, it is not an easy task to distinguish and separate their individual components and/or characteristics, nevertheless non invasive imaging tools can detect and characterize the composition of atherosclerotic plaques. Among those non invasive techniques, magnetic resonance imaging (MRI) provides a reliable characterization methodology for such plaques and also can determine the different elements of the plaque based of biochemical differences.

Very encouraging results were obtained from plaque biochemical analysis that were held to discriminate, decompose and/or discriminate the components of the arterial wall and the atherosclerotic plaque by histomorphology and histochemistry. Seven categories of historical findings of atherosclerotic vessels were considered: (1) loose, edematous, fibrous tissue, (2) dense fibrous cap, (3) smooth muscle cells, (4) lipid, (5) fresh hemorrhage, (6) organization thrombus, and (7) calcification.

The evaluation of the signal properties of plaque are shown in the Table III.

MSCT Characterization of Atherosclerotic Plaque

Next, the inventors show the respective value relation for the MRI and MSCT plaque values. Some plaque composition studies held encouraging characterization results of coronary lesion might be reliably performed by noninvasive MSCT.

TABLE IV

Contrast at CT and MR Imaging of Main Components of Atherosclerotic Plaque

| | Modality (Unit) | | | | |
|---|---|---|---|---|---|
| | CT (HU) | MR (SI*) | | | |
| Sequence | 200** | $T_1W$ | PDW | $T_2W$ | TOF |
| Recent Thrombus | 20 | + to +/− | + to +/− | + to +/− | 0 |
| Lipid | 50 | 1 | 0 | − | +/− |
| Fibrous | 100 | +/− | 0 | +/− to + | +/− to − |
| Calcium | >300 | − | − | − | − |

SI indicates signal intensity; $T_1W$, $T_1$-weighted; $T_2W$, $T_2$-weighted; and PDW, proton-density weighted.
*Relative to adjacent muscle.
**Vessel contrast enhancement.
+ Hyperintense.
+/− Isointense.
− Hypointense.

The heterogeneity composition of the plaque plays a critical roll when it comes it identify it, discriminate it, and therefore to extract its most significant features. This kind of structure also appear in numerous classical problems of signal and image processing; and makes us think how to view the problem of plaque classification and decomposition from a different perspective.

The potential of texture analysis techniques in computer aided diagnostic (CAD) demonstrate the potential of image texture analysis. The present invention relates to the construction of a robust and relievable automated algorithm for plaque identification and decomposition based on its quantitative signature.

In general, the process can be reduced into to main two steps: (1) feature extraction, and (2) feature classification.

TABLE III

MRI Signal Properties of Atherosclerotic Plaque Components

| | Cap | SMC | ORG | Edema | Fresh | Lipid | Calcium | ANOVA |
|---|---|---|---|---|---|---|---|---|
| T1, ms | 419 ± 111 | 588 ± 161 | 464 ± 167 | 419 ± 111 | 467 ± 147 | 300 ± 141 | 625 ± 323 | NS |
| T2, ms | 42 ± 10 | 59 ± 21 | 45 ± 13 | 50 ± 11 | 40 ± 12 | 45 ± 12 | 52 ± 21 | NS |
| INV ratio | 0.62 ± 0.16 | 0.35 ± 0.04 | 0.40 ± 0.10 | 0.25 ± 0.07 | 0.41 ± 0.07 | 0.91 ± 0.06* | 0.28 ± 0.05 | ≤0.001 |
| MTC ratio | 0.62 ± 0.13† | 0.87 ± 0.12 | 0.81 ± 0.06 | 0.87 ± 0.21 | 0.78 ± 0.06 | 0.93 ± 0.14 | 0.85 ± 0.24 | ≤0.0005 |
| GRE ratio | 0.78 ± 0.42 | 0.75 ± 0.12 | 0.66 ± 0.22 | 0.88 ± 0.05 | 101 ± 0.17 | 0.69 ± 0.1 | 0.39 ± 0.21‡ | ≤0.003 |

Values are mean +/− SD. Cap indicates fibrous cap; SMC, smooth muscle cells; ORG, organization thrombus and fresh, fresh thrombus.
*P < 0.05 vs all other components measured by INV.
†P < 0.05 vs all components, except for ORG (P = 0.06) by MTC.
‡P < 0.04 vs all other components measured by GRE-SE.

Referring now to FIG. 11, a color-coded digital parametric image is shown produced by mapping the various histological components of the atherosclerotic endarterectomy cross section at the site of MRI for correlation to the corresponding magnetic resonance images. Regions of fibrous cap, edematous collagen, smooth muscle, lipid, hemorrhage, organizing thrombus, and calcium were color-coded and used to guide localization of ROIs on magnetic resonance images. Blue dense fibrous tissue is similar in composition to the dense fibrous cap, but is external to the lipid component. Fresh hemorrhage is not present in this example.

The selection of textural features is the most challenging part, but in contrast the most promising one. We have developed an accurate and validated method of quantitatively characterizing plaque and to classify their features with different options which vary from rule-based models, the traditional statistical analysis (and often more successful) and artificial intelligence techniques are suitable for the feature extraction part.

Method of Construction of the Invention

The method involves the following steps. First, a template of the heart is constructed to extract region of interest (ROI)

from CT data. The template is used to determine a pose and size of an imaged heart and to formulate a parametric deformable model of the imaged heart. Next, the heart template is registered to an acquired CT data set. From the CT data set, a chest cube and its orientation are determine enclosing the heart. Next, a localized heart coordinate system is created. After the coordinated system is created, a coronary arterial tree template (CAT) with respect to the heart ROIs is constructed and parametric curves along the arteries are formulated and generic cylinders around the artery curves are constructed. Next, the CAT template is registered to heart ROI and the CAT template is fit along inter-ventricular and atrio-ventricular grooves. Next, an aortal template is constructed and a generic cylinder for aorta is created and the template of aorta is registered to heart ROI and the aorta template is fit to aorta ROI.

Heart Template Construction and Region of Interest (ROI) Extraction

Determine the Pose and Size of the Heart

Figure 12:
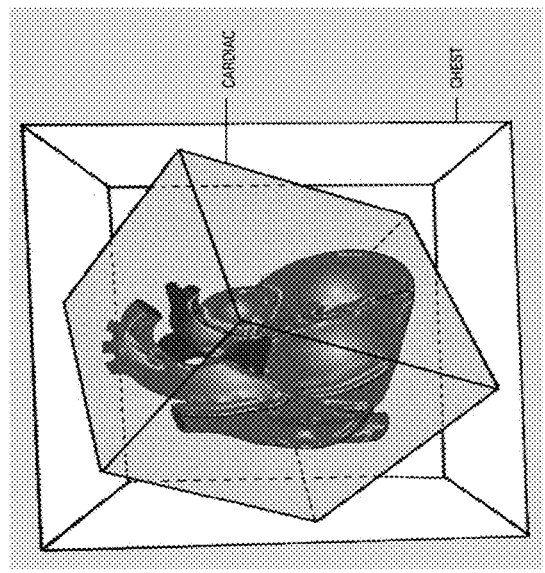
FIG. 12 depicts CT data cubes pertaining to chest and heart.
Figure 14B:
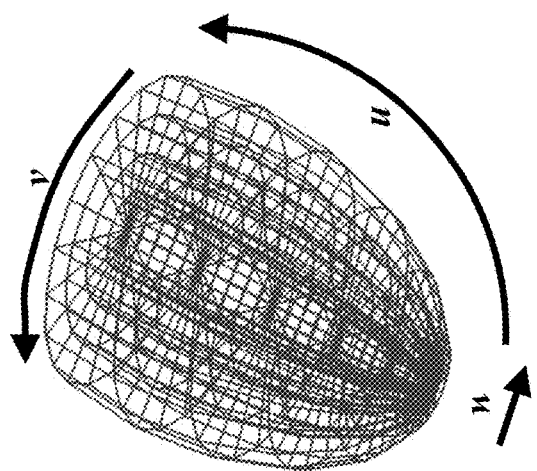
FIGS. 14A&B depicts a parametric model of a semi-ellipsoidal heart template.

The heart is a hollow muscular organ, of conical form, placed obliquely in the chest between the lungs. One can consider the chest as a cube with sides aligned to the three main body planes as shown in FIG. 12. Then, the heart is located in its own cube within the large chest cube. The heart (and the heart cube) is pointing downwards, to the left, and anterior. Usually about 45° in each direction, but there are considerable individual variations.

Figure 13A:
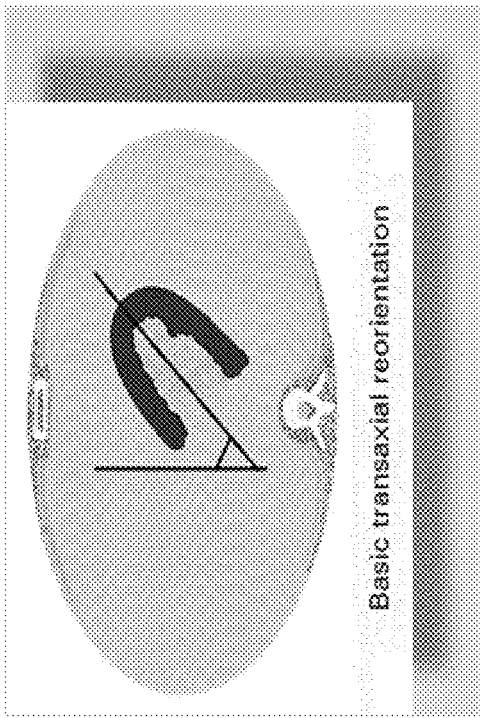
FIGS. 13A&B depict basic trans-axial and sagittal orientation of the heart.
Figure 13B:
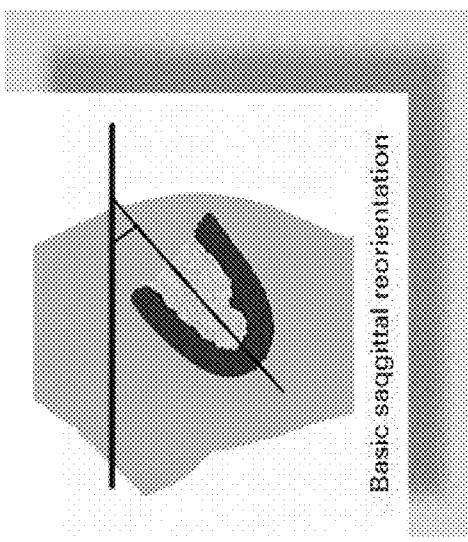

The cardiac CT data is acquired in the transverse body plane i.e., aligned with chest cube. As the heart forms the angle of 45 towards the three main body planes as shown in FIG. 12, the first step towards building the cardiac morphology-centered calcium scoring is the reorientation of the CT data into a heart coordinate system. Referring now to FIGS. 13A&B, basic trans-axial and sagittal orientation of the heart in a heart coordinate system are shown.

Formulate a Parametric Deformable Model of the Heart

Figure 14A:
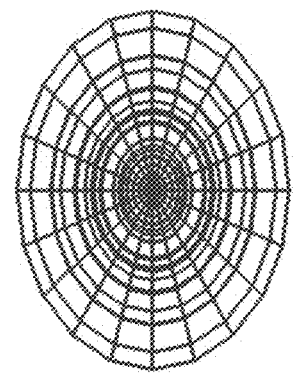

To accommodate for individual variations in heart orientation, the inventors developed a semi-ellipsoidal template for the heart, which can be registered onto the CT data reoriented by 45° to the three main body planes to find the precise orientation of the individual's heart. This template is basically a deformable primitive geometric model of the heart composed of parametric functions of a ellipsoidal solid. The model coordinates (u, v, w) correspond to latitude (u), longitude (v), and radius (w) of the semi-ellipsoidal shape and can be adjusted to acquire a desired shape as shown in FIGS. 14A&B.

Figure 15C:
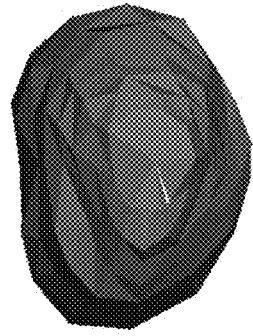
FIGS. 15A-C depict a real heart and a deformed semi-ellipsoidal heart template corresponding to the real heart in two different orientations.
Figure 15B:
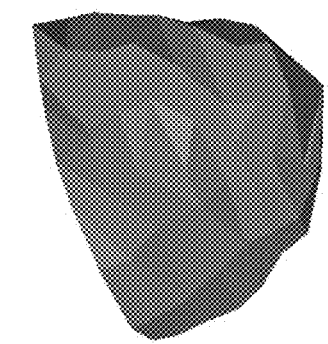
Figure 15A:
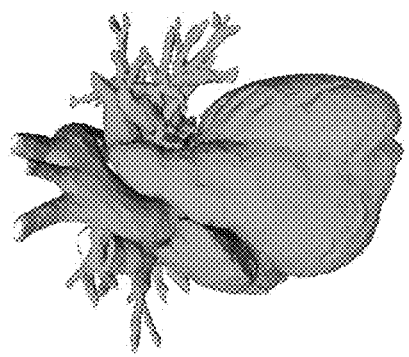
Figure 16A:
FIGS. 16A-D depict LM starts a slice below a pulmonary artery split; left: non-contrast and right: contrast CT.
Figure 16B:
Figure 16C:
Figure 16D:

Further, primitive deformations can be applied to this parametric model to accommodate the template to individual heart morphological variations as shown in FIGS. 15A-C, where a real heart and its corresponding semi-ellipsoidal deformed template is shown in two different orientations.

Register the Heart Template to the CT Data

First, the template of the heart is aligned to the CT data so that registered heart ROIs can be extracted from the data.

Determine the Chest Cube Enclosing the Heart

In the trans-axial slices of the CT, an image of a heart generally begins with the emergence of great cardiac vessels from a base of the heart and ends at a diaphragm near the chest wall.

Manual Detection of the Chest Cube

An upper boundary of the heart in a CT image can be detected using certain rules of thumbs like branching of the wind pipe (appearing as a black circle near the spine) to right and left lung takes place about 4-5 slices above the base of the heart. The more reliable landmark is that the splitting of the pulmanory trunk takes place a slice or two above the base of the heart. Similarly, a lower boundary of the heart can be approximated 4-5 slices below the first appearance of the liver in the CT scan.

Figure 17A:
FIGS. 17A-D depict a beginning of right atrio-ventricular groove indicates start of RCA in the left two figures (non-contrast enhanced, contrast enhanced) and beginning of inter-ventricular groove indicates start of LAD in the right two figures (non-contrast enhanced, contrast enhanced)
Figure 17B:
Figure 17C:
Figure 17D:

The following guidelines can be used to manually determine the CT data belonging to chest cube: (1) a base of the heart, where a left main (LM) starts which can be approximately located just a slice or two below the pulmonary artery split as shown in FIGS. 16A-D: (2) RCA approximate location is roughly the right atrio-ventricular groove as shown in FIGS. 17A-B, (3) LAD approximate location is inter-ventricular groove as shown in FIGS. 17C-D, (4) LCX approximate location is left atrio-ventricular groove as shown in FIGS. 18A-B; and (5) the hearts inferior boundary is reached, when you can see the liver and blood intensity drops down in contrast images as shown in FIGS. 18C-D.

Automatic Detection of the Chest Cube

One can use the same rule of thumbs as used for manual determination of the superior and inferior boundary of the chest cube using a method implemented on a computer. The algorithm start reading in CT slices from the top most slice and detects circular objects in the scan. As the CT acquisition is done with standard protocol, one knows the approximate size of the circles belonging to ascending aorta (AA) and descending aorta (DA) and their position relative to each other. This shape and location information of the aorta is used to detect the trans-axial slice just below the aortic arc, where the aorta splits into AA and DA. The detected AA and DA are tracked in the following slices. The line joining the centroids of ascending and descending aorta intersects the pulmonary trunk, thus we can detect the pulmanory trunk and track it down the trans-axial slices until the slice where pulmonary trunk splits. The slice or two below this one can distinctly identify AA, DA, superior vana cava (just left of AA) and ascending pulmonary artery (APA). This slice marks the superior boundary of the chest cube enclosing the heart cube. We, then, use a slice above this as the upper boundary of chest ROI. The fact that the right atrium (RA) appears below the AA location and the right ventricle (RV) below the APA location are further used in orienting the heart cube and the registration of the heart template. Once inside the heart, we can determine the heart as the biggest detectable ellipse covering the regions of AA, APA. The decreasing ellipsoid of the heart can be tracked using simple region tracking until it ends in an apex. The slice below the slice at which the heart ellipsoid can be tracked is used as the lower boundary of the chest cube. The approximate apex and base (pulmonary split point) serve as axis of orientation for the heart cube in the template alignment step.

Determine the Orientation of the Heart Cube Inside the Chest Cube

One can use the basic cardiac views as a guide to start with trans-axial slices and determine the 3D axes of the left chambers, right chambers, and the atrio-ventricular groove of the heart. Next, the method, implemented as an algorithm encoded as software on a computer, converts the CT data into data oriented in a heart coordinate system. The conversion steps include: (1) determining a right anterior oblique axis (RAO); (2) determining an approximate 4-chamber axis (4CH); (3) determining a short axis of the heart (SH); (4) determining an actual 4-chamber axis (4CH); and (5) determining a heart coordinate system Step 1—Transverse Axis—TRA Select the slice, which clearly shows the septum and the four chambers of the heart. The anatomical landmarks that can be used for determining this slice are: (1) the right atrio-ventricular groove, through which runs the right coronary artery (RCA); (2) the left atrio-ventricular groove, through which runs the left circumflex (LCX) branch; and (3) the right acute marginal coronary artery (some times appears with perceptible visibility).

Step 2—Right Anterior Oblique (RAO)

A plane, whose line of intersection with the slice selected in Step 1 goes through an apex of the LV and is a central axis of the LV, is the plane of projection for 2-chamber long axis view (RAO) of the LV. Form the reformatted data along this axis, select the slice, which clearly shows the central portion of the RV with its 2 chambers. The anatomical landmarks that can be used for determining this slice are: (1) complete RV with superior vana cava and aorta coming out of RA and (2) the right atrio-ventricular groove, wherein runs the right posterior coronary artery as shown in FIG. 19.

Step 3—Approximate 4-Chamber (4CH)

Plane, whose line of intersection with the slice selected in Step 2 goes through apex of the RV and the central axis of RV, is the plane of projection for 4-chamber long axis view (4CH) of the heart. Form the reformatted data along this axis select the basal slice, which clearly shows the AA and DA as shown in FIG. 20. The anatomical landmarks that can be used for determining the slice is: the pulmonary trunk is about to split into two parts. The heart anatomy indicates that, in this orientation RV will be below AA and LV below APA. These two vessels, though coming from exactly opposite ventricles crisscross (are intertwined with) each other.

Step 4—Short Axis (SA)

A plane, whose line of intersection with the slice selected in Step 3 goes through the AA and the APA, is the plane of projection for a short axis (SA) view of the heart. Form the reformatted data along this axis, select the central slice, which clearly shows the circular LV and the semi-lunar RV with septum as shown in FIG. 21. The anatomical landmarks that can be used for determining the slice are: (1) Distinct circular shape of LV; and (2) Couple of slices below both left and right atrio-ventricular grooves, through which, the RCA and LCX Run Step 5—Actual 4-Chamber (4CH)

A plane, whose line of intersection with the slice selected in Step 4 goes through center of the LV and midpoint of the septum (or about 2 cm from inter-ventricular groove), is the plane of projection for 4-chamber (4CH) view of the heart as shown in FIG. 22. Form the reformatted data along this axis, select the central slice, which clearly shows septum and the 4 chambers of the heart. The anatomical landmarks that can be used for determining the slice are: (1) The mitral valve in LV; (2) The right atrio-ventricular groove along which runs the right coronary artery (RCA); (3) The left atrio-ventricular groove along which runs the left circumflex (LCX) branch; and (4) The right acute marginal coronary artery (some times appears with perceptible visibility).

Determination of the Cardiac Coordinate System

Figure 23:
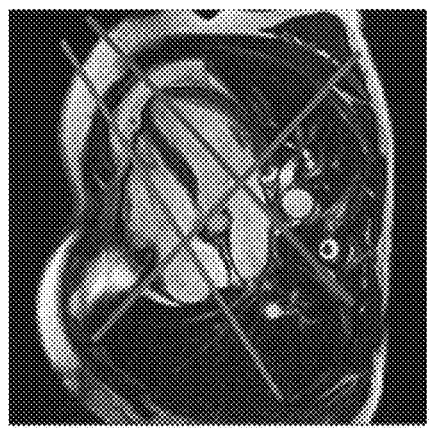
Figure 24D:
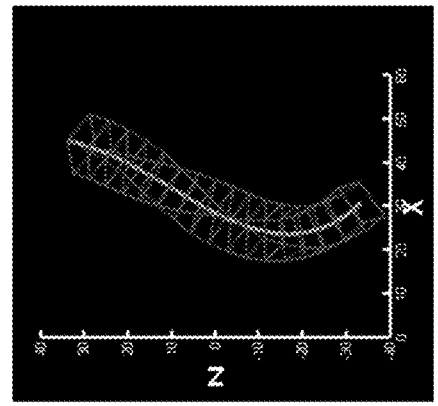
FIGS. 24A-D depict a parametric generalized cylinder pertaining to LAD.
Figure 24C:
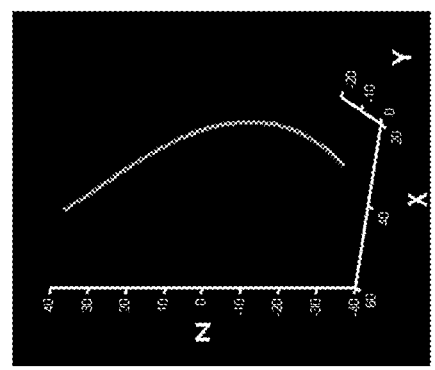
Figure 24B:
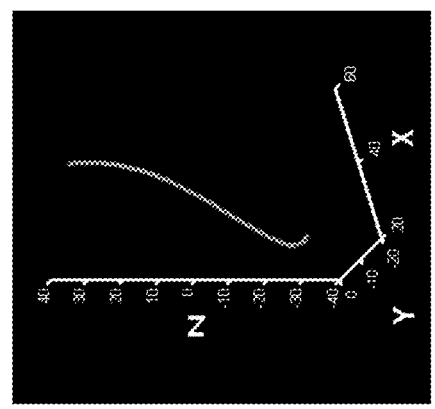
Figure 24A:
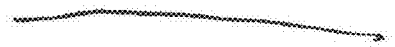

At the end of Step 5, we have locked on to the anatomical bases of the heart coordinate system as shown in FIG. 23. The basis planes of the heart are: (1) the plane of projection obtained from Step 5, which gives 4-chamber long axis view; (2) the Plane, whose line of intersection with the plane of projection of Step 5 goes along the inter-ventricular septum, giving 2-chamber long axis view; (3) the plane, whose line of intersection with the plane of projection of Step 5 goes through the mitral and tricuspid valves (i.e., left and right atrio-ventricular grooves) giving the short axis view of the heart.

This cardiac morphology-centered coordinate axes allow us to orient the semi-ellipsoidal template of the heart. The affine transformations are performed on this template to accommodate individual variations. The primitive deformation of the template guided by the heart surface gives the accurate cardiac surface to extract the heart volume ROI, from the CT data.

Construct a Template of Coronary Arterial Tree (Cat) Relative to Heart ROIs

Formulate Parametric Curves Along the Arteries

Figure 25B:
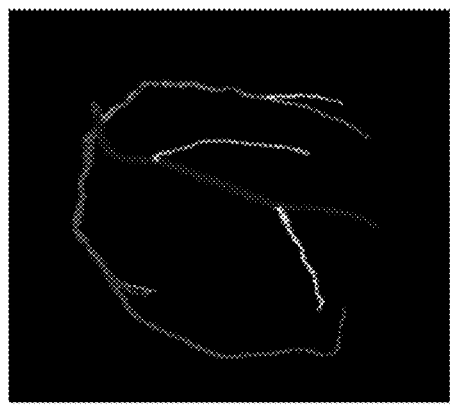
FIGS. 25A&B depicts a schematic diagram depicting coronary artery template.
Figure 25A:
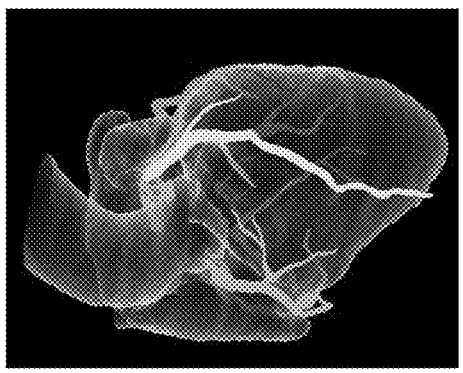

The deformed template after fitting to the CT data provides the inter-ventricular and atrio-ventricular grooves in 3D. A parametric polynomial is fit (e.g. f(u) for LAD) following the curved path of these grooves which basically are the paths of the LAD, LCX, and RCA as shown in FIGS. 25A&B.

Formulate Generic Cylinders Around the Artery Curves

Once the central axis of the coronary arteries is modeled, frenet frames can be used to find out the orientation of cross sections at different points along the artery to model generic cylinder pertaining to each coronary artery as shown in FIGS. 24A-D. Thus we can generate set of parametric tubes corresponding to CAT. One can set the radius of these tubes high enough to accommodate for the individual curvature variations.

Register the Cat Template to Heart ROI

Fit the Cat Template Along Inter-Ventricular and Atrio-Ventricular Grooves

The CAT template modeled as generic cylinders can be further refined by fitting it to the patient specific heart template for accuracy. The CAT ROIs are then extracted using this fitted CAT template for further analysis of calcium distribution along the coronary arteries.

Construct a Template of Aorta

Formulate a Generic Cylinder for Aorta

Figure 26A:
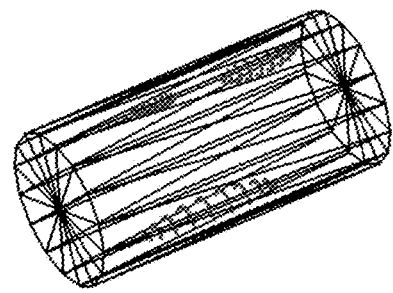
FIGS. 26A-C depicts a schematic diagram showing analysis of calcium distribution in the artery in parametric space.
Figure 26C:
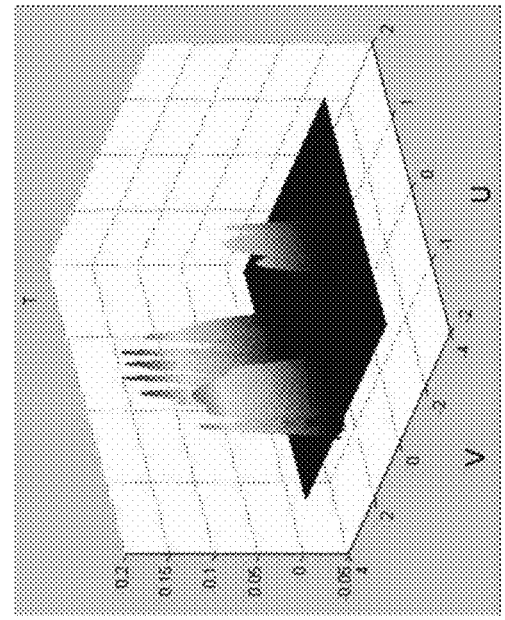
Figure 26B:
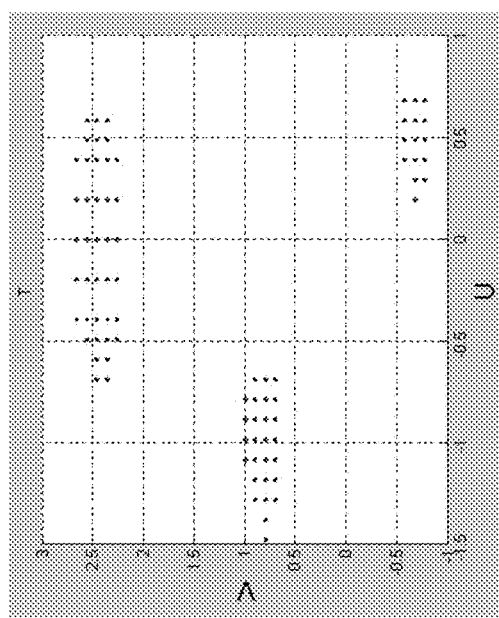

In general, the parametric generic cylinder model for artery can be used for other arteries e.g. aorta to report spatial distribution of calcification. As the generic tubes pertaining to arteries are represented parametrically we can report them on parametric space for more accurate analysis of calcifications as shown in FIGS. 26A-C.

Register the Aorta Template to Aorta ROI

Fit the Aorta Template to Aorta ROI

The aorta is tracked as circular object in trans-axial slices the edge information from this segmentation is used to register generic cylinder to the aorta.

The present invention also relates to a method for optimizing a generalized risk factor or to generate specialized risk factors for different groups of patients. The optimizing process basically involves varying the risk components and weights associated therewith until an optimized risk factor or risk rating system is developed.

Functional Morphology Analysis of the Left Anterior Descending Coronary Artery in EBCT Images In this section, the inventors present a novel method for the quantification of functional morphology parameters of the Left Anterior Descending (LAD) coronary artery, using a physics-based deformable model framework with the long-axis of the heart as the local frame of reference. The shape of the LAD is modeled as a parametric curve with an associated Frenet-Serret frame. The motion of the LAD during the heart cycle is modeled as a composite of three motion components with respect to the heart's local frame of reference: 1) longitudinal displacement, 2) radial displacement, and 3) angular displacement. These components are parameterized along the LAD's length. Results from asymptomatic subjects' Electron Beam Computed Tomography (EBCT) data and simulated data are in agreement with the expected physiological trends and suggest a clinical relation between the LAD dynamics and the anterior left ventricle (LV) dynamics.

I. Introduction

The significant increase in spatio-temporal resolution of Electron Beam Computed Tomography (EBCT) and Magnetic Resonance (MR) imaging has made it possible to acquire high-resolution volumetric cardiac image data over the cardiac cycle, thus enabling computer-assisted physiological analysis of the heart for monitoring, prognosis, diagnosis, and treatment planning [1]. Those advances in non-invasive medical imaging, open the possibility to asses a quantitative analysis of the volume, shape, deformation, and motion of the heart towards to differentiate between healthy and unhealthy hearts. The motion and deformation of the heart can be analyzed either by tracking the myocardium or by tracking various kinds of landmarks (anatomically, implanted, or induced). Furthermore, the complexity of the left ventricle's (LV) non-rigid motion and the lack of reference landmarks within the myocardium make it difficult to extract the true motion trajectories from sequential images.

Figure 27:
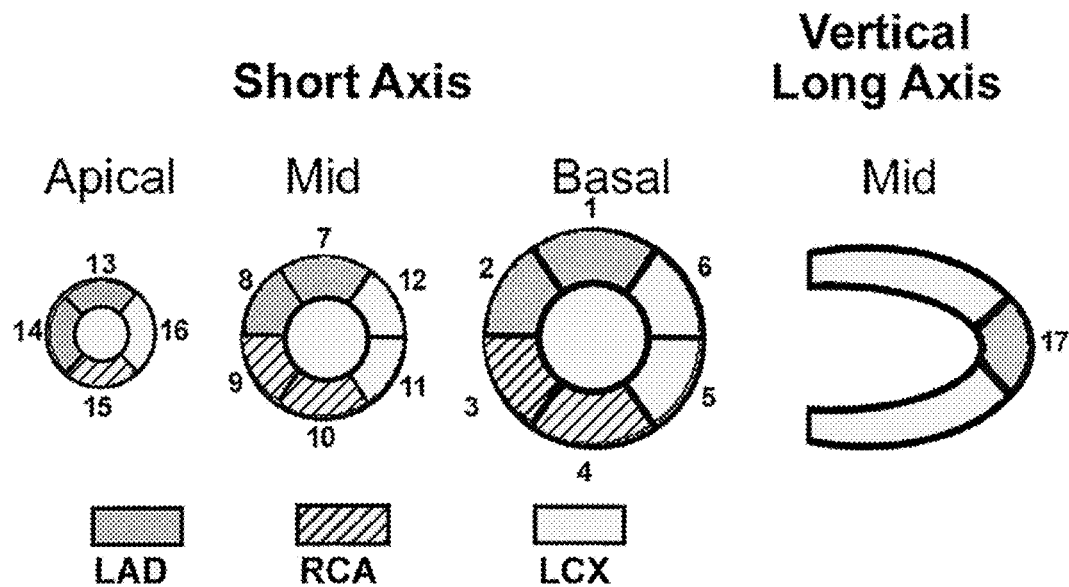
FIG. 27 depicts a schematic of the coronary territory as described in Cerqueria.

In order to compare EBCT coronary angiography versus conventional Cine coronary angiography, a number of studies have been performed [2], [3], [4], [5]. EBCT permitted the visualization of the proximal and mid coronary arteries in 80% of the cases. The left main coronary artery and proximal and middle parts of the left anterior descending (LAD) could generally be visualized and assessed from 90% to 100% of the cases, with a sensitivity to detect stenosis from 85% to 90% and specificity of 90%, while images of the right and circumflex coronary artery (RCA) and (LCX) were well identified in 75% of cases. Cardiac motion introduced imaging artifacts in 20% of the cases, prominently in small artery segments of the RCA and LCX. The LAD, which is attached to the myocardium, can be used as a natural landmark to partially track the anterior—septal myocardial motion, see FIG. 27. Since both shape (curvature, length, and cross-sectional contours) and motion (magnitude and direction) are nonuniform along the length of the LAD, a shape-motion parameterization is desirable to express such non-rigid deformations over time. The spiral orientation of the LV fibers (along the long axis of the heart) is the motivation to define the three dimensional (3D) shape-motion parameters for the LAD. Such parameters may be computed by taking into consideration: i) longitudinal, ii) radial, and iii) angular displacement, imparted by the myocardial motion onto the LAD with respect to the long axis of the heart.

The functional morphology of anatomical structures can be analyzed by locking onto and tracking geometrical or anatomical landmarks to establish a physical correspondence of those landmarks over time. Parametric deformable templates for anatomical structures have proven to be efficient for locking onto significant physical landmarks, allowing tracking over time to perform shape and motion analysis. An example of a diagnostically relevant shape feature can be found in Ilia [7], in which is stated not only the anatomically importance of the length of the LAD but also its importance in diagnosing coronary artery lesions. Furthermore, functional morphological analysis can help diagnose specific pathologies by characterizing the shape and motion of healthy versus unhealthy organs. However, the deformable template-based shape and motion estimation of anatomical structures poses challenges of its own.

Shape-specific features of anatomical structures are constructed from particular properties of the anatomical element, whereas motion-specific features are the total/partial result of the interaction of such shape properties, i.e. they are interdependent with: i) physically connected, and ii) geometrically related anatomical structures. See Chen [8], as an example 3D vascular-shape quantification. In addition, the shape-specific geometric features themselves vary depending on the position along a certain dimension of the object (e.g., the radius, curvature and torsion of an elastic blood vessel all vary along its length). Thus, the model of the shape of an anatomical object needs to be parametric along dominant geometric dimensions to effectively capture changes in its geometric features. From a motion analysis stand point, a linear assignment of corresponding points through time to compute motion is impossible in practice, as the anatomical elements undergo global shape changes which may not be uniform along the direction of parameterization. Furthermore, an anatomical object's resultant motion is generally composed of self-motion (local) and imparted global motion (e.g., respiratory and diaphragmatic motions imparted on heart motion, which in turn is imparted on coronary arteries). Thus, a comprehensive motion model will not only be parametric but will also take into consideration the global shape changes imparted by the various components of motion of physically-connected anatomical structures.

The challenges towards the development of a computational framework for four-dimensional functional morphology analysis of the LAD can be summarized as the following:

1) Representing the non-rigid shape and motion of the LAD:
   (a) Constraining the deformations and displacements to the local inertial frame of reference, and
   (b) Establishing point to point correspondence over the cardiac cycle.
2) Capturing clinically related shape features of the LAD:
   (a) Lumen contour (or radius) and curvature of the LAD along its length over the cardiac cycle, and
   (b) Characterizing the LAD deformations from the base to apex of the heart (e.g. the LAD's contraction/expansion respect to the long axis of the heart over the cardiac cycle).
3) Capturing the motion components imparted by the myocardium on the LAD.

This section discusses the clinical relation of the LAD deformation with the anterior LV motion over the cardiac cycle. A functional analysis for the LAD is performed by parameterizing its shape and motion over time by a physics-based deformable model framework [9], [10]. Our main contribution is that our framework incorporates three basic motion components that naturally describe the deformation of the LAD w.r.t. a local coordinate system for the heart.

The key contributions within the proposed computational framework towards the 3D shape-motion analysis of the LAD are:

1) Parametric shape modeling is achieved through:
   (a) Defining a local coordinate system for the heart, and
   (b) Employing a Frenet-Serret (FS) frame-based parametric geometric primitive.
2) Parametric motion modeling is achieved through:
   (a) Modeling the LAD motion as a composite of primitive motion parameters, and
   (b) Using frame by frame fitting of a deformable model.

This section is organized as follows: In Section II we compare our approach to track the LAD with existing coronary artery tracking methods. In Section III we introduce the general deformable model framework, as well as the specific framework adaptation to track the LAD. In Section IV we present the results obtained from simulated and EBCT angiography data, and finally in Sections V and VI we present our discussion and conclusion.

II. Related Work

Previous approaches towards tracking of coronary arteries can broadly be classified as: 1) landmark-based (Kong et. al [11], Potel et. al [12], Stevenson et. al [13]), 2) template-based (Ding et. al [14]), and 3) geometric constraint-based (Chen et. al [15], Olszewski et. al [16], Liao et. al [17], Mourges et. al [18]). Early studies of coronary arterial motion were intended for evaluation of regional myocardial performance. Kong et al. [11] made the initial effort towards 4D analysis of coronary arteries by using the bifurcation points of coronary arteries as landmarks to track the artery over time for motion analysis. Potel et al. [12] used biplane cineangiograms to derive the 3D motion of bifurcation points. This technique was further improved by Stevenson et al. [13] by incorporating a cross-correlation method, which automatically performed frame-to-frame tracking of corresponding points. Most of these early studies employed a limited number of feature points on the coronary arterial tree, and therefore provided descriptions of the motion at only selected points.

With the growing interest in the biomechanical implications of coronary arterial motion in vascular disease, there is a greater need for motion analysis of an entire vessel segment. However, as the motion of the coronary arteries is non-uniform (i.e., the magnitude and direction of vessel motion, and axial strain, vary along the length of the vessel), quantifying the motion of a vessel segment in a point-by-point manner presents a nontrivial challenge. Gross and Friedman [19] made an effort to characterize the motion of an entire vessel segment, but uniform strain along the length of the segment was assumed. Ruan [20] proposed an iterative method (prediction-projection) for coronary artery motion based on kinetic features by incorporating motion smoothness constrains. Shechter [21], reported a 3D method for tracking the coronary arteries from a temporal sequence of biplane X-ray angiography images. The method relies in artery centerline reconstruction from a biplane image pair at one time frame. Movassaghi [22], introduces a method for 3D coronary modeling based on the 3D centerline point position and the 3D cross sectional artery area. Another system was proposed by Zhaouha and Friedman [23], for quantification of 3D coronary arterial motion using clinical biplane coronary cineangiograms, where a template matching technique was used to track the frame-to-frame motion of coronary arteries without making assumptions about the uniformity of axial vessel strain. However, these systems do not accommodate for radial displacement and axial torsion as these parameters cannot be derived from vessel axis dynamics alone. A more recent method for quantifying the dynamic geometry of coronary arteries using Frenet-Serret (FS) curvature analysis is reported by Liao et al. [17]. This work assesses changes in curvature, torsion, and discrete flexion points by analyzing only the end-diastolic (ED) and end-systolic (ES) phases. However, these parameters are estimated in the coronary artery's local frame of reference and do not extract global changes in arterial geometry with respect to the heart's coordinate system. Blondel [24], [25] developed a method to perform 3D tomographic reconstruction of the coronary arteries from a cone beam. However, the method requires the pre-computation of the artery motion field.

III. Methods

The functional morphology analysis of a non-rigid object poses challenges in terms of establishing point-to-point correspondences in space and time. In addition, is desirable to integrate a shape and motion into a common framework. Shape modeling should be based in intuitive descriptors [26], while motion modeling should account for general motion primitives to allow a broad number of degrees of freedom to account for non-rigid deformations.

To that effect, we propose a physics-based deformable model for the LAD, by taking into account:
  1) An anatomically frame of reference,
  2) Shape-motion parametrization in space and time, and
  3) A decomposition of the overall LAD dynamics to capture the interdependence of anatomical elements.

In this Section, we provide a brief description of the deformable model framework [27], [28], and its adaptation to the shape-motion analysis of the LAD.

A. Formulation of Parametric Deformable Models

Figure 28:
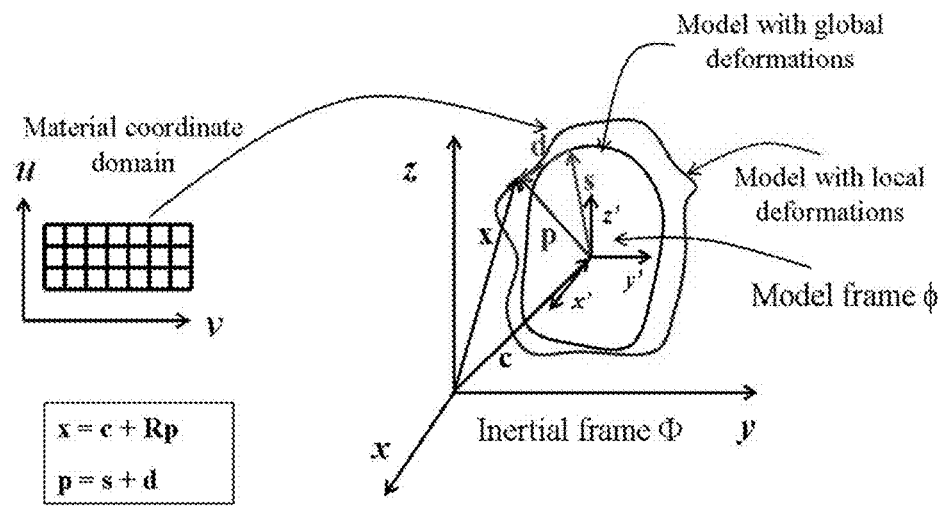
FIG. 28 depicts a schematic of the deformable model framework.

Parametric deformable models can describe an object's shape and motion based on a few number of parameters (these parameters are intrinsic to the shape and motion of the object). The class of deformable models described in this Section refers to 3D models defined by a surface with material coordinates u=(u,v), defined over a domain $\Omega$. The position of the points on the model relative to an inertial frame of reference $\Phi$ in space are given by a vector valued, time varying function of u:

$$x(u,t)=(x_1(u,t),x_2(u,t),x_3(u,t))^T \quad (1)$$

where $^T$ denotes matrix transposition. A non-inertial, model-centered reference frame 4 is set up and the function describing the position in space is expressed as:

$$x=c+Rp \quad (2)$$

where c(t) is the origin of $\varphi$ at the center of the model and the rotation matrix R(t) gives the orientation of $\varphi$ relative to $\Phi$. The general framework is depicted in FIG. 28. Thus, p(u,t) gives the positions of points on the model relative to the model frame [27], [29].

To incorporate global and local deformations, p is expressed as the sum of a global reference shape s(u,t) and a local displacement function d(u,t):

$$p=s+d \quad (3)$$

The global reference shape s is defined as a composition of a geometric primitive e with a deformation function T:

$$s(u,t)=(T \cdot e)(u,t)=T(e(u);\beta_0(u,t),\beta_1(u,t),\ldots) \quad (4)$$

where the geometric primitive e can be defined as: i) a set of 3D points in space or ii) a parametric function e(u; $\alpha_0(u)$, $\alpha_1(u), \ldots$), with parametric functions a, (u). In general e and T are not linear functions. When e is defined by parametric functions, it can be assumed that e and T are both differentiable with respect to u.

The motion (deformations) T, are defined as a composite sequence of basic parametric deformations $T_i$, as follows:

$$T(e)=(T_1 \cdot T_2 \cdot \ldots \cdot T_n)(e) \quad (5)$$

Therefore, the parameters for the global reference shape and motion ($\alpha_i(u)$, and $\beta_i(u,t)$), can be concatenated into a vector $q_s$:

$$q_s = (\alpha_0(u), \alpha_1(u), \ldots, \beta_0(u,t), \beta_1(u,t), \ldots) \tag{6}$$

The shape and motion parameters, $\alpha_i(u)$ and $\beta_i(u,t)$ respectively, define a set of geometric primitives and parametric deformations which can be integrated into a general framework for shape and motion estimation.

Local deformations d can be expressed as:

$$d = S q_d \tag{7}$$

where S is a shape matrix defined by shape functions, and $q_d = (\ldots, d_i^T, \ldots)^T$ is the vector of local deformation parameters. See Metaxas [29], for details.

In the next Section, we will describe the proposed parametric deformable model for the LAD. The shape and motion for the LAD is modeled by: i) incorporating a parametric generalized cylinder (the geometric primitive), and ii) parameterizing the LAD motion over time (respect to an anatomically frame of reference).

B. Anatomically Model-Centered Frame of Reference

Figure 29A:
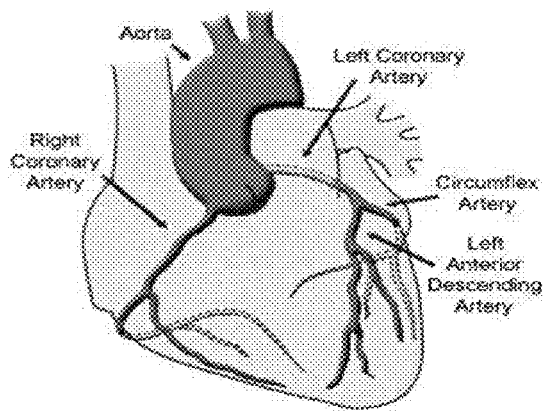
FIGS. 29A-C depicts a schematic of coronary arteries and the orientation of the local coordinate system φ respect to the heart. (A) An illustration of the anatomy of the coronary arteries respect to the heart. (B) An axial EBCT slice of the chest, depicting a basic trans-axial heart re-orientation in the heart. (C) A volume rendering of the heart, with its corresponding global and local heart coordinate system.

The definition of an object's own local coordinate system, effectively capturing its shape and motion specific features is essential for the analysis of the shape, motion, and deformation of such object. Thus, determining a reference frame (coordinate system) for the heart itself is important in establishing the topological relationship between the heart and the coronary arteries. Furthermore, a local coordinate system could describe coronary artery motion in terms of components relative to the myocardial wall. FIG. 29A depicts the position of the coronary arteries respect to the heart.

Figure 29B:
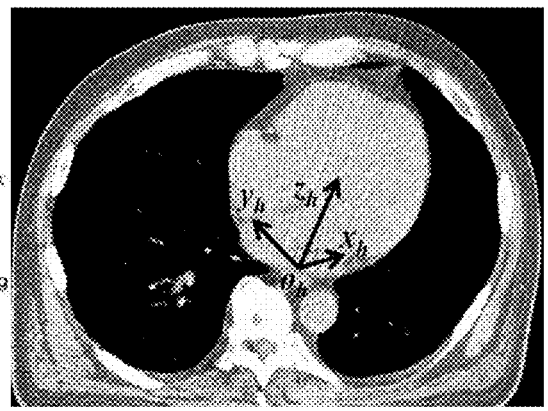
Figure 29C:
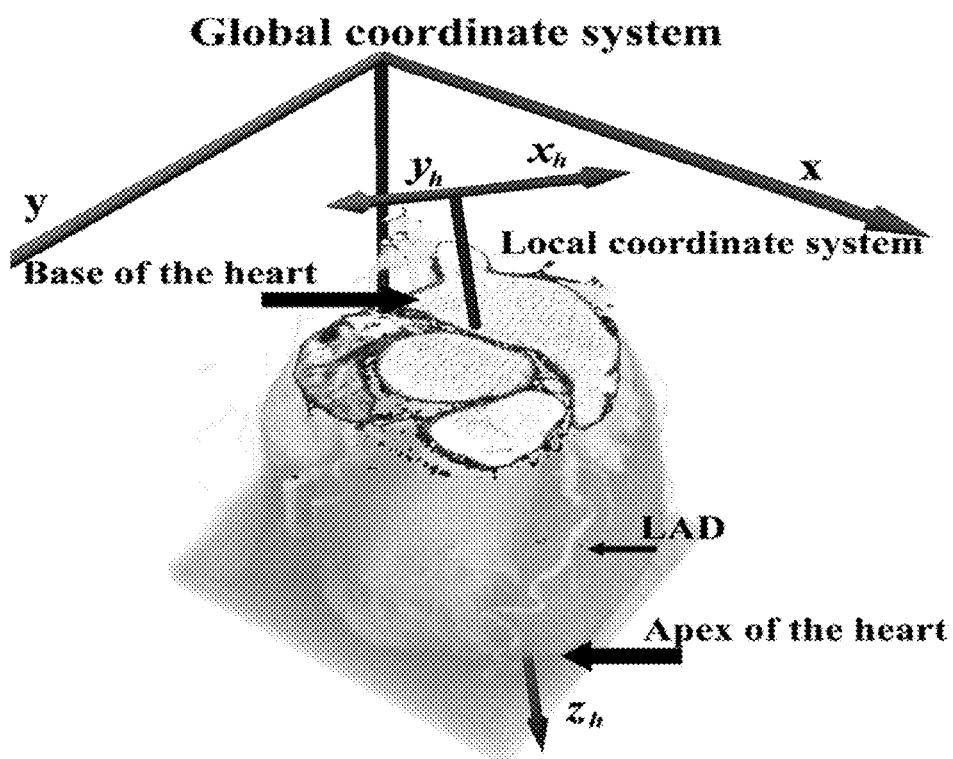

The heart is situated obliquely in the chest, with considerable individual variations. In general, the conically shaped heart points downwards, to the left and anterior, with its major axis forming an angle of approximately 45° with the three main body planes (transverse, sagittal, and coronal). By taking into account the heart orientation, we define a local coordinate system for the heart FIGS. 29B&C:

Definition 1 (Heart Coordinate System)

We say that the coordinate system 4, (consisting of the origin c, and $x_h$, $y_h$, $z_h$ axis) is a local coordinate system for the heart if the following conditions hold:

1) The origin c for $\varphi$ is located at the center of the base of the heart, 2) The $z_h$ axis points from c (the base of the heart) towards the appex of the heart, 3) The $y_h$ axis points from c towards the right coronary artery, and 4) The $x_h$ axis points from c towards the left circumflex artery.

Without loss of generality, we constrain $\varphi$ to be a local coordinate system for the heart, and therefore p (Eq. 3), expresses the points of the LAD model respect to the heart itself. In the rest of this section, it is assumed that 4 is a local coordinate system for the heart according to Def. 1.

C. Parametric Shape-Motion Modeling of the LAD

We present our parametric shape-motion model for the LAD. Since in the physics-based deformable model formulation, the shape-motion vector s, (Eq. 4) depends of: i) local deformations d, which can be thought of deformation parameters used to reconstruct fine details, and ii) a global reference shape e which is defined by a family of parametric functions that capture local variations in shape. Local deformations d are constrained to play no roll when modeling the LAD shape, i.e. the LAD surface is assumed to be a smooth surface by setting the parameters $\beta_i$ to zero. And therefore the LAD model p from Eq. 3 is simplified to:

$$p = s \tag{8}$$

Therefore the LAD is geometrically constructed as a generalized cylinder, a tube-shaped deformable model with a parametric differentiable curve as its spine. Parameterized using the intrinsic notion of a Frenet-Serret frame (FS).

To model the medial axis of the LAD, we define a differentiable parametric curve $l(u): \mathbb{R} \to \mathbb{R}^3$, as a polynomial curve in the 3D space. Without loss of generality, to model the medial axis of the LAD, the parametric curved spine l(u) is expressed as a 9th order polynomial. The degree of the polynomial was selected in order to capture and initialize the global shape of the medial axis of the LAD. A finer fitting is accomplished by deforming the model.

Given a differentiable curve l(u), a FS frame at a given point of I(u) is a vector field consisting of a triplet of vectors $(T(u); B(u); N(u))^T$. The FS frame constitutes an orthogonal system of vectors, and such orthogonal system is obtained from the curve's derivatives I with respect to the parameter u. The first derivative, 1(u), is the vector in the direction of the tangent to the curve at point I(u). The first ($\dot{l}(u)$) and second ($\ddot{l}(u)$) derivatives define the osculating plane of the curve at that point—the limit of all the planes defined by the point Il(u) and the ends of the infinitesimal arcs of the curve near it [30]. These two vectors are not always orthogonal to each other, but they can be used to define the binormal vector, the vector perpendicular to the osculating plane. The binormal and tangent vectors, in turn, define the normal vector and with it an orthogonal system of axes that constitutes the FS frame at the point l(u):

$$\text{Tangent } T(u) = \frac{\dot{l}(u)}{|\dot{l}(u)|} \tag{9}$$

$$\text{Binormal } B(u) = \frac{\dot{l}(u) \times \ddot{l}(u)}{|\dot{l}(u) \times \ddot{l}(u)|}, \text{ and}$$

$$\text{Normal } N(u) = B(u) \times T(u)$$

This frame is independent of the curve's coordinate system, and the parametrization depends only on its local shape [31].

The geometric model e of the LAD, is a tube-shaped deformable model with a parametric curve I(u) as its spine, and FS frame oriented cross sectional planes a(u,v):

$$e(u,v) = \begin{bmatrix} l_1(u) + a_1(u,v) \\ l_2(u) + a_2(u,v) \\ l_3(u) + a_3(u,v) \end{bmatrix} \tag{10}$$

where $$-\frac{\pi}{2} \le u \le \frac{\pi}{2}, -\pi \le v \le \pi$$

and the cross sectional planes can be represented in a matrix form as follows:

$$\begin{bmatrix} a_1(u,v) \\ a_2(u,v) \\ a_3(u,v) \end{bmatrix} = r(u) \begin{bmatrix} N_1(u) & B_1(u) \\ N_2(u) & B_2(u) \\ N_3(u) & B_3(u) \end{bmatrix} \begin{bmatrix} \cos(v) \\ \sin(v) \end{bmatrix} \tag{11}$$

where, $l(u)=(l_1(u), l_2(u), l_3(u))^T$, $a(u,v)=a_1(u,v)=(a_2(u,v), a_3(u, v)^T$, and $r(u)$ is defined as the radius of the artery cross-section.

Figure 30A:
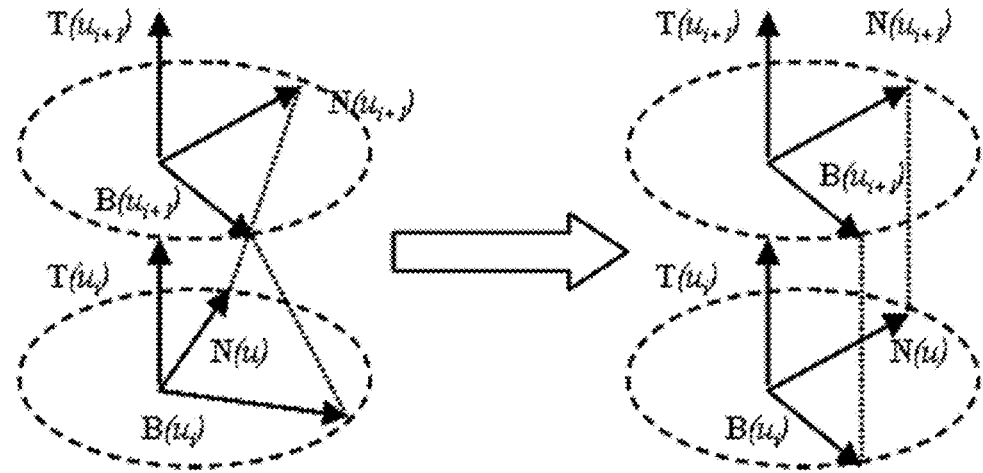
FIGS. 30A&B depict Construction of the deformable generalized cylinder (A) Rotation of each frame respect its center of gravity, and (B) To the left: the medial axis of the LAD with the Frenet-Serret frames: tangent T, normal N, and binormal B vectors, along a parametric 3D curve. To the right: the shape primitive e, depicting the cross sectional points along the LAD.
Figure 30B:
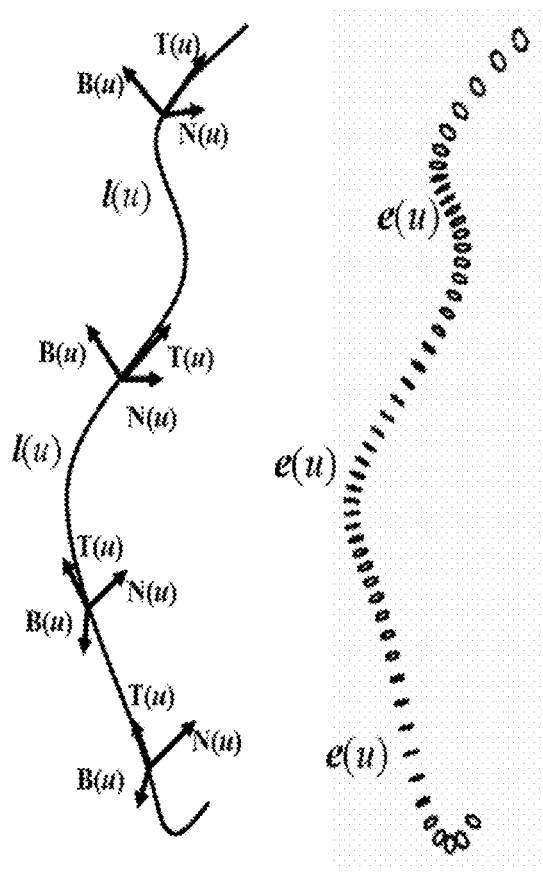

The FS frame is used to capture the shape of the LAD along the medial axis since it provides a local frame of reference uniquely determined by a point on a curve and the curve's behavior around this point. Since the trajectory of the medial axis 1 includes segments of high curvature, and since each FS frame depends only of local properties of the curve, a rotational effect from frame to frame may be present (respect to the tangent vector), specially when abrupt changes in curvature occur. The LAD shape is invariant under this rotational effect, since each cross sectional circle rotates respect to its center of gravity. However, in order to define a rotational-invariant mesh for the LAD, the cross sectional planes $a(u,v)$ are re-oriented along u by rotating (respect to the tangent T) the normal and binormal vectors, N, and B. The FS frames re-orientation is performed by finding the minimum distance between consecutive binormal vectors $B(u_k)$ and $B(u_{k+1})$, (see FIG. 30A). FIG. 30B depicts an illustration of the FS frames of a curve $l(u)$ for various values of the parameter u, as well as the cross-sectional sections of the LAD for the generalized cylinder e.

Figure 31A:
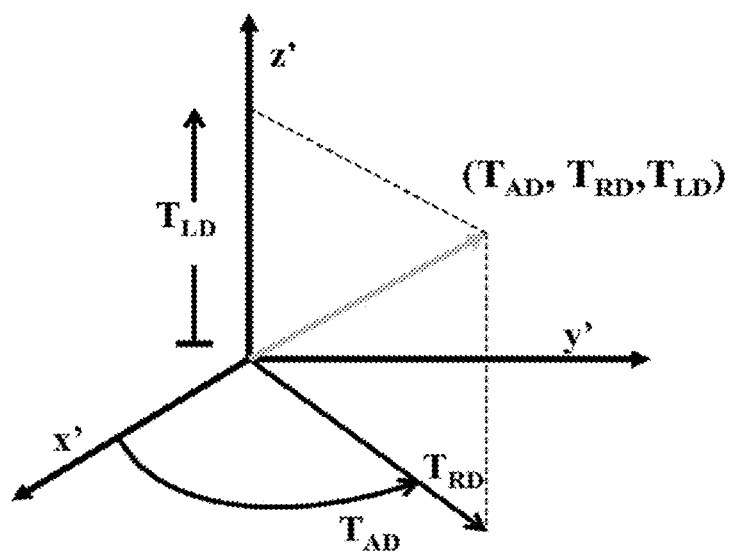
FIGS. 31A-E depict shape motion parameters for the LAD with possible variations over time, (A) Basic degrees of freedom for $T_{RD}$, $T_{AD}$, and $T_{LD}$, (B) The generalized cylinder s at two different time steps $t_k$ and $t_{k+1}$, (C) Radial displacement $T_{RD}$, radial expansion at time $t_{k+1}$ and contraction at time $t_{k+1}$ respect to the long axis of the heart, (D) Longitudinal displacement $T_{LD}$, expansion and contraction at time $t_{k+1}$, and (E) Angular displacement $T_{AD}$, anti-clockwise and clockwise at time $t_{k+1}$.
Figure 31B:
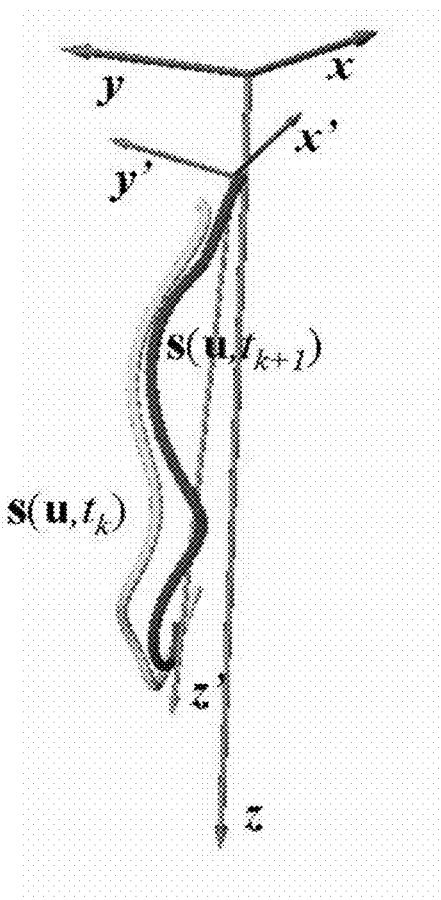
Figure 31C:
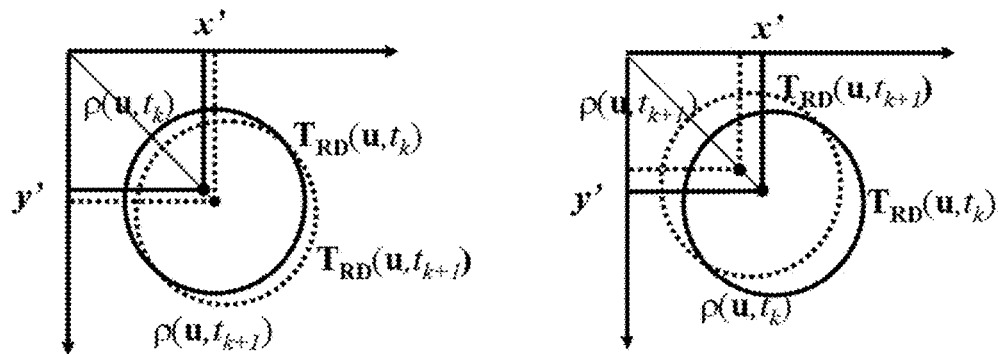
Figure 31D:
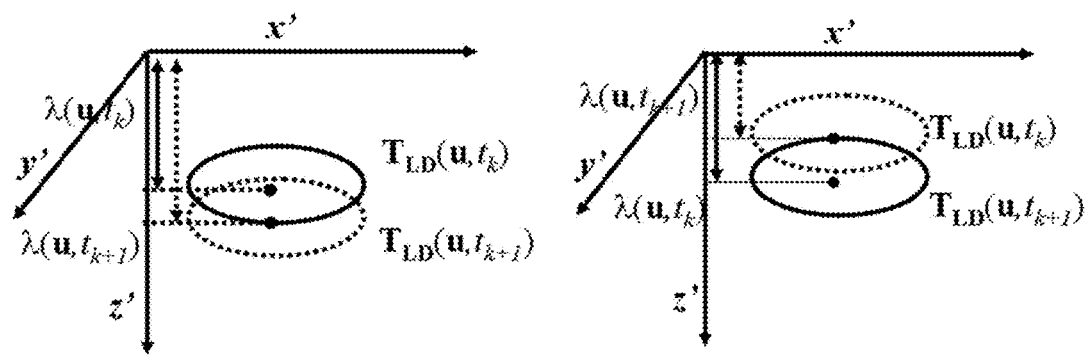
Figure 31E:
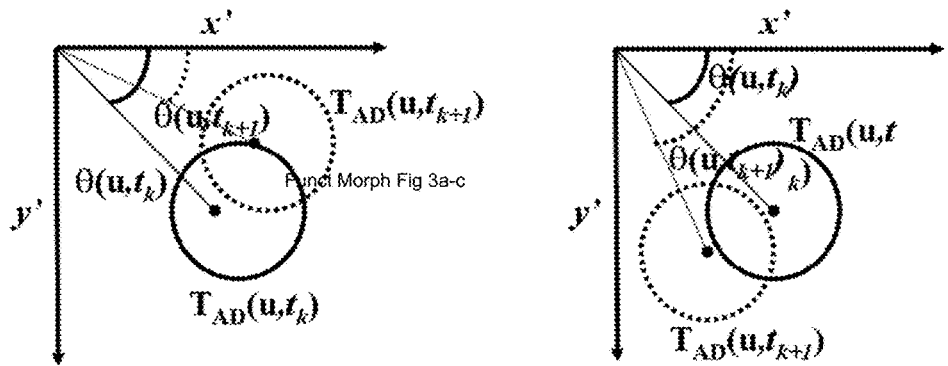

The motion T of the LAD owing to heart itself, is modeled as a sequential composition of primitive shape-motion transforms $T_{AD}$, $T_{RD}$, and $T_{LD}$ (FIGS. 31A&B), where:
1) $T_{LD}$ is longitudinal displacement along the long axis of the heart—this measures displacement along the long-axis of the heart, which is the z'-axis in the local coordinate frame of the heart, FIG. 31C;
2) $T_{RD}$ is radial displacement perpendicular to the long axis of the heart—this measures displacement on the plane cross sectional to the z'-axis, FIG. 31D; and
3) $T_{AD}$ is angular displacement around the long axis of the heart—this measures rotation on th plane cross sectional to the z'-axis, FIG. 31E.

The LAD shape-motion model is initialized as $s(u,v,0)=e(u,v)$. Then, the shape and position of the LAD over time is given by:

$$s(u,v,t)=((T_{AD} \cdot T_{RD} \cdot T_{LD})(u,t))(e(u,v)) \quad (12)$$

where $s(u,v,t)=(s_1(u,v,t), s_2(u,v,t), s_3(u,v,t))^T$. The longitudinal displacement in the local coordinate system of the heart can be expressed as follows:

$$T_{LD}(u,t) = \begin{bmatrix} 1 & 0 & 0 \\ 0 & 1 & 0 \\ 0 & 0 & \lambda(u,t) \end{bmatrix} \quad (13)$$

where $\lambda(u,t)$ is a time-varying longitudinal displacement parameter function. The ratio $\lambda$ represents contraction (values less than 1) or expansion (values greater than 1). The radial displacement can be parameterized as follows:

$$T_{RD}(u,t) = \begin{bmatrix} \rho(u,t) & 0 & 0 \\ 0 & \rho(u,t) & 0 \\ 0 & 0 & \rho(u,t) \end{bmatrix} \quad (14)$$

where $\rho(u,t)$ is a time-varying radial displacement parameter function. The ratio $\rho$ represents contraction (values less than 1) or expansion (values greater than 1) towards the long axis of the heart. Finally, the angular displacement around the long axis of the heart can be parameterized as follows:

$$T_{AD}(u,t) = \begin{bmatrix} \cos(\theta(u,t)) & -\sin(\theta(u,t)) & 0 \\ \sin(\theta(u,t)) & \cos(\theta(u,t)) & 0 \\ 0 & 0 & 1 \end{bmatrix} \quad (15)$$

where $\theta(u,t)$ is a time-varying angular displacement parameter function. Negative values for $\theta$ represent clockwise rotation when looking from the apex towards the base of the heart. FIG. 31C depicts the generalized cylinder after deformations at different time steps.

The aim here is to extract only the global shape change and motion imparted by myocardium onto the LAD. Since local deformations d are constrained to zero, the degrees of freedom of the LAD are incorporated into the vector:

$$q=(q_c^T, q_R^T, q_s^T)^T \quad (16)$$

which consists of the parameters necessary to define the translation $q_c$, rotation $q_R$, global deformation $q_s$, of the model [28], [29]. Note that in the proposed model for the LAD, the pose parameters $q_c$ and $q_R$ define a local coordinate system for the heart.

Thus the shape-motion parameters:

$$q_s=(l_1(u),l_2(u),l_3(u),r(u),\lambda(u,t),\rho(u,t),\theta(u,t))^T \quad (17)$$

and the vector of motion parameters is defined as:

$$q_T=(\lambda,\rho,\theta)^T \quad (18)$$

"Note that the relation between: i) positive magnitude (for ratios) and ii) positive sign (for angle) of the shape-motion parameters and iii) the phase of the cardiac cycle may suggest the cycle that the data belongs to".

D. Parametric Shape-Motion Estimation

1) Kinematics and Dynamics

The velocity $\dot{x}$ of the points described by Eq. 2 can be estimated as:

$$\dot{x} = \frac{d(x)}{dt} = \frac{d(c+Rs)}{dt} = \dot{c} + \dot{R}s + R\dot{s} = \dot{c} + B\dot{\theta} + R\dot{s} \quad (19)$$

where $\theta=( \ldots, \theta_i, \ldots )^T$ is the vector of rotational coordinates of the model, $B=[ \ldots, \partial(Rs)/\partial\theta_i, \ldots ]$, and $\dot{s}$ can be expressed as:

$$\dot{s} = \left[\frac{\partial(s)}{\partial q_s}\right]\dot{q}_s = J\dot{q}_s \quad (20)$$

where J is the Jacobian matrix of the global reference shape s. Therefore, the position over time $\dot{x}$ can be rewritten as:

$$\dot{x}=[IBRJ]\dot{q}=L\dot{q} \quad (21)$$

where L is the Jacobian matrix that maps the model parameters into the 3D space.

2) Simplified Lagrangian Equations of Motion

In Lagrangian mechanics, equations of motion are written in terms of a second order partial differential equation:

$$M\ddot{q}+D\dot{q}+Kq=g_q+f_q \quad (22)$$

where M, D, and K are the mass, the damping, and the stiffness matrices, respectively, $g_q$ denotes inertial forces between the global and local degrees of freedom of the model. Generalized forces respect to the model degrees of freedom are denoted by $f_q$. The previous formulation establishes a general framework for shape-motion estimation. To estimate global descriptors of motion, we constrain Eq. 22 by setting: i) the mass density term M, equal to zero, ii) the dumping term D, equal to the identity matrix, and iii) the forces $g_q$, to have a null effect in model degrees of freedom.

Therefore, the resulting simplified Lagrangian equations to estimate LAD shape-motion are of the form:

$$\dot{q} + Kq = f_q \quad (23)$$

where K is the stiffness matrix of the simulated elastic material [29], and the vector $f_q$ represents the external forces that the LAD data apply to the LAD shape-motion model. The LAD shape-motion formulation Eq. 23 implies that the current model has no inertia, making the model to come to rest as soon as the forces $f_q$ reaches an equilibrium or vanish. To solve Eq. 23 we employ a first order Euler method.

3) Model Force Computation

The generalized forces $f_q$ are defined as:

$$f_q = \int L^T f du \quad (24)$$

where $f_q$ modify the degrees of freedom of the model, and f denotes the 3D force distribution applied to the model. In order to compute f, given a data point p in the LAD model, the closest point z to the LAD is calculated, then f is computed as:

$$f = \gamma(z - p) \quad (25)$$

where γ is a constant value that regularize the strength of the force.

Fitting is accomplished by integrating the Lagrangian equations through time using a physics-based modeling framework as described by Terzopoulos and Metaxas [27], [28]. Once the equilibrium is reached, the values of q, are the shape-motion parameters of the LAD.

E. Algorithm

The algorithm to estimate the LAD shape-motion parameters assumes that the LAD has been previously segmented at every phase from ES to ED or from ED to ES, and it is comprised of t following steps:

Step 1

Determine translation and orientation parameters $q_c$ and $q_R$: The long-axis of the heart is localized manually by selecting: i) the center of the base, the vector c, and ii) the center of the apex, the vector a. The selection is performed only once, either at the ED or ES. The vector c is associated with $q_c$. The orientation matrix R is computed from the orientation and position of the long axis (parallel to the z' axes) with respect to the measured trans-axial (parallel to the z axis). Where the long axis is assumed to be parallel to the vector which goes from c to a, parallel to z', see FIG. 28C.

| Algorithm 1 Shape-motion analysis of the LAD | |
|---|---|
| Require: | The vector c and the orientation matrix for R, for the heart coordinate system Def. 1. Tthe number of phases $N_{phases}$, and the LAD points from ES to ED or from ES to ES. |
| Ensure: | LAD shape-motion parameters q, |
| Step 1: | Determine translation and orientation parameters $q_c$, $q_R$ at the ED or ES, (Eq.(2)) |
| Step 2: | Estimate the global reference shape parameters $q_e$, (Eq.(10)) |
| Step 3: | For i = 1 to $N_{phases}$ Estimate the motion parameters $q_{T_i}$ at each phase, (Eq.(18)) |

Anatomically, respect to the trans-axial slices of the EBCT data, the heart begins with the emergence of the great cardiac vessels from the base of the heart and ends at the diaphragm near the chest wall. The splitting of the pulmonary trunk takes place two or three slices above the base of the heart (where the left main coronary artery starts) and serves as the landmark to locate the center of the base of the conical heart. The apex of the conical heart is localized about 6-8 slices below the first appearance of the liver in the EBCT scan. The orientation and position of the long axis (with respect to the measured trans-axial images) define two rotation angles and the 3D coordinates of the origin, which are used to re-orient the trans-axial data into the heart-centered coordinate system. The trans-axial body axis is transformed to align with the long-axis of the heart. By letting global translation q, and orientation $q_R$ to be constant from ES to ED or ED to ES, φ is fixed and subsequently the LAD shape-motion parameters are expressed respect to φ.

Step 2

Estimate the global reference shape parameters $q_e$: Estimating the shape parameters is comprised of the following: i) selecting points corresponding to the medial axis (skeleton) of the LAD, ii) fitting the curve I to the LAD medial axis, and iii) initializing the generalized cylinder e with constant radius, and deforming the model to the LAD points.

Figure 32A:
FIGS. 32A-D depict data constructions: (A) Selected center line points along the LAD, (B) Parametric Frenet-Serret frames along the LAD, (C) Deformable model capturing the global shape of the LAD superimposed with the volume from the EBCT coronary angiography, (D) Segmented LAD from ES to ED, depicting the shape motion deformations w.r.t the heart-centered coordinate system ($x^i$, $y^i$, and $z^i$ axes)
Figure 32B:
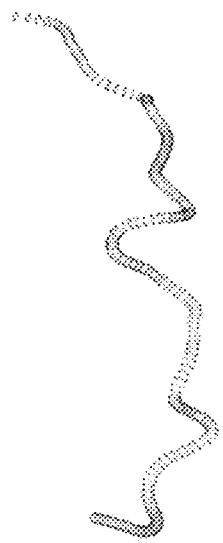
Figure 32C:
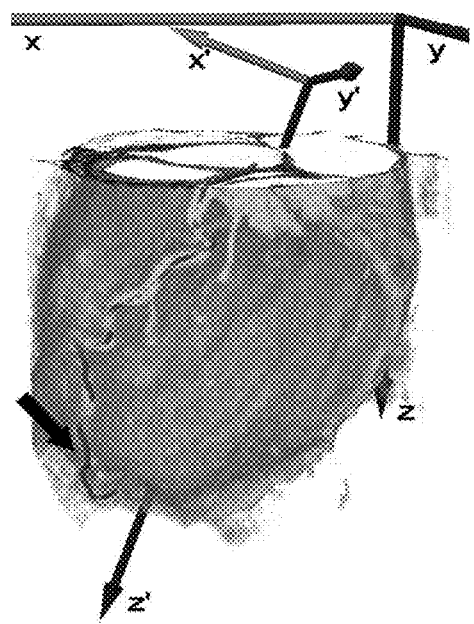

The centerline selection is performed from the segmented LAD, and thus performed manually at only the ES or the ED. The number of center points corresponding vary from 25 to 35 points from subject to subject, FIGS. 32A&B. A polynomial curve is fitted to the centerline points in order to capture the global reference shape and the generalized cylinder is initialized with constant radius. The model is deformed by the letting generalized forces apply from the model to the LAD data. The resolution in the u and v axis was selected from 32 to 64 samples in the u parameter (number of points per circle) and from 32 to 120 samples in the v axis. The sampling rate can be set differently according to the needs of the data, FIG. 32C.

Step 3

Figure 32D:
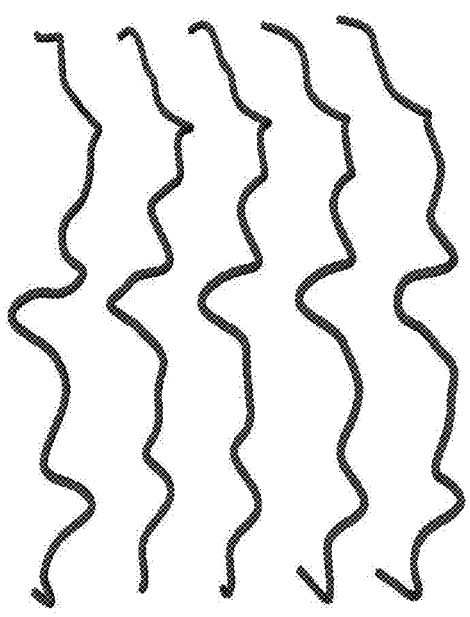

Estimate the motion parameters $q_{T_i}$ at each phase: Fitting at every phase is accomplished by fitting the LAD model from phase i−1 to the phase i, from ES to ED or ED to ES. The model is fitted to the data according to Eq. 23, where the generalized forces $f_q$ pull the LAD model towards the LAD data-points. The LAD model stops deforming once: i) the generalized forces $f_q$ vanish, or ii) an equilibrium for the forces is reached. Note that when fitting the LAD model from phase i−1 to phase i, the parameters q, are updated in an iterative way by solving Eq. 23. FIG. 32D depicts deformations over time.

IV. Results

We have performed a number of experiments including both simulated and contrast enhanced EBCT data in order to: 1) assess the validity of our LAD shape-motion estimation model, and 2) compare the range of shape-motion parameters computed by our method with the torsional measurements reported for LV through physiological experiments [32].

A. Simulated Data

Figure 33A:
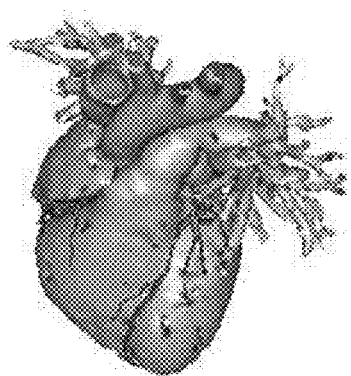
Figure 33B:
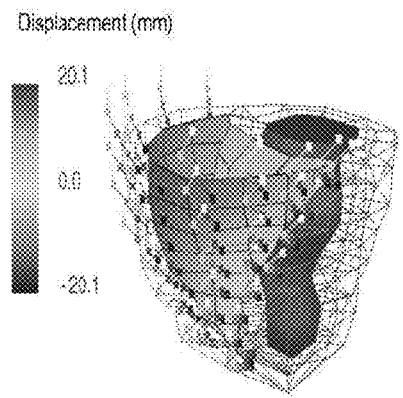
Figure 33C:
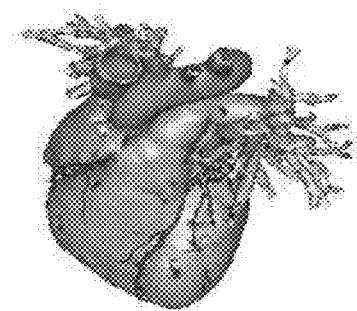
Figure 33D:
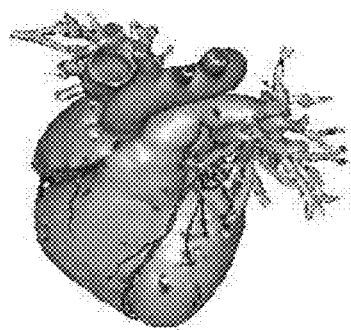
Figure 33E:
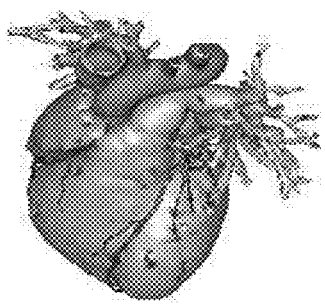
Figure 33F:
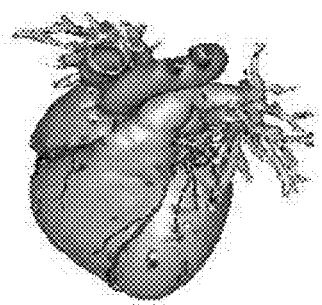
Figure 33G:
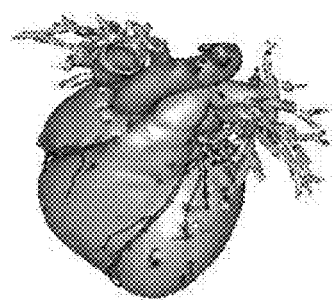
Figure 34A:
FIGS. 34A-D depict model fitting for the simulated data, (A) From left to right, initialization and fitting to the LAD points at phase one and (B-D) fitting from phase two to four.
Figure 34B:
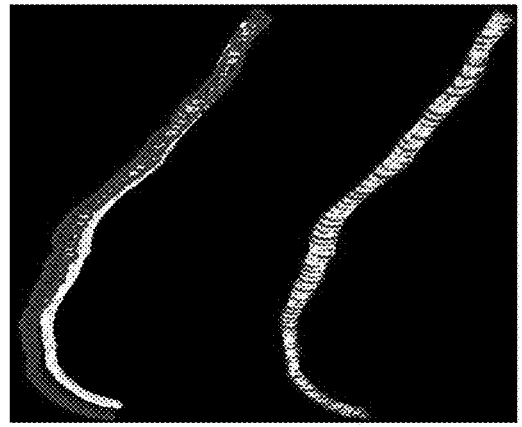
Figure 34C:
Figure 34D:
Figure 35A:
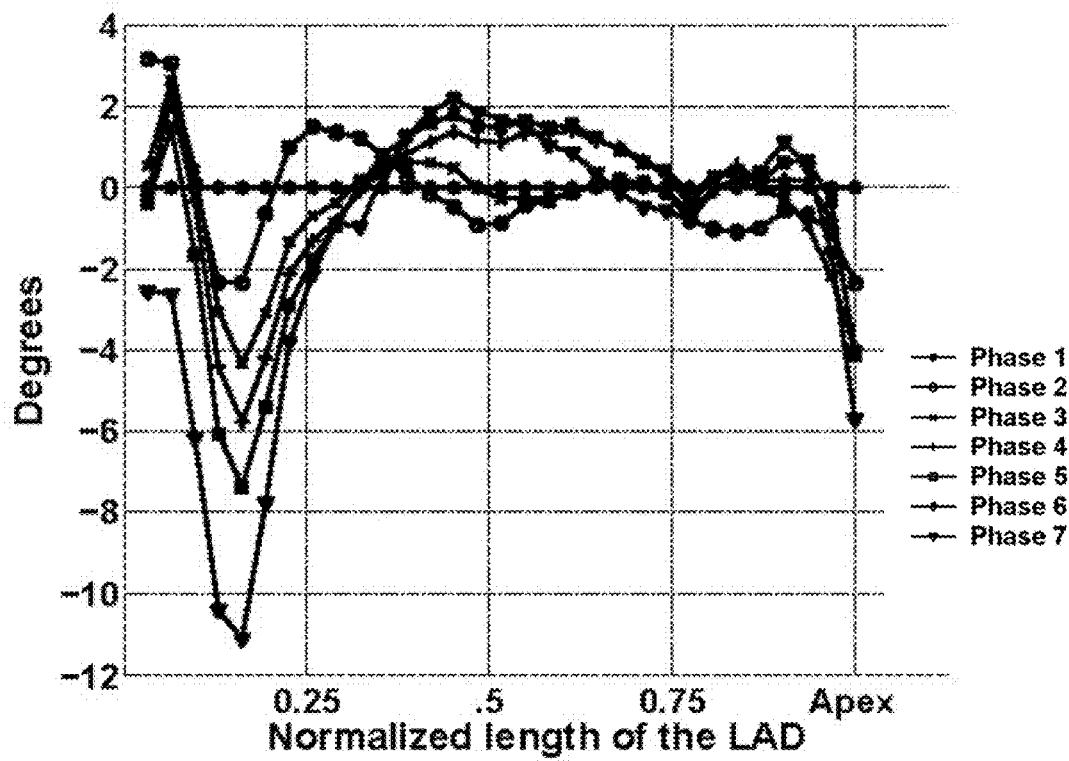
FIGS. 35A-E depict angular displacement values (in degrees) for subjects and simulated data. Positive (negative) parameter values represent counter-clockwise (clockwise) rotation along the long axis of the heart, as viewed from the apex towards the base. (A,B,D) (ED-ES) subjects S1, S2 and S3, respectively; (C,E) (ES_ED) subject S4 and simulated data, respectively.
Figure 35B:
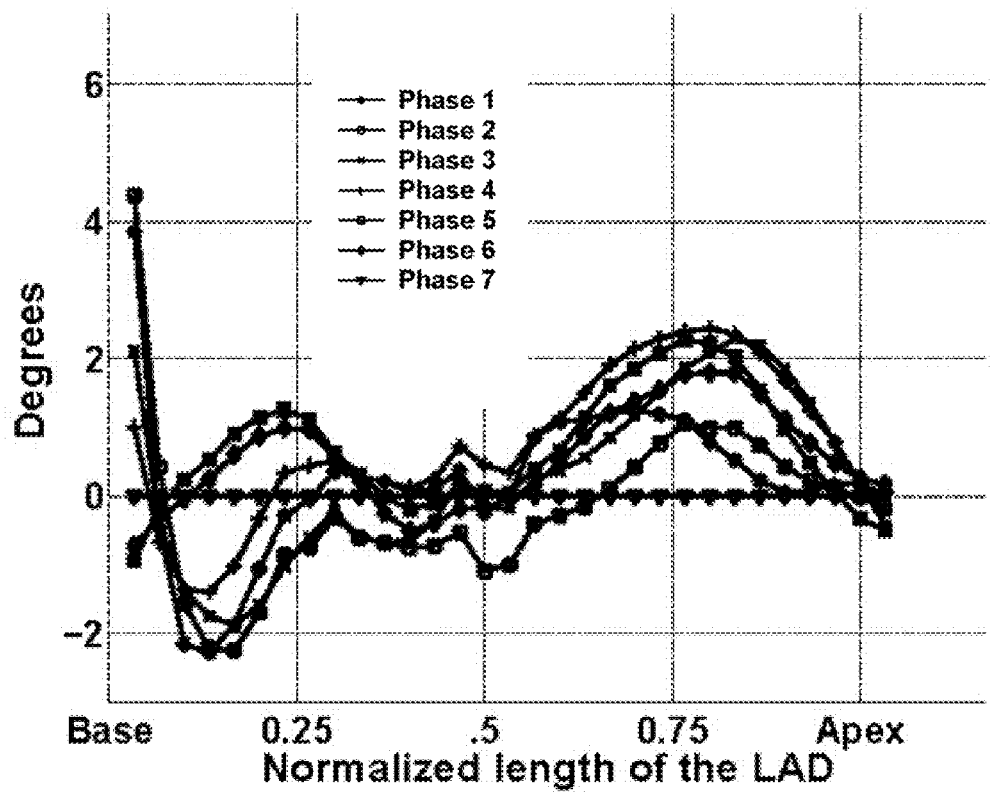
Figure 35C:
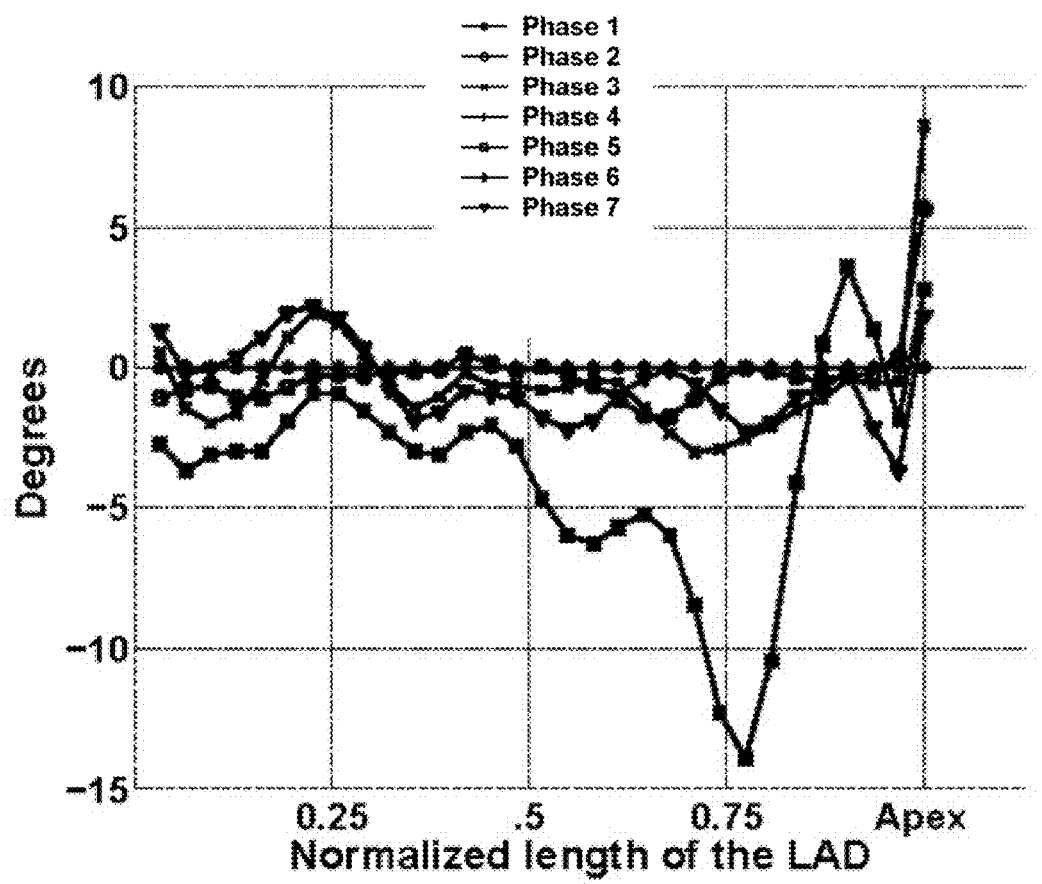
Figure 35D:
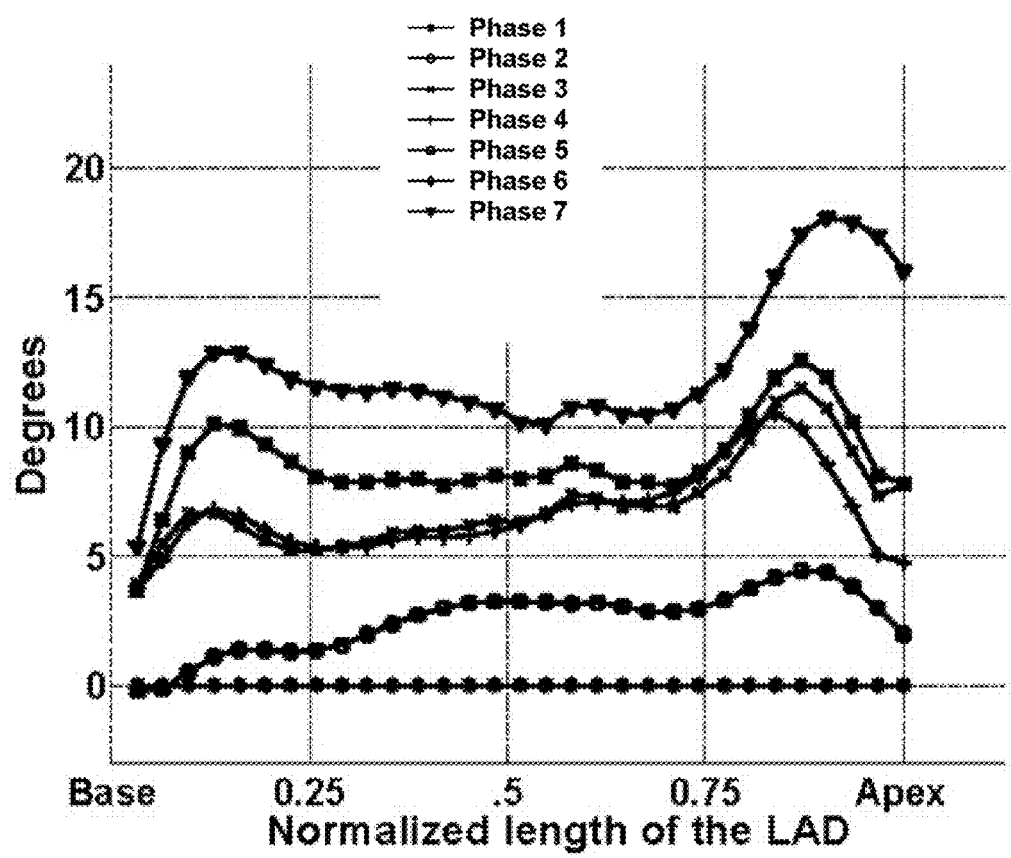
Figure 35E:
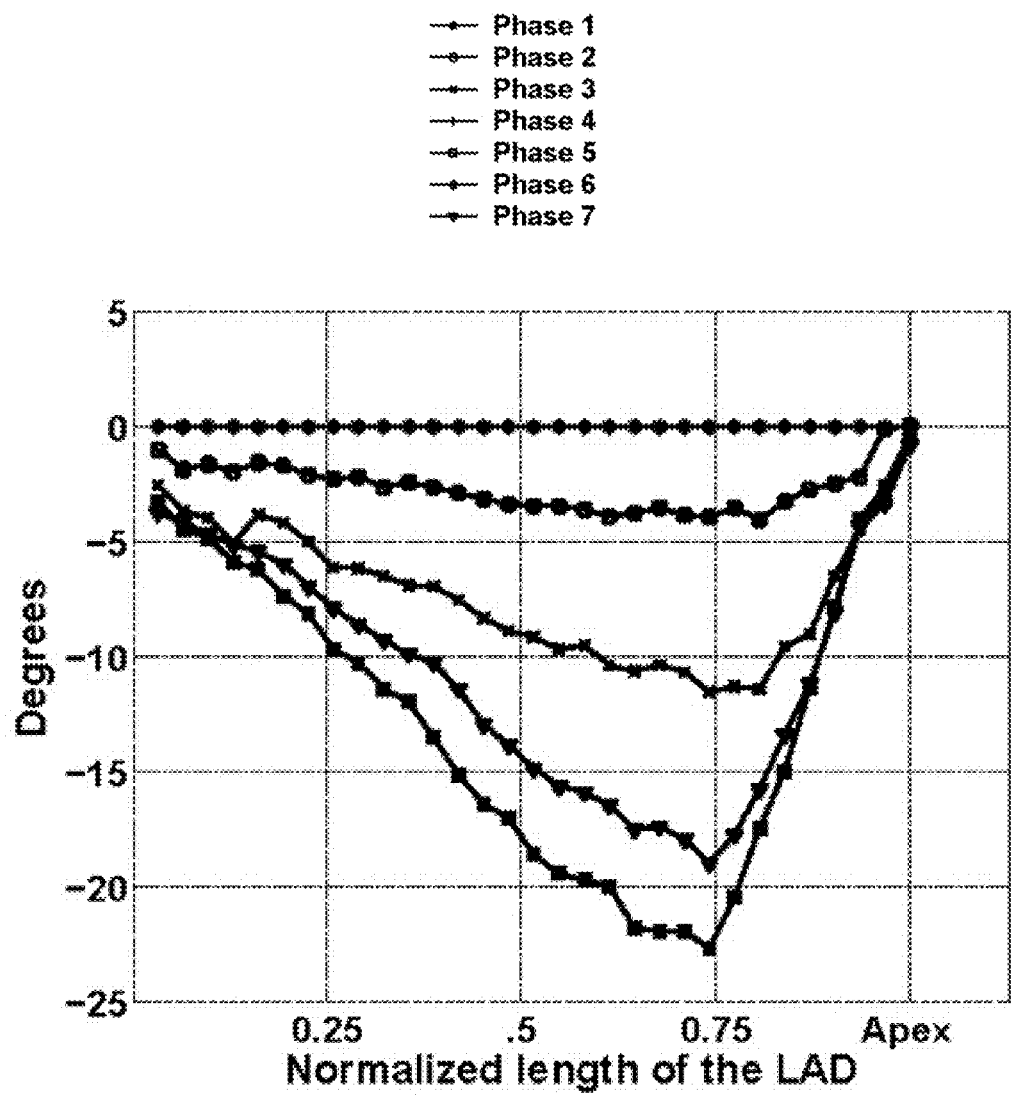

To evaluate our shape-motion model, we simulated the heart motion corresponding to the end-diastolic phase by considering a prototype that consists of the following two components: 1) a geometric model of the heart from Visible Productions™; these geometric models have been extracted using the Visible Human Data Project and include both the heart surface and the coronary artery tree (FIG. 33A), and 2) the patient-specific heart motion data provided by Prof. Metaxas (Rutgers University); motion data were obtained using MRI-SPAM M tagging (SPAtial Modulation of Magnetization) [33], [34] (FIG. 33B). We then animated the geometric model using the patient-specific heart motion data from both the LV and right ventricle (RV) to create simulated data corresponding to the LAD. FIGS. 33C-G depict selected frames of the animation from ES to ED, and FIGS. 33H-J depict the LAD deformations. Fitting was accomplished as described in Alg. 1. The resolution in the u and v axis was 32 samples in both cases. FIG. 34A depicts: i) the LAD initialization, ii) fitting of the LAD model by letting the longitudinal, radial, and angular displacement change over time, and iii) fitting by letting the radius to adjust to the points. FIGS. 34B-D illustrates the fitting process from phase one to phase four. FIGS. 35A-E depict angular displacement for simulated data, where the absolute value of the angle increases from 3.26° at the basal third towards the apex, reaching the maximum absolute value of −22.67° at the beginning of the apical third, and decreasing back to −0.34° in the extreme apical portion.

B. EBCT Data

To study our LAD shape-motion analysis model, coronary angiographies were performed four volunteer subjects with a GE Imatron EBCT scanner. The acquisition parameters are given in Table V. The acquisition for different subjects comes from different portions (ED to ES or ES to ED) of the cardiac cycle as presented in Tables VI and VII. The simulated data and EBCT data for S4 were acquired during ES to ED portion (recoil and relaxation of the left ventricle in this phase) of the cardiac cycle. Points corresponding to the lumen of the LAD were manually segmented in each subject. The segmentation was done at every phase of the cardiac cycle per subject. An initial estimation of the LAD medial axis was based from the LAD center points interactively marked. The centerline points selection was performed only once either at the ES or ED phase. Once the LAD points are given and an initial estimation to the LAD centerline is obtained, fitting at every phase was accomplished according to Algorithm 1. The radius was set to: 0.7 mm.

TABLE V

Acquisition Parameters for the Selected Ebct Coronary Angiography Data

|  | S1 | S2 | S3 | S4 |
|---|---|---|---|---|
| Resolution (mm) | 0.48 × 0.48 × 1.5 | 0.48 × 0.48 × 1.5 | 0.58 × 0.58 × 1.5 | 0.58 × 0.58 × 1.5 |
| P hases/I mages per phase | 6/112 | 7/96 | 5/96 | 6/82 |
| Age/Gender | 44/Male | 56/Male | 57/Male | 65/Male |

We present the estimated shape-motion parameters ($\lambda$, $\rho$, and $\theta$) for the EBCT coronary angiographies. Table VI presents the mean ($\mu$), standard deviation ($\sigma$), maximum (max), and minimum values (min) for the shape-motion parameters in the basal, mid-ventricular, and apical segments of the LAD, as well as the average $\lambda$, $\rho$, and $\theta$ values in the basal, mid, and apical third of the LAD.

TABLE VI

Statistics Corresponding to Shape-Motion Parameters for Subjects S1-s4 at Three Sections of the Lad Parameter $\theta$ Is Measured in Degrees

|  | Basal | | | Mid-Ventricular | | | Apical | | |
|---|---|---|---|---|---|---|---|---|---|
|  | $\mu$, $\sigma$ | max | min | $\mu$, $\sigma$ | max | min | $\mu$, $\sigma$ | max | min |
| S1: ED-ES | | | | | | | | | |
| log$\lambda$ | 0.008, 0.034 | 0.038 | −0.084 | 0.004, 0.003 | 0.009 | −0.001 | −0.010, 0.012 | 0.003 | −0.032 |
| log$\rho$ | −0.020, 0.064 | 0.043 | −0.146 | −0.021, 0.019 | 0.018 | −0.042 | −0.029, 0.044 | 0.024 | −0.126 |
| $\theta$ | −4.84, 3.80 | −0.88 | −11.11 | 1.30, 0.65 | 2.20 | 0.29 | −0.64, 1.82 | 1.13 | −5.69 |
| S2: ED-ES | | | | | | | | | |
| log$\lambda$ | −0.029, 0.022 | 0.005 | −0.057 | 0.002, 0.009 | 0.015 | −0.011 | −0.001, 0.005 | 0.010 | −0.008 |
| log$\rho$ | 0.054, 0.056 | 0.144 | −0.020 | −0.024, 0.003 | −0.020 | −0.029 | −0.014, 0.016 | 0.010 | −0.029 |
| $\theta$ | −0.37, 1.77 | 3.84 | −2.28 | 0.47, 0.53 | 1.19 | −0.25 | 0.50, 0.49 | 1.24 | 0.00 |
| S3: ED-ES | | | | | | | | | |
| log$\lambda$ | −0.069, 0.068 | −0.023 | −0.250 | −0.092, 0.013 | −0.074 | −0.107 | −0.067, 0.025 | −0.039 | −0.098 |
| log$\rho$ | −0.013, 0.050 | 0.039 | −0.139 | −0.024, 0.011 | −0.011 | −0.040 | −0.041, 0.083 | 0.037 | −0.234 |
| $\theta$ | 11.09, 2.23 | 12.85 | 5.41 | 10.80, 0.46 | 11.47 | 10.09 | 14.65, 3.04 | 18.09 | 10.46 |
| S4: ED-ES | | | | | | | | | |
| log$\lambda$ | 0.017, 0.007 | 0.025 | 0.007 | 0.047, 0.016 | 0.068 | 0.019 | 0.037, 0.021 | 0.067 | 0.008 |
| log$\rho$ | −0.058, 0.021 | −0.031 | −0.097 | −0.018, 0.028 | 0.019 | −0.059 | −0.124, 0.134 | 0.021 | −0.302 |
| $\theta$ | −2.33, 0.94 | −0.94 | −3.70 | −4.12, 1.61 | −2.08 | −6.27 | −4.42, 6.26 | 3.56 | −13.97 |

V. Discussion

A. Subjects S1-S3

The negative values of log λ and log ρ for subjects S1-S3 (FIGS. 36A-F and FIGS. 37A-F) suggests longitudinal contraction and movement of the anterior-interventricular groove towards the long axis of the heart, while the positive values for S4 suggests relaxation of the LV with the anterior-interventricular groove moving away from the long axis of the heart. Motion parameters depicted in FIGS. 36A-F and FIGS. 37A-F suggests that LAD undergoes a pronounced change in longitudinal length in the apical third and near extreme basal portion (near the atria). This pattern of longitudinal contraction (from ED to ES) and elongation (ES to ED) suggests movement of the apex towards (ED to ES) and away (ES to ED) from the base during the cardiac cycle.

FIGS. 37A-F depicts the shape-motion parameters for subjects S1 and S2; in both cases the motion of the LAD is from ED to ES. The average angular displacement values at the ES were −1.36° and 0.21° for S1 and S2, respectively. Regarding the data for S3, the heart's motion is from ED to ES, capturing the contraction of the left ventricle. FIGS. 36B,D,F depict the shape-motion parameters for S3. In this case the angular displacement values are positive, indicating a counter-clockwise motion of the LAD. As can be observed, the magnitude of the angular displacement is higher in the mid-apical third of the heart mainly localized in the apical third of the heart.

B. Subject S4

Displacement angles for S4 vary from 0.94° in the basal third to 3.56° in the apical third. The magnitude of angular deformation increases from the base towards the apex, reaching its maximum at the beginning of the apical third. It is important to mention that for S4 the LAD covers a longer portion of the apex compared to that of the simulated data. As the longer portion of the LAD traverses around the apex onto the posterior interventricular groove and the apex moves (radial and longitudinal displacement) from ES to ED, it results in change of sign. This suggests that the base and apex rotate in opposite directions, relative to the mid portions of the LAD during relaxation of the left ventricle in this portion of the cardiac cycle.

C. Clinical Correlation

Hansen [32], reported torsional angles at the anterior-apical third LV by using biplane cineradiography of tantalum helices. The reported value was 13.3+/−6.0°. The maximum torsional angles in absolute value at the anterior-apical third for S1 to S4 are: −5.69°, 1.24°, 10.09°, and −13.97°. We note that the maximum difference is 5.06° corresponding to S2.

The length of the LAD at every phase is depicted in Table VII. The artery length for Subjects S1-S3 undergo an overall contraction while for Subject S4 the artery is subject to an overall expansion. These values are consistent with those reported by: i) Schlant [35], where the LAD length was measure from 10 to 13 cm, and ii) Ibanez [36], where the LAD average length was 13.6 cm, ranging from 11.77 to 14.74 cm.

TABLE VII

Lad Length in Mm. From Es to Ed and Es to Es for Subjects s1-S4 S1-S3 (ES-ED) and S4 (ED-ES)

| | Phase No. | | | | | | |
|---|---|---|---|---|---|---|---|
| | 1 | 2 | 3 | 4 | 5 | 6 | 7 |
| S1 | 126.331 | 127.136 | 133.0 | 136.621 | 138.142 | 141.127 | |
| S2 | 105.006 | 106.98 | 105.599 | 111.924 | 112.813 | 114.229 | 118.911 |
| S3 | 137.049 | 141.481 | 146.137 | 148.346 | 150.373 | | |
| S4 | 147.5 | 144.418 | 140.926 | 137.791 | 135.769 | 130.789 | |

D. Relationship to Cardiac Morphology at the Anterior and Lateral Segments of the LV By exploiting 4D information provided by the EBCT data we combine global and local descriptors to describe the LAD dynamics over the cardiac cycle. Local descriptors (point-to-point dynamics) for the LAD, over the cardiac cycle allow to differentiate and identify different anatomical regions with different deformation patterns.

The magnitude of ρ suggests that the LAD's overall movement from ES to ED is motioning away from the long-axis of the heart. The parameter λ shows overall higher absolute values in the basal segment, decreasing in the mid-ventricular segment and again increasing at the beginning of the apical third. The increasing values of longitudinal elongation for ES to ED, from base to apex, indicate that the LAD's elongation takes place primarily in the mid-ventricular to apical segment. The high absolute values of longitudinal and angular displacement in the apical third indicates the upwards (towards the base) and turning motion of the apex during the near systolic portion of the cardiac cycle. These shape-motion parameters along with the rate of change from ES to ED, show physiological trends expected for asymptomatic hearts [37]. Thus, our studies suggest that the tortuosity of the apical segment of the LAD is highly correlated with the magnitude of the rotation around the long axis of the heart.

E. Framework Potential and Limitations

We remark the fact that the shape-motion framework proposed, could be prone to variations due to: i) selection of the heart coordinate system (the shape-motion parameters are expressed respect to the local frame or reference), and ii) the LAD segmentation (the shape-motion parameters will reflect the deformations of the given segmentation). However assuming those conditions are properly fulfilled, through global descriptors, we express the LAD geometry and dynamics as a unit with only three parameters (λ, ρ, θ) (Eq. 18), where the sign of these parameters plays a meaningful role to distinguish the phase of the cardiac cycle to which the heart is subject. Moreover, by expressing these global and local features with respect to a local coordinate system for the heart, our model provides anatomically normalized geometric reference frame, which could facilitate comparison between various subjects. This suggests the possibility of classifying parameters associated with healthy and unhealthy hearts. This model serve as a detailed morphological model describing the interaction between coronary fluid flow and the vessel wall for the computational fluid dynamics simulations that will elucidate the biomechanical implications of the coronary arterial motion in vascular disease. In addition, the preoperative patient-specific shape-motion parameters could be potentially used for robotic surgery on the beating heart. Also, they can be used to compute geometric features like curvature, torsion, and discrete flexion points in the LAD's local frame of reference.

VI. Conclusion

We presented a parametric shape-motion model of the LAD using a deformable model-based framework. The deformation of the LAD is based on three motion primitives: 1) longitudinal displacement $T_{LD}$, 2) radial displacement $T_{RD}$, and 3) angular displacement $T_{AD}$ with respect to the long axis of the heart.

Our key accomplishments in the area of coronary artery functional morphology analysis are the following: 1) the development of a parametric model that captures global and local shape features of the LAD respect to a local coordinate system for the heart, 2) the parametric representation of non-rigid motion for the LAD during the cardiac cycle, and 3) the estimation of the shape-motion parameters of the LAD using a physics-based deformable model framework without any shape or motion specific assumptions.

REFERENCES CITED IN THIS SECTION

The following references were cited in this section:
[1] A. Frangi, W. Niessen, and M. Viergever, "Three-Dimensional modeling for functional analysis of cardiac images: A review." IEEE Trans. on Medical Imaging, vol. 20, no. 1, pp. 2-25, 2001.
[2] B. R. P. S. P. De-Feyter, "Ct-based coronary angiography," Journal of Invasive Cardiology, vol. 12, no. 1, pp. 23-24, January 2000.
[3] B. Rensing, A. Bongaerts, and R. Van-Geun, "Intravenous coronary angiography by electron beam computed tomography, a clinical evaluation." Circulation, no. 98, pp. 2509-2512, 1998.
[4] A. Schmermund, B. Rensing, and P. Sheedy, "Intravenous electron beam ct coronary angiography for segmental analysis of significant coronary artery stenoses: Feasibility and limitations," American Journal of Cardiology, no. 31, pp. 1547-1554, 1998.
[5] P. Reddy, D. Chernoff, J. Adams, and C. Higgins, "Coronary artery stenoses: Assessment with contrast enhanced electron beam ct and axial reconstructions," Radiology, no. 208, pp. 167-172, 1998.
[6] M. Cerqueira, N. Weissman, V. Dilsizian, A. Jacobs, S. Kaul, W. Laskey, D. Pennell, J. Rumberger, T. Ryan, and M. Verani, "Standardized myocardial segmentation and nomenclature for tomographic imaging of the heart: A statement for healthcare professionals from the cardiac imaging committee of the council on clinical cardiology of the american heart association," Circulation, vol. 105, pp. 539-542, January 2002.
[7] R. Ilia, G. Rosenshtein, J. Weinstein, C. Cafri, A. Abu-Ful, and M. Gueron, "Left anterior descending artery length in left and right coronary artery dominance," Coronary Artery Disease, vol. 12, no. 1, pp. 77-78, February 2001.
[8] J. Chen and A. Amini, "Quantifying 3-D vascular structures in MRA images using hybrid PDE and geometric deformable models," IEEE Transactions on Medical Imaging, vol. 23, no. 10, pp. 1251-1262, 2004.
[9] I. Kakadiaris, A. Pednekar, G. Zouridakis, and K. Grigoriadis, "Estimating the motion of the LAD: A simulation-based study," in Proc. Medical Image Computing and Computer Assisted Intervention (MICCAI), Utrecht, The Netherlands, October 2001, pp. 1328-1331.
[10] I. Kakadiaris, A. Pednekar, and A. Santamaria-Pang, "Three-dimensional shape-motion analysis of the left anterior descending coronary artery in EBCT images," in Proc. Medical Image Computing and Computer Assisted Intervention (MICCAI), vol. 1, Rennes, France, Sep. 26-30, 2004, pp. 1025-1033.
[11] Y. Kong, J. J. Morris, and H. D. McIntosh, "Assessment of regional myocardial performance from biplane coronary cineangiograms," American Cardiology, vol. 27, pp. 529-537, 1971.
[12] M. J. Potel, J. M. Rubin, S. A. MacKay, A. M. Aisen, and J. Al-Sadir, "Methods for evaluating cardiac wall motion in three-dimensions using bifurcation points of the coronary arterial tree," Investigative Radiology, vol. 18, pp. 47-57, 1983.
[13] D. J. Stevenson, I. Smith, and G. Robinson, "Working towards the automated detection of blood vessels in X-ray angiograms," Pattern Recognition Letters, vol. 20, no. 6, pp. 107-112, 1987.
[14] Z. Ding and M. Friedman, "Quantification of 3-D coronary arterial motion using clinical biplane cineangiograms," The International Journal of Cardiovascular Imaging, vol. 16, no. 5, pp. 331-346, 2000.
[15] S. Chen and J. Carroll, "Kinematic and deformation analysis of 4-D coronary arterial trees reconstructed from cine angiograms," IEEE Trans. on Medical Imaging, vol. 22, no. 6, pp. 710-721, 2003.
[16] M. Olszewski, R. Long, S. Mitchell, A. Wahle, and M. Sonka, "A quantitative study of coronary vasculature in four dimensions," in Proc. IEEE Int'l Conf. Engineering in Medicine and Biology Society (EMBS), vol. 4, July 2000, pp. 2621-2624.
[17] R. Liao, S. J. Chen, J. Messenger, B. Groves, J. Burchenal, and J. Carroll, "Four-dimensional analysis of cyclic changes in coronary artery shape," Catheterization and Cardiovascular Interventions, vol. 55, pp. 344-354, 2002.
[18] F. Mourgues, F. Devernay, G. Malandain, and E. Coste-Maniere, "3D+t modeling of coronary artery tree from standard non simultaneous angiograms," in Medical Image Computing and Computer-Assisted Intervention (MICCAI), ser. Lecture Notes in Computer Science, vol. 2208. W. J. Niessen, M. A. Viergever (Eds.), 2001, pp. 1320-1322. [Online]. Available: citeseer.nj.nec.com/article/mourgues01dt.html
[19] M. F. Gross and M. H. Friedman, "Dynamics of coronary artery curvature obtained from biplane cineangiograms," Journal of Biomechanics, vol. 31, pp. 479-484, 1998.
[20] S. Ruan, A. Bruno, and J. Coatrieux, "Three-dimensional motion and reconstruction of coronary arteries from biplane cineangiography," Image and Vision Computing, vol. 12, no. 10, pp. 683-689, 1994.
[21] G. Shechter, F. Devernay, E. Coste-Maniere, A. Quyyumi, and E. McVeigh, "Three-dimensional motion tracking of coronary arteries in biplane cineangiograms," IEEE Trans. on Medical Imaging, vol. 22, no. 4, pp. 493-503, 2003.
[22] B. Movassaghi, V. Rasche, M. Grass, M. Viergever, and W. Niessen, "A quantitative analysis of 3-D coronary modeling from two or more projection images," IEEE Transactions on Medical Imaging, vol. 23, no. 12, pp. 1517-1531, 2004.
[23] D. Zhaouha and M. Friedman, "Quantification of 3D coronary arterial motion using clinical biplane cineangiograms," International Journal of Cardiac Imaging, vol. 16, pp. 331-346, 2000.
[24] C. Blondel, R. Vaillant, G. Malandain, and N. Ayache, "3-D tomographic reconstruction of coronary arteries using a precomputed 4-D motion field," Physics in Medi-

[25] C. Blondel, G. Malandain, R. Vaillant, F. Devernay, E. Coste-Maniere, and N. Ayache, "4-D tomographic representation of coronary arteries from one rotational X-ray sequence," in Medical Image Computing and Computer-Assisted Intervention (MICCAI), ser. Lecture Notes in Computer Science, vol. 1, 2003, pp. 416-423.

[26] A. Frangi, W. Niessen, P. Nederkoor, J. Bakker, W. Mali, and M. Viergever, "Quantitative analysis of vascular morphology from 3D MR angiograms: In vitro and in vivo results," Magnetic Resonance in Medicine, vol. 45, no. 2, pp. 311-322, 2001.

[27] D. Terzopoulos and D. Metaxas, "Dynamic 3D models with local and global deformations: Deformable superquadrics," IEEE Trans. on Pattern Analysis and Machine Intelligence, vol. 13, no. 7, pp. 703-714, 1991.

[28] D. Metaxas and D. Terzopoulos, "Shape and nonrigid motion estimation through physics-based synthesis," IEEE Trans. on Pattern Analysis and Machine Intelligence, vol. 15, no. 6, pp. 580-591, June 1993.

[29] D. Metaxas and I. Kakadiaris, "Elastically adaptive deformable models," IEEE Trans. on Pattern Analysis and Machine Intelligence, vol. 24, no. 10, pp. 1310-1321, 2002.

[30] J. Stewart, Calculus. Pacific Grove, Calif.: Brooks/Cole Publishing Company, 1991.

[31] W. F. Bronsvoort, Direct Display Algorithms for Solid Modeling. Delft University Press, 1990, p. 79.

[32] D. Hansen, G. Daughters, E. Alderman, N. Ingels, and D. Miller, "Torsional deformation of the left ventricular midwall in human hearts with intramyocardial markers: regional heterogeneity and sensitivity to the inotropic effects of abrupt rate changes," Circulation Research, vol. 62, no. 5, pp. 941-952, May 1988.

[33] J. Park, D. Metaxas, A. Young, and L. Axel, "Deformable models with parameter functions for cardiac motion analysis from tagged MRI data," IEEE Trans. Medical Imaging, vol. 15, pp. 278-289, 1996.

[34] E. Haber, D. Metaxas, and L. Axel, "Motion analysis of the right ventricle from MRI images," in Proc. Medical Image Computing and Computer-Assisted Intervention (MICCAI), no. 1496, Cambridge, Mass., October 1998, pp. 177-188.

[35] R. Schlant, Hurst's The Heart, 8th ed. New York: McGraw-Hill, 1994, ch. Anatomy of the Heart, pp. 84-86.

[36] B. Ibanez, F. Navarro, M. Cordoba, P. M-Alberca, and J. Farre, "Tako-tsubo transient left ventricular apical ballooning: is intravascular ultrasound the key to resolve the enigma?" Heart, no. 91, pp. 102-104, 2005.

[37] L. Kwok and D. Miller, "Torsional deformation of the left ventricle," The Journal of the Heart Valve Disease, vol. 4, no. Supplement II, pp. S214-222, 1995.

Automated Pericardial Fat Quantification in Ct Data

A method for automatic pericardial fat burden quantification and classification is presented, where our method was evaluated using data from 23 subjects with very encouraging results.

I. Introduction

A recent survey reveals that over 64% of Americans are overweight or obese [1]. Obesity increases the risk for high blood cholesterol, high blood pressure, and diabetes. Individual cardiovascular risk can be quantified by the Framingham Risk Score [2], which integrates age, gender, total and HDL cholesterol, and systolic blood pressure. In modern medicine, fat tissue is no longer viewed as a simple energy storehouse of the body; instead it is considered an active organ with critical metabolic and immune regulatory functions. Recent evidence also indicates that pericardial fat may be a significant cardiovascular risk factor [3], [4]. Taguchi et al. have reported that pericardial fat was the strongest independent predictor for hemodynamically significant coronary artery disease (CAD) [3]. Wheeler et al. reported that pericardial fat is highly correlated with visceral fat, suggesting that increased pericardial fat, like increased abdominal visceral fat, may be a significant index of risk for CAD [4]. Noninvasive imaging techniques provide minimal-risk opportunities to detect disease, assess the individual risk of patients, and to study patients serially over time in assessment of therapy. Standard noninvasive diagnostic imaging modalities to assess the heart include CT, Single Photon Emission Computed Tomography(SPECT), Positron Emission Tomography (PET), and Magnetic Resonance Imaging (MRI). CT and MRI are both popular imaging modalities used to quantify fat distribution. However, CT is less expensive and provides better contrast between fat and non-fat tissues. In current clinical practice, pericardial fat quantification studies were limited to manually outlined region of interest (ROI) and preset fat attenuation thresholds, which are subject to inter-observer and inter-scan variability. Thus, the development of a computer-assisted method which provides unbiased and consistent results automatically with minimal human intervention is highly desirable.

In our previous work [5], [6], we have developed a tissue segmentation method based on a hierarchical, multi-class, multi-feature, fuzzy affinity framework and applied it for automatic segmentation and quantification of abdominal fat in CT (Automatic Fat Analysis in Computed Tomography—AFACT). In this section, we extend the framework for automatic pericardial fat quantification.

The rest of the section is organized as follows. Section II describes in detail the steps of our method. In Section III, we present results from our method and a comparison with manual segmentations, while in Section IV we present our conclusions.

II. Materials and Methods

Our work is based on a hierarchical, multi-class, multi-feature, fuzzy affinity-based framework [5], which combines the intensity and texture information with local "hanging togetherness" within a fat class. The fuzzy connectedness constraint for the object extraction presented in [7], [8],[9] is relaxed to allow global segmentation. Thus, instead of applying a space-invariant global threshold value, our computational framework adapts the threshold value locally to account for the local "hanging togetherness" of the tissue to be segmented. The Mahalanobis metric is used to compute the similarity of pixels in the intensity and texture-based feature space. The most discriminating combination of texture features for specific object regions (fat, nonfat, and background classes) is determined in the training phase of our framework.

A. Experimental Data

We evaluated our method using data from 23 subjects (15 male, 8 female, mean age 54.9±8.8 years). For each, 30 to 35 contiguous transverse images were obtained from the inferior margin of the right pulmonary arterial level (approximately 10 mm superior to the left main coronary artery) to the bottom of the heart. A section thickness of 3 mm, a field of view of 30 cm, and a matrix of 512×512 were used to reconstruct the raw image data, yielding a pixel size of 0.59×0.59 mm$^2$ and a voxel volume of 1.0 mm$^3$.

B. AFACT Methodology Overview (Pericardial)

The AFACT methodology is set forth below in outline format.

I. Training Phase
A. Estimate object-specific (fat, non-fat, background classes) distributions using a training data set.
  Step 1
    Compute relevant intensity and texture features
  Step 2
    Compute the most discriminating features.

II. Deployment Phase

B. Remove artifacts and find the contour outline of the human body.
  Step 3
    Remove equipment-related artifacts.
  Step 4
    Find the outline of the human body automatically for processing the data inside this contour.
C. Segment and label various organs/tissues in cardiac scan.
  Step 5
    Use anatomical landmark information to locate the upper and lower limits of the heart.
  Step 6
    Segment the inner-thoracic cavity using radial gradient sampling in each slice.
  Step 7
    Segment the lungs in each slice.
  Step 8
    Segment the heart and descending aorta in each slice.
  Step 9
    Update the 3D label map of the various organs in the volume.
D. Compute the fat statistics using the sample area around the seed point.
  Step 10
    Compute a seed point for the fat region in the center slice.
  Step 11
    Compute statistics dynamically for a sample region around the seed point.
E. Compute the fuzzy affinity-based object.
  Step 12
    Compute the most discriminating features selected from Step 2.
  Step 13
    Compute the global object affinity using the Mahalanobis metric.
  Step 14
    Compute the fat by thresholding the global object affinity image.
  Step 15
    Use labels determined in Step 9 to quantify pericardial fat.

C. AFACT Methodology Description (Pericardial)

A description of the AFACT methodology is set forth below.

1) Steps 1-2—Training Phase

Initially, Laws' features [10] and Gabor texture features [11] for the cardiac CT images were computed. The most discriminating feature combinations were determined according to their cumulative discriminating power. Our feature vector consisted of two features, namely intensity and Laws'ss feature.

2) Step 3—Remove Equipment-Related Artifacts

Many artifacts in the CT image (e.g., the patient table and wires) have intensity distributions very similar to that of the fat tissue. To correctly quantify the fat burden, it is important that such artifacts are removed from the image. We perform an artifact removal preprocessing step that automatically removes such artifacts. More details can be found in [6]. FIG. 38B depicts the image after the removal of detected equipment-related artifacts.

3) Step 4—Find the Outline of the Human Body Contour

First, we threshold the preprocessed image obtained after artifact removal step within the interval (−190<Hu<−30), a normal attenuation range for fat tissues [12]. Then, we perform outer boundary detection by looking at the intensity profile of equi-angular radial vectors originating from the centroid of the thresholded image. We call this method radial sampling, where each of these radial vectors is traversed with a first order gradient filter kernel to mark the points where there is a change from background to ROI. The outermost points on these vectors are marked as points on the human boundary contour. FIG. 39B depicts the filled human body contour after the outline is detected.

4) Steps 5-9—Segment and Label Various Organs/Tissues in Cardiac Scan

Figure 40A:
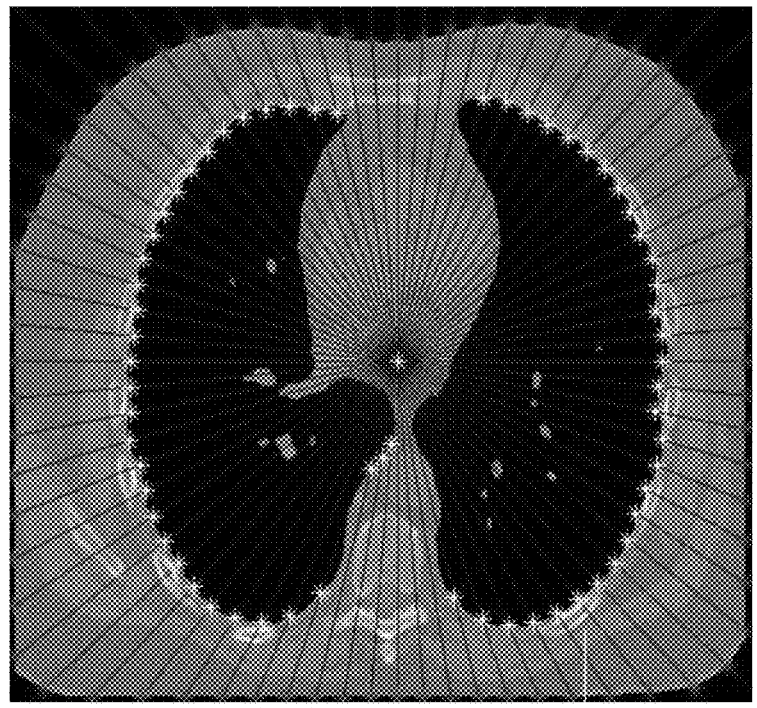
FIGS. 40A-B depict inner-thoracic cavity segmentation: (A) Radial sampling method, and (b) refined contour.
Figure 40B:
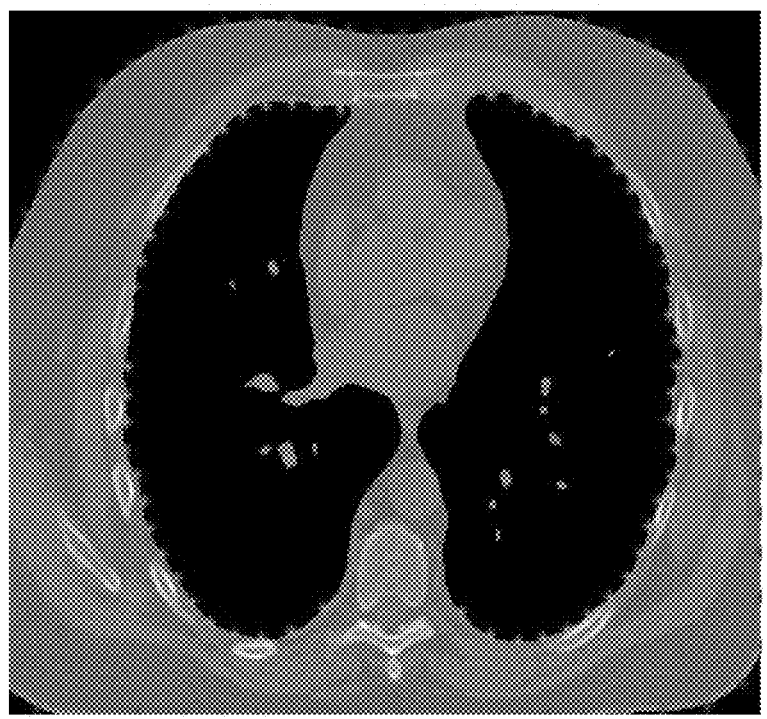
Figure 41A:
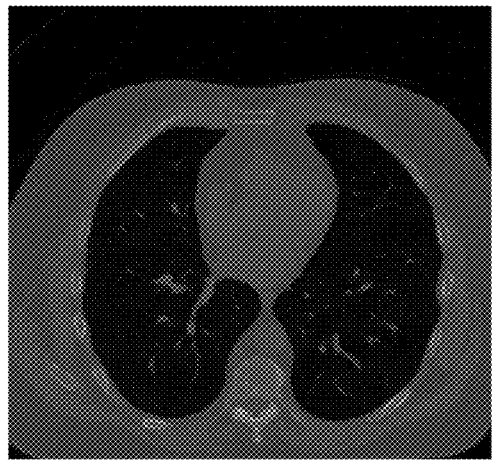
FIGS. 41A-B depict label maps: (A) Original image, and (B) corresponding labeled image.
Figure 41B:
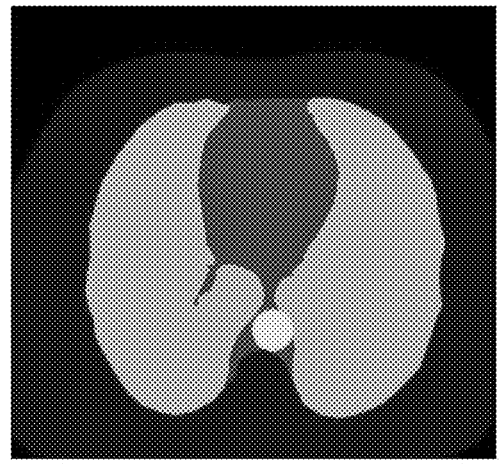

We consider slices between the start and end of the heart using anatomical landmark information. Specifically, we use the splitting of the pulmonary artery landmark slice to mark the start of the heart and the 2-3 slices below the appearance of the liver to mark the end of the heart. We use the area enclosed by the human body contour as our ROI and only search for fat pixels inside it. We locate the inner-thoracic cavity contour by using radial sampling as described in Step 3. FIGS. 40A-B depict the contours obtained by the radial sampling method. In addition to the fat threshold, we use a bone threshold (130 Hu) in order to mark the points at the spinal cord. The use of a fat threshold alone does not produce clear boundaries around the spinal cord. After we obtain the inner contour, which is also the boundary of the lungs, we label the region between the human contour and the lung boundary as subcutaneous thoracic region. Now the tissues inside the inner contour are fat, heart, and lung. The distribution of the lung tissue is well separated from the distribution of the heart and fat tissues in the histogram of the image. We compute a dynamic threshold to segment the lungs and assign a label. After the lung tissue has been removed, only the heart and fat tissues are left in the ROI. We take a sample pixel at the center of the ROI to compute the statistics of heart and threshold it with mean±2std to segment the heart tissue and apply a label to it. At the starting slice of the heart, we perform circle detection using the Hough transform to detect the descending aorta and track this circle in the following slides. Thus, we have labelled background, subcutaneous region, lungs, heart, and descending aorta in the 3D cardiac scan. FIG. 41B depicts the label map for various organs/tissues.

5) Steps 10-11—Compute the Fat Statistics Dynamically

Figure 42A:
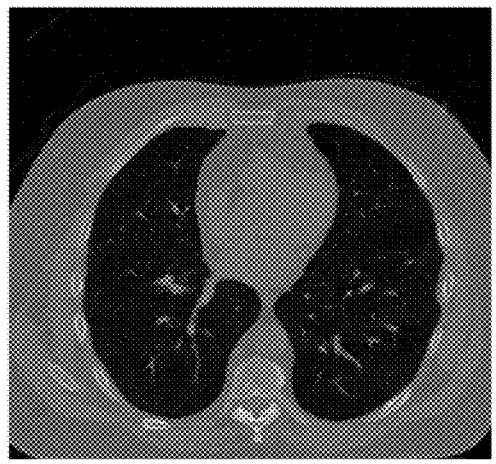
FIG. 42A-B depict dynamic computation of fat statistics: (A) Original image, and (B) sample region in the fat tissue.
Figure 42B:
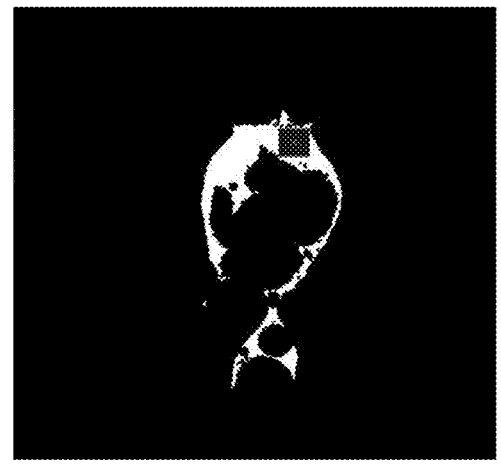

We compute the statistics for fat tissue in only one slice (i.e., the center slice of the cardiac scan). In step 8, after we threshold for heart tissue, most of the remaining tissue is the fat tissue which is not a contiguous region. We fit a square of maximum allowable size and compute dynamic statistics of fat by taking samples around the center of the square. FIG. 42B depicts the sample region around the seed point for computation of fat statistics. The average Hu for fat tissue varies across subjects and also depends on the CT scanner [12]. We use these dynamically computed fat statistics in our fuzzy affinity computation to make the method scanner independent.

6) Steps 6-8—Compute the Fuzzy Affinity-Based Object

First, the most discriminant features selected from Step 2 of the training phase are computed for the current image. Then, the global object affinity is computed using the Mahalanobis metric. The global affinity image has values between 0 and 1: the higher the value, the higher the probability that the tissue belongs to the fat region. The fat areas are obtained by thresholding the global object affinity image and using the global label map obtained from Step 9.

III. Results and Discussion

Figure 43A:
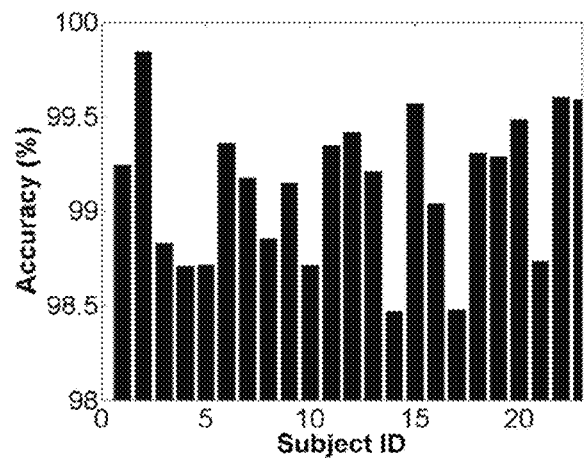
FIGS. 43A-C depict performance evaluation of AFACT for total fat segmentation: (A) accuracy, (B) true positive rate, and (C) true negative rate.
Figure 43B:
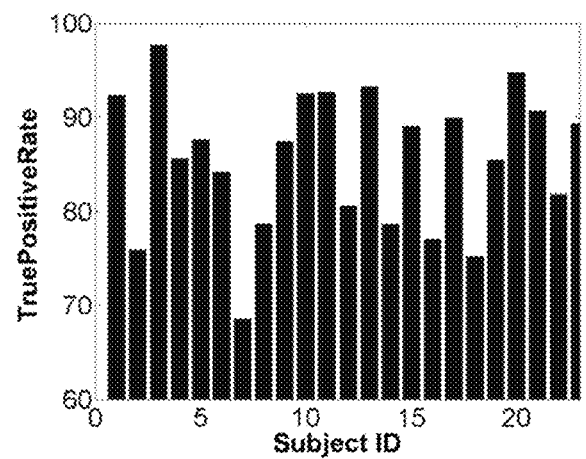
Figure 43C:
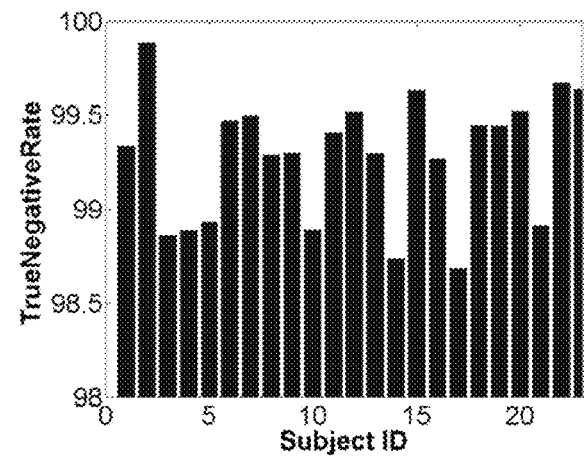
Figure 44A:
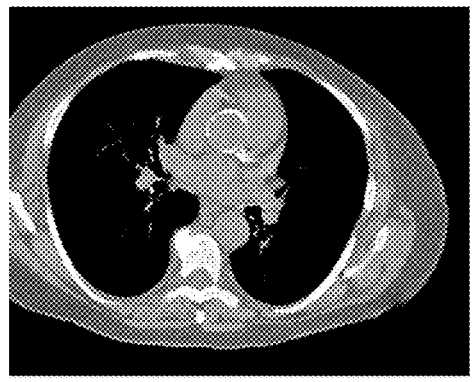
FIGS. 44A-F depict pericardial fat measured at left main (LM) artery split, 2 slices below LM level, and 3 slices below LM: (A,C,E) Original images, and (B,D,F) estimated pericardial fat (overlaid in red) respectively.
Figure 44B:
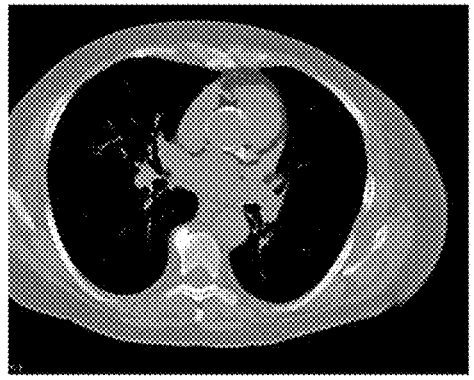
Figure 44C:
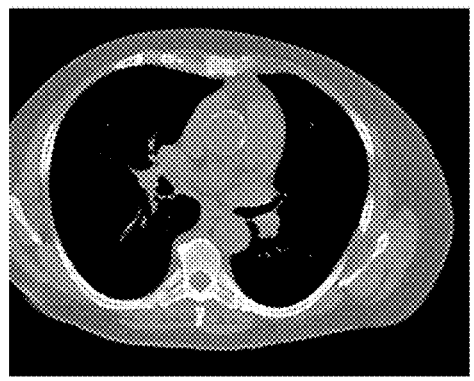
Figure 44D:
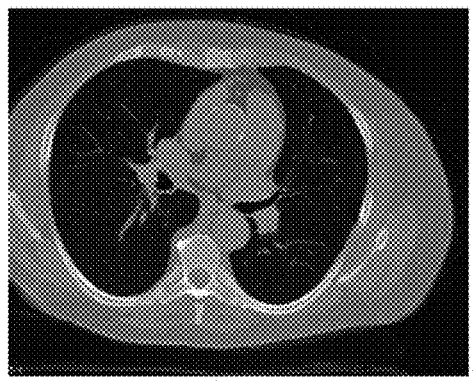
Figure 44E:
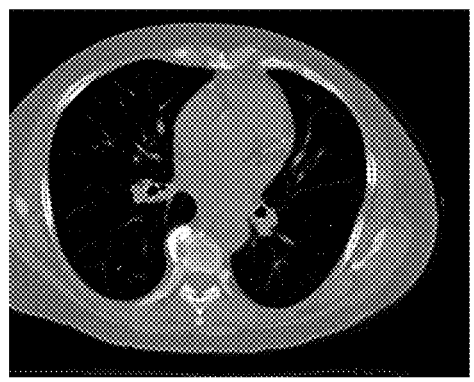
Figure 44F:
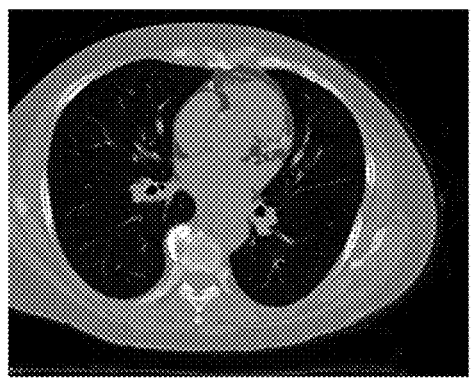

We have compared the results of our method to expert manual segmentations of pericardial fat for 23 subjects. The manual delineation of the fat region in the CT images, performed by experienced physicians/radiologists, was used as the gold standard. We evaluated the results of our algorithm by computing the three measures of accuracy recommended by Udupa et al. [13]. Specifically, we computed the false negatives, false positives, true negatives, and true positives by computing the number of pixels that were classified as the background and the ROI, both correctly and incorrectly. FIGS. 43A-C depict the accuracy, the true positive rate, and the true negative rate obtained by AFACT for pericardial fat quantification when compared with manual segmentation respectively. The mean accuracy for pericardial fat was 99.13%±0.38%. The mean true negative rate was 99.28%±0.33%. Finally, the mean true positive rate was found to be 85.63%±7.42%. The qualitative results of our algorithm for a subject at the split of the Left Main (LM), 2 slices above the LM, and 3 slices below the LM are depicted in FIGS. 44A-F.

IV. Conclusions

In this section, we have presented a method for automatic pericardial fat quantification. We have successfully quantified and classified the pericardial fat burden in cardiac CT images and performed evaluation against manual segmentations by experts. Our method achieves a comparable true negative rate and accuracy versus manual delineation of pericardial fat. This technique does not require seed initialization, correlates very well with manual readings by humans, and requires slightly less than one minute per CT slice. Clinical investigation of this tool is warranted to evaluate the role of pericardial fat in risk assessment.

V. References Cited in this Section

The following references were cited in the Automated Pericardial Fat Quantification in CT Data section.

[1] K. Flegal, M. Carroll, C. Ogden, and C. Johnson, "Prevalence and trends in obesity among US adults, 1999-2000," *Journal of the American Medical Association,* vol. 288, pp. 1723-7, 2002.

[2] P. W. Wilson, R. B. D'Agostino, D. Levy, A. M. Belanger, H. Silbershatz, and W. B. Kannel, "Prediction of coronary heart disease using risk factor categories," *Circulation,* vol. 97, pp. 1837-47, 1998.

[3] R. Taguchi, J. Takasu, Y. Itani, R. Yamamoto, K. Yokoyama, S. Watanabe, and Y. Masuda, "Pericardial fat accumulation in men as a risk factor for coronary artery disease," *Atherosclerosis,* vol. 157, no. 1, pp. 203-9, 2001.

[4] G. L. Wheeler, R. Shi, S. R. Beck, C. D. Langefeld, L. Lenchik, L. E. Wagenknecht, B. I. Freedman, S. S. Rich, D. W. Bowden, M. Y. Chen, and J. J. Carr, "Pericardial and visceral adipose tissues measured volumetrically with computed tomography are highly associated in type 2 diabetic families," *Invest Radiology,* vol. 40, pp. 97-101, 2005.

[5] A. Pednekar, A. N. Bandekar, I. A. Kakadiaris, and M. Naghavi., "Automatic segmentation of abdominal fat from CT data," in *Proceedings of the 7th IEEE Workshops on Application of Computer Vision* (WACV/MOTION'05). Colorado. USA, January 5-7, 2005, pp. 308-315.

[6] A. N. Bandekar, M. Naghavi, and I. A. Kakadiaris., "Performance evaluation of abdominal fat burden quantification in CT," in *Proceedings of the 27th Annual International Conference of the IEEE Engineering in Medicine and Biology Society,* Shanghai, China, September 1-4, 2005.

[7] A. Pednekar and I. Kakadiaris, "Image segmentation based on fuzzy connectedness using dynamic weights," *IEEE Transactions in Image Processing,* vol. 15, no. 6, pp. 1555-1562. June 2006.

[8] A. Pednekar, U. Kurkure, I. Kakadiaris, R. Muthupillai, and S. D. Flamm., "Left ventricular segmentation in MR using hierarchical multi-class multi-feature fuzzy connectedness," in *Proceedings of the 7th International Conference on Medical Image Computing and Computer-Assisted Intervention,* Saint-Malo, France, September 26-30 2004, pp. 402-410.

[9] J. Udupa and S. Samarasekera, "Fuzzy connectedness and object definition: theory, algorithms, and applications in image segmentation," *Graphical Models and Image Processing,* vol. 58, no. 3, pp. 246-261, May 1996.

[10] K. Laws, "Texture image segmentation," Ph.D. dissertation, University of Southern California, 1980.

[11] B. Manjunath and W. Ma, "Texture features for browsing and retrieval of image data," *IEEE Transactions on Pattern Analysis and Machine Intelligence,* vol. 18, no. 8, pp. 837-842, August 1996.

[12] Y. Tohru, N. Tadashi, Y. Mitsukazu, H. Abdul, M. Masakazu, Y. Kouichi, A. Takeshi, K. Kazuaki, F. Tohru, Y. Shizuya, and M. Yuji, "Abdominal fat: Standardized technique for measurement at CT," *Radiology,* vol. 211, pp. 283-286, 1999.

[13] J. Udupa, Y. Jin, C. Imielinska, A. Laine, W. Shen, and S. Heymsfield, "Segmentation and evaluation of adipose tissue from whole body MRI scans," in *Proceedings of the 6th International Conference on Medical Image Computing and Computer-Assisted Intervention,* Montreal, Canada, Nov. 15-18 2003, pp. 635-642.

Method 2

Fully automatic measurement of pericardial fat from non-contrast cardiac CT.

Rationale

The standard CT attenuation range for fat is defined to be from (−190, −30) HU [49]. The average CT attenuation for fat tissue varies across subjects and also depends on the CT scanner [49]. Consequently, robust clinical assessment of fat distribution requires a classification scheme that uses features beyond intensity. The software developed by inventors uses features beyond intensity.

Figure 45:
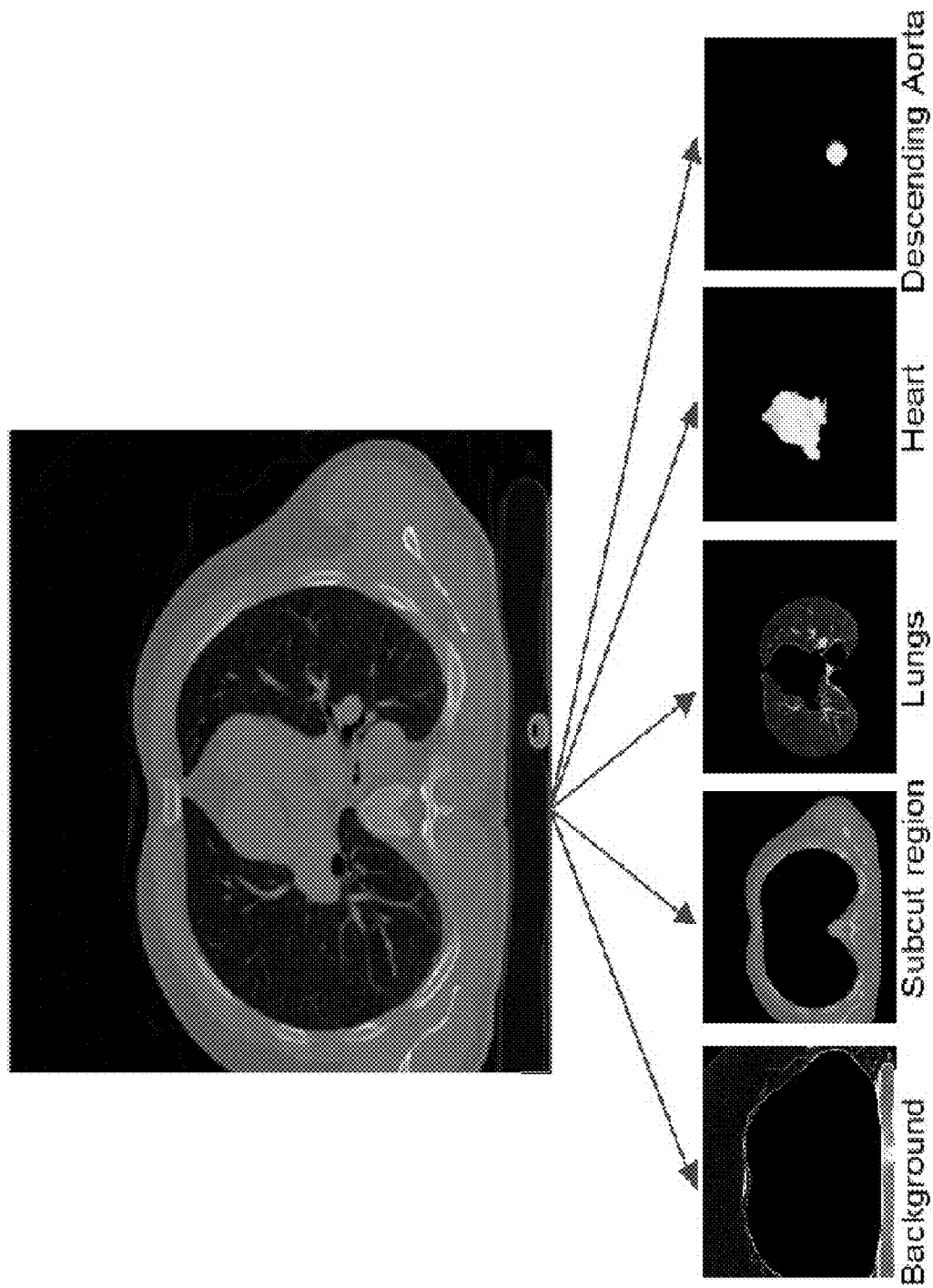
FIG. 45 depict the individual segmentation steps in this method as manually performed.

Our method implemented on a computer or algorithm (AFACT) has been developed based on a training group of patients, and validated in a second group of patients (CT group). Both training and test cases contain examples of CT scans from multiple scanners, with variations of normal anatomy and breathing artifacts, and small cardiac reconstruction field-of-view. FIG. 45 illustrates the individual segmentation steps in this method as manually performed.

Algorithm Description
  Training Phase:
    Estimate tissue-specific distributions using a training data set.
      Step 1
        Compute relevant intensity and texture features for pixels in labeled region of interest (ROI)
      Step 2
        Normalize individual features
      Step 3
        Rank individual features according to their relevance to classification
      Step 4
        Select the optimal feature set
      Step 5
        Compute model parameters for classifiers
    Step 1—Compute Relevant Intensity and Texture Features for Pixels in Labeled Region of Interest (ROI)
    In training images where ROI has been manually labeled as fat, muscle/blood, and bone, we extract Laws' [54] and Gabor texture features [55] for all the labeled pixels in the ROI.
    Step 2—Normalize Individual Features
    To account for scanner and subject variations, the features are normalized to unit range (0, 1) using a linear scaling transformation that excludes outliers [56].
    Step 3—Rank Individual Features According to their Relevance to Classification
    Features contribute differently to classification tasks. We compute the relevance of each feature using Gain Ratio (GR) information theoretic criteria [57]. For a feature $X=[x_1, x_2 \ldots x_n]$ with n samples and corresponding class labels $Y=[y_1, y_2 \ldots y_n]$, GR is computed as $$\frac{H(Y) + H(X) - H(X, Y)}{H(X)}$$

where $H(Y)$ is the class entropy, $H(X)$ is the feature entropy and $H(X,Y)$ is the joint entropy. GR assigns higher values to more discriminating features. The features are then be sorted in descending order of the GR metric. The feature values are be discretized using the minimum description length algorithm [58] prior to the computation of GR metric.
    Step 4—Select the Optimal Feature Set
    We use a forward selection approach [57] to decide on the optimal number of features to use. In forward selection, features are be incorporated into progressively larger subsets while computing the classification accuracy of each subset. The accuracy is computed in a four-fold cross validation in which the data have been divided into four subsets and one set is alternately used for validation while the other three are to be used for training. The subset in which the accuracy is above a given threshold and no longer improves with the addition of more features are accepted as optimal. We use Support Vector Machines (SVM) based classifiers [59], which have been proven to be robust and effective.
    Step 5—Compute Model Parameters for Classifiers
    We combine multiple binary SVM classifiers to solve the multi-tissue segmentation (multi-class) problem, where each binary classifier is trained to differentiate between two tissue types (e.g., fat/muscle, fat/bone, etc). For each classifier, the SVM parameters will be obtained in a four fold cross validation, as in step 4. To combine the binary classifiers, we create a codeword for each class (3 codewords in our case, i.e., 3 rows of the matrix) and codelength=3 (the number of one to one class combinations). Arranging the codewords as rows of matrix, we will define a "coding matrix" M where $M \in \{-1,1\}^{k \times m}$ where k is the code length and m is the number of classes. From the learning perspective, the matrix M is interpreted as m binary learning problems one for each column. Each column defines a partition of classes (coded +1, -1 according to their class membership). The zero entries in the matrix indicate that a particular class is not significant for a given classifier.

TABLE VIII

Error correcting codes for m = 3 classes and with k = 3 code words

| Class | Fat vs. Muscle/Blood | Fat vs. Bone | Muscle/Blood vs. Bone |
|---|---|---|---|
| Fat | 1 | 1 | 0 |
| Muscle/Blood | −1 | 0 | 1 |
| Bone | 0 | −1 | −1 |

Algorithm Description
  Deployment Phase:
  Preprocessing
    Artifact Removal
      Step 5
        Remove equipment-related artifacts such as table and wires
        Determine the heart region using an ontology map
      Step 6
        Use anatomical landmark information to determine upper and lower limits of heart
      Step 7
        Find the outline of the human body automatically in each slice
      Step 8
        Segment the inner-thoracic cavity in each slice
      Step 9
        Segment the lungs in each slice
      Step 10
        Segment the heart and the descending aorta in each slice
      Step 11
        Update the ontology map for every tissue/organ in each slice using labels obtained by segmentation in steps 7-11
  Fat Segmentation
      Step 12
        Compute a binary map using SVM classifiers for all tissue/organ class combinations
      Step 13
        Compute an Error COrrecting Code (ECOC) [60] for each object
      Step 14
        Combine output of all classifiers using Hamming distance
      Step 15
        Combine ontology map information (steps 5-11) and steps 12-14 to quantify pericardial fat
    Step 5
    Many artifacts in the CT image (e.g., the patient table) have intensity distributions very similar to that of the fat tissue. To remove such artifacts, we threshold the original image using a threshold determined automatically using Otsu's [61] method. Then, we perform a largest component analysis on the thresholded image followed by a hole filling morphological operation to remove artifacts such as the table and wires attached to the body. The mask generated by this artifact removal step is used in all the subsequent image analysis steps.

Step 6

The upper and lower boundaries of the heart in CT can be detected using anatomical information. For the upper boundary, the most reliable landmark is the splitting of the pulmonary trunk that takes place a slice or two above the base of the heart. Similarly, the lower boundary of the heart can be approximated 4-5 slices below the first appearance of the liver in the CT scan. We developed ontology-based rules for segmentation based on our anatomical knowledge of location, size, shape, intensity value range and adjacency information of the tissue/organ.

Steps 7-8

To segment the human body boundary and the inner-thoracic cavity, we first threshold the ROI inside the mask generated from Step 5 within the range (−1000 HU, −250 HU) to remove background and air tissue. The thresholded image is smoothed by a 5×5 median filter. We segment the human body boundary and the inner-thoracic cavity by using boundary detection on median filtered image, similar to our preliminary study for visceral fat quantification (C.2). The boundary detection stage (radial gradient sampling) involves populating vectors of points at equiangular intervals radially outwards from the centroid of the preprocessed image. In our preliminary study for visceral fat (C.2), the angular interval of 5 degrees was found to be adequate to find the boundary. Each of these vectors is traversed with a first order gradient filter kernel to mark the points where there is a change from the background to ROI. Assuming that the preprocessed image consists only of somatic tissue, the outermost gradient point along any given vector should lie on the external boundary of the human body, while the second outermost point should lie on the external boundary of the lungs. We combine the outermost points to form the contour to generate a closed polygon, which is the human body ROI for the CT image. We get the inner-thoracic cavity ROI by generating a closed polygon for the second outermost points.

Steps 9-11

The lungs are segmented automatically in a 2D slice using an experimentally determined lung threshold value (−400 HU) inside the inner-thoracic cavity. We obtain the initial heart region as the area between the segmented lung regions. We use ontology-based rules on the initial heart region to segment descending aorta in the first slice and track the descending aorta (seen as a circle) in all the slices. We update the ontological map all tissues/organ in each slice using the labels generated in steps 7-11.

Steps 12-15

First, for each of the three class combinations we compute a binary map for all the objects using the SVM models obtained from the training phase. As a result of the outputs of the three binary classifiers, a code is obtained for each object in the test set. This code is compared with the base codewords for each class defined in the matrix M, and the object is assigned to the class with "closest" codeword using the largest minimum hamming decoding distance. The ontology map information determined in steps 5-11 are used to localize and guide the binary classifiers. Finally, we quantify pericardial fat in the heart region. The program reports the pericardial fat volume in cc, as well as the pericardial fat ratio, defined as the ratio of pericardial fat volume to cardiac volume, as in our preliminary study (C.1). We will also weight the pericardial fat volume with the thoracic size.

G. Literature Cited in this Section

The following references were cited in this section:

[1] American Heart Association, "2002 Heart and Stroke Statistical Update," 2002.

[2] S. Yusuf, S. Reddy, S. Ounpuu, and S. Anand, "Global burden of cardiovascular diseases: part I: general considerations, the epidemiologic transition, risk factors, and impact of urbanization," *Circulation*, vol. 104, pp. 2746-53, 2001.

[3] R. J. Myerburg. A. Interian, Jr., R. M. Mitrani, K. M. Kessler, and A. Castellanos, "Frequency of sudden cardiac death and profiles of risk," *Am J Cardiol*, vol. 80, pp. 10F-19F, 1997.

[4] R. Virmani, A. P. Burke, and A. Farb, "Sudden cardiac death," *Cardiovasc Pathol*, vol. 10, pp. 211-8, 2001.

[5] D. S. Bennan, Shaw L. J., Germano G., "Nuclear Cardiology," in *Hurst's The Heart*, A. R. Fuster V, O'Rourke R A, Roberts R, King S B, Wellens H J J, Ed. New York, N.Y.: McGraw-Hill Companies, 2000, pp. 525-565.

[6] American Heart Association, *Heart and Stroke Facts*, 2003.

[7] M. Naghavi, P. Libby, E. Falk, S. W. Casscells, S. Litovsky, J. Rumberger, J. J. Badimon, C. Stefanadis, P. Moreno, G. Pasterkamp, Z. Fayad, P. H. Stone, S. Waxman. P. Raggi, M. Madjid, A. Zarrabi, A. Burke, C. Yuan, P. J. Fitzgerald, D. S. Siscovick, C. L. de Korte, M. Aikawa, K. E. Juhani Airaksinen, G. Assmann, C. R. Becker, J. H. Chesebro, A. Farb, Z. S. Galis, C. Jackson, I. K. Jang, W. Koenig, R. A. Lodder, K. March, J. Demirovic, M. Navab, S. G. Priori, M. D. Rekhter, R. Bahr, S. M. Grundy, R. Mehran, A. Colombo, E. Boerwinkle, C. Ballantyne, W. Insull, Jr., R. S. Schwartz, R. Vogel, P. W. Serruys, G. K. Hansson, D. P. Faxon, S. Kaul, H. Drexler, P. Greenland, J. E. Muller, R. Virmani, P. M. Ridker, D. P. Zipes, P. K. Shah, and J. T. Willerson, "From vulnerable plaque to vulnerable patient: a call for new definitions and risk assessment strategies: Part I." Circulation, vol. 108, pp. 1664-72., 2003.

[8] M. Naghavi, P. Libby, E. Falk, S. W. Casscells, S. Litovsky, J. Rumberger, J. J. Badimon, C. Stefanadis, P. Moreno, G. Pasterkamp, Z. Fayad, P. H. Stone, S. Waxman, P. Raggi, M. Madjid, A. Zarrabi, A. Burke, C. Yuan, P. J. Fitzgerald, D. S. Siscovick, C. L. de Korte, M. Aikawa, K. E. Airaksinen, G. Assmann, C. R. Becker, J. H. Chesebro, A. Farb, Z. S. Galis, C. Jackson, I. K. Jang, W. Koenig, R. A. Lodder, K. March, J. Demirovic, M. Navab, S. G. Priori, M. D. Rekhter, R. Bahr. S. M. Grundy, R. Mehran, A. Colombo. E. Boerwinkle, C. Ballantyne, W. Insull. Jr. R. S. Schwartz, R. Vogel, P. W. Serruys, G. K. Hansson, D. P. Faxon, S. Kaul, H. Drexler. P. Greenland, J. E. Muller, R. Virmani, P. M. Ridker, D. P. Zipes, P. K. Shah, and J. T. Willerson, "From vulnerable plaque to vulnerable patient: a call for new definitions and risk assessment strategies: Part II," Circulation, vol. 108, pp. 1772-8, 2003.

[9] H. K. Eltzschig and R. Ehlers, "Noninvasive tests in patients with stable coronary artery disease," *N Engl J Med, vol.* 345, pp. 1351, 2001.

[10] A. S. Agatston, W. R. Janowitz, F. J. Hildner, N. R. Zusmer, M. Viamonte, Jr., and R. Detrano, "Quantification of coronary artery calcium using ultrafast computed tomography," *J Am Coll Cardiol*, vol. 15, pp. 827-32, 1990.

[11] A. Schmermund, S. Mohlenkamp, and R. Erbel, "The latest on the calcium story," *Am J Cardiol*, vol. 90, pp. 12L-14L, 2002.

[12] T. Callister, B. Cooil, S. Raya, N. Lippolis, D. Russo, and P. Raggi, "Coronary artery disease: improved reproducibility of calcium scoring with an electron-beam CT volumetric method," *Radiology*, vol. 208, pp. 807-814, 1998.

[13] L. Shaw, P. Raggi, E. Schisterman, D. Berman, and T. Callister, "Prognostic value of cardiac risk factors and coronary artery calcium screening for all-cause mortality.," *Radiology*, vol. 228, pp. 826-33, 2003.

[14] Y. Arad, K. J. Goodman, M. Roth, D. Newstein, and A. D. Guerci, "Coronary calcification, coronary disease risk factors, C-reactive protein, and atherosclerotic cardiovascular disease events: the St. Francis Heart Study," *J Am Coll Cardiol*, vol. 46, pp. 158-65, 2005.

[15] J. A. Rumberger, "Tomographic (plaque) imaging: state of the art," *Am J Cardiol*, vol. 88, pp. 66E-69E., 2001.

[16] G. L. Raff, M. J. Gallagher, W. W. O'Neill, and J. A. Goldstein, "Diagnostic accuracy of noninvasive coronary angiography using 64-slice spiral computed tomography," *J Am Coll Cardiol*, vol. 46, pp. 552-7., 2005.

[17] D. S. Berman, R. Hachamovitch, L. J. Shaw, J. D. Friedman, S. W. Hayes, L. E. Thomson, D. S. Fieno, G. Germano, P. Slomka, N. D. Wong, X. Kang, and A. Rozanski, "Roles of Nuclear Cardiology, Cardiac Computed Tomography, and Cardiac Magnetic Resonance: Assessment of Patients with Suspected Coronary Artery Disease," *J Nucl Med*, vol. 47, pp. 74-82., 2006.

[18] D. S. Berman, X. Kang, E. F. Schisterman, J. Gerlach, P. B. Kavanagh, J. S. Areeda, T. Sharir, S. W. Hayes, L. J. Shaw, H. C. Lewin, J. D. Friedman, R. Miranda, and G. Germano, "Serial changes on quantitative myocardial perfusion SPECT in patients undergoing revascularization or conservative therapy," *J Nucl Cardiol*, vol. 8, pp. 428-37, 2001.

[19] D. S. Berman, N. D. Wong, H. Gransar, R. Miranda-Peats, J. Dahlbeck, S. W. Hayes, J. D. Friedman, X. Kang, D. Polk, R. Hachamovitch, L. Shaw, and A. Rozanski, "Relationship between stress-induced myocardial ischemia and atherosclerosis measured by coronary calcium tomography," *J Am Coll Cardiol*, vol. 44, pp. 923-30, 2004.

[20] S. M. Grundy, "Primary prevention of coronary heart disease: integrating risk assessment with intervention," *Circulation*, vol. 100, pp. 988-98, 1999.

[21] P. W. Wilson, R. B. D'Agostino, D. Levy, A. M. Belanger, H. Silbershatz, and W. B. Kannel, "Prediction of coronary heart disease using risk factor categories," *Circulation*, vol. 97, pp. 1837-47, 1998.

[22] "Executive Summary of The Third Report of The National Cholesterol Education Program (NCEP) Expert Panel on Detection, Evaluation, And Treatment of High Blood Cholesterol In Adults (Adult Treatment Panel III)," *Jama*, vol. 285, pp. 2486-97, 2001.

[23] P. M. Ridker, M. Cushman, M. J. Stampfer, R. P. Tracy, and C. H. Hennekens, "Inflammation, aspirin, and the risk of cardiovascular disease in apparently healthy men." *N Engl J Med*, vol. 336, pp. 973-9, 1997.

[24] P. M. Ridker, C. H. Hennekens, J. E. Buring, and N. Rifai, "C-reactive protein and other markers of inflammation in the prediction of cardiovascular disease in women," *N Engl J Med*, vol. 342, pp. 836-43, 2000.

[25] P. M. Ridker, N. Rifai, L. Rose, J. E. Buring, and N. R. Cook, "Comparison of C-reactive protein and low-density lipoprotein cholesterol levels in the prediction of first cardiovascular events," *N Engl J Med*, vol. 347, pp. 1557-65, 2002.

[26] V. Pasceri, J. T. Willerson, and E. T. Yeh, "Direct proinflammatory effect of C-reactive protein on human endothelial cells," *Circulation*, vol. 102, pp. 2165-8, 2000.

[27] L. J. Shaw, P. Raggi, E. Schisterman, D. S. Berman, and T. Q. Callister. "Prognostic value of cardiac risk factors and coronary artery calcium screening for all-cause mortality," *Radiology*, vol. 228, pp. 826-33, 2003.

[28] J. A. Rumberger, D. B. Simons, L. A. Fitzpatrick, P. F. Sheedy, and R. S. Schwartz, "Coronary artery calcium area by electron-beam computed tomography and coronary atherosclerotic plaque area. A histopathologic correlative study," *Circulation*, vol. 92, pp. 2157-62, 1995.

[29] V. R. Huang H, Younis H, Burke A P, Kamm R D, Lee R T, "The impact of calcification on the biomechanical stability of atherosclerotic plaques," *Circulation*, vol. 103, pp. 1051-6, 2001.

[30] E. R. Schmermund A, "Unstable coronary plaque and its relation to coronary calcium," *Circulation*, vol. 104, pp. 1682-7, 2001.

[31] A. J. Taylor, A. P. Burke, P. G. O'Malley, A. Farb, G. T. Malcom, J. Smialek, and R. Virmani, "A comparison of the Framingham risk index, coronary artery calcification, and culprit plaque morphology in sudden cardiac death," *Circulation*, vol. 101, pp. 1243-8, 2000.

[32] A. J. Taylor, C. N. B. Merz, and J. E. Udelson, "Executive Summary—Can Atherosclerosis Imaging Techniques Improve the Detection of Patients at Risk for Ischemic Heart Disease?," *J Am Coll Cardiol*, vol. 41, pp. 1860-3, 2003.

[33] J. B. Meigs, "Metabolic syndrome: in search of a clinical role," *Diabetes Care*, vol. 27, pp. 2761-3, 2004.

[34] K. G. Alberti, P. Zimmet, and J. Shaw, "The metabolic syndrome—a new worldwide definition," *Lancet*, vol. 366, pp. 1059-62, 2005.

[35] H. M. Lakka, D. E. Laaksonen, T. A. Lakka, L. K. Niskanen, E. Kumpusalo, J. Tuomilehto, and J. T. Salonen. "The metabolic syndrome and total and cardiovascular disease mortality in middle-aged men," *Jama*, vol. 288, pp. 2709-16, 2002.

[36] A. M. McNeill, W. D. Rosamond, C. J. Girman, S. H. Golden, M. I. Schmidt. H. E. East, C. M. Ballantyne, and G. Heiss, "The metabolic syndrome and 11-year risk of incident cardiovascular disease in the atherosclerosis risk in communities study," *Diabetes Care*, vol. 28, pp. 385-90, 2005.

[37] L. Citrome, "Metabolic syndrome and cardiovascular disease," *J Psychopharmacol*, vol. 19, pp. 84-93, 2005.

[38] B. L. Wajchenberg, D. Giannella-Neto, M. E. da Silva, and R. F. Santos, "Depot-specific hormonal characteristics of subcutaneous and visceral adipose tissue and their relation to the metabolic syndrome," *Horm Metab Res*, vol. 34, pp. 616-21, 2002.

[39] B. L. Wajchenberg, "Subcutaneous and visceral adipose tissue: their relation to the metabolic syndrome," *Endocr Rev*, vol. 21, pp. 697-738, 2000.

[40] B. Wajchenberg, D. Giannella-Neto, S. M. da, and R. Santos, "Depot-specific hormonal characteristics of subcutaneous and visceral adipose tissue and their relation to the metabolic syndrome.," *Horm Metab Res*, vol. 34, pp. 616-21, 2002.

[41] R. Weiss, S. Dufour, S. E. Taksali, W. V. Tamborlane, K. F. Petersen, R. C. Bonadonna, L. Boselli, G. Barbetta, K. Allen, F. Rife, M. Savoye, J. Dziura, R. Sherwin, G. I. Shulman, and S. Caprio, "Prediabetes in obese youth: a syndrome of impaired glucose tolerance, severe insulin resistance, and altered myocellular and abdominal fat partitioning," *Lancet*, vol. 362, pp. 951-7., 2003.

[42] H. Kvist, B. Chowdhury, U. Grangard. U. Tylen, and L. Sjostrom. "Total and visceral adipose-tissue volumes derived from measurements with computed tomography in adult men and women: predictive equations," *Am J Clin Nutr*, vol. 48, pp. 1351-61., 1988.

[43] F. L. Thaete, S. R. Colberg, T. Burke, and D. E. Kelley, "Reproducibility of computed tomography measurement of visceral adipose tissue area," *Int J Obes Relat Metab Disord*, vol. 19, pp. 464-7, 1995.

[44] B. Wajchenberg, "Subcutaneous and visceral adipose tissue: their relation to the metabolic syndrome.," *Endocr Rev*, vol. 21, pp. 697-738, 2000.

[45] G. L. Wheeler, R. Shi, S. R. Beck, C. D. Langefeld, L. Lenchik, L. E. Wagenknecht, B. I. Freedman, S. S. Rich, D. W. Bowden, M. Y. Chen, and J. J. Carr, "Pericardial and visceral adipose tissues measured volumetrically with computed tomography are highly associated in type 2 diabetic families," *Invest Radiol*, vol. 40, pp. 97-101., 2005.

[46] R. Taguchi, J. Takasu, Y. Itani, R. Yamamoto, K. Yokoyama, S. Watanabe, and Y. Masuda, "Pericardial fat accumulation in men as a risk factor for coronary artery disease," *Atherosclerosis*, vol. 157, pp. 203-9, 2001.

[47] J. P. Despres, "Abdominal obesity as important component of insulin-resistance syndrome," *Nutrition*, vol. 9, pp. 452-9., 1993.

[48] B. Lamarche, "Abdominal obesity and its metabolic complications: implications for the risk of ischaemic heart disease," *Coron Artery Dis*, vol. 9, pp. 473-81., 1998.

[49] T. Yoshizumi, T. Nakamura, M. Yamane, A. H. Islam, M. Menju, K. Yamasaki, T. Arai, K. Kotani, T. Funahashi, S. Yamashita, and Y. Matsuzawa, "Abdominal fat: standardized technique for measurement at CT," *Radiology*, vol. 211, pp. 283-6., 1999.

[50] L. S. Parsons, "Reducing bias in a propensity score matched-pair sample using greedy matching techniques," *Proceedings of the Twenty-Sixth Annual SAS® Users Group International Conference*, pp. 214-216, 2001.

[51] A. Pednekar, Bandekar A. N., Kakadiaris I. A., Naghavi M., "Automatic segmentation of abdominal fat in CT," *Proceedings of the IEEE Workshop in Applications of Computer Vision*, Colorado, 2005.

[52] A. N. Bandekar, Naghavi. M., Kakadiaris I. A., "Performance evaluation of abdominal fat burden quantification in CT," 2005.

[53] A. S. Pednekar and I. A. Kakadiaris, "Image Segmentation based on fuzzy connectedness using dynamic weights." *IEEE Transactions in Image Processing*, 2005.

[54] K. Laws, "Texture Image Segmentation," vol. PhD: USC, 1980.

[55] B. Manjunath and W. Ma, "Texture features for browsing and retrieval of image data," *IEEE Transactions on Pattern Analysis and Machine Intelligence*, vol. 18, pp. 837-842, 1996.

[56] S. Aksoy and R. Haralick, "Feature normalization and likelihood-based similarity measures for image retrieval," *Pattern Recognition Letters*, vol. 22, pp. 563-582, 2001.

[57] I. Guyon and A. Elisseeff, "An introduction to variable and feature selection," *Journal of Machine Learning Research*, vol. 3, pp. 1157-1182, 2003.

[58] U. Fayyad and K. Irani, "On the handling of continuous-valued attributes in decision tree generation," *Machine Learning*, vol. 8, pp. 87-102, 1992.

[59] V. Vapnik, *The Nature of Statistical Learning Theory*: Springer-Verlag, 2000.

[60] T. G. Dietterich and G. Bakiri, "Solving Multiclass Learning Problems via Error-Correcting Output Codes," *Journal of Artificial Intelligence Research*, vol. 2, pp. 263-286, 1995.

[61] N. Otsu, "A Threshold Selection Method from Gray-Level Histograms," *IEEE Transactions on Systems, Man, and Cybernetics*, vol. 9, pp. 62-66, 1979.

[62] J. A. Hanley and B. J. McNeil. "The meaning and use of the area under a receiver operating characteristic (ROC) curve," *Radiology*, vol. 143, pp. 29-36, 1982.

[63] J. A. Hanley and B. J. McNeil, "A method of comparing the areas under receiver operating characteristic curves derived from the same cases," *Radiology*, vol. 148, pp. 839-43, 1983.

[64] R. Hachamovitch, D. S. Berman, H. Kiat, I. Cohen, J. A. Cabico, J. Friedman, and G. A. Diamond, "Exercise myocardial perfusion SPECT in patients without known coronary artery disease: incremental prognostic value and use in risk stratification." *Circulation*, vol. 93, pp. 905-14., 1996.

[65] R. Hachamovitch, D. S. Berman, L. J. Shaw, H. Kiat, I. Cohen, J. A. Cabico, J. Friedman, and G. A. Diamond, "Incremental prognostic value of myocardial perfusion single photon emission computed tomography for the prediction of cardiac death: differential stratification for risk of cardiac death and myocardial infarction," *Circulation*, vol. 97, pp. 535-43., 1998.

Automatic Segmentation of Abdominal Fat from Ct Data

Abdominal visceral fat accumulation is one of the most important cardiovascular risk factors. Currently, Computed Tomography and Magnetic Resonance images are manually segmented to quantify abdominal fat distribution. The manual delineation of subcutaneous and visceral fat is labor intensive, time consuming, and subject to inter- and intraobserver variability. An automatic segmentation method would eliminate intra- and inter-observer variability and provide more consistent results. In this section, we present a hierarchical, multi-class, multi-feature, fuzzy affinity-based computational framework for tissue segmentation in medical images. We have applied this framework for automatic segmentation of abdominal fat. An evaluation of the accuracy of our method indicates bias and limits of agreement comparable to the inter-observer variability inherent in manual segmentation.

1. Introduction

A recent survey reveals that over 64% of Americans are overweight or obese [3]. The presence of excess fat in the abdomen (out of proportion to the total body fat) is an independent predictor of morbidity. Computed Tomography (CT) and Magnetic Resonance Imaging (MRI) are often used to quantify abdominal fat distribution. CT is preferred over MRI because it provides good contrast between fat and non-fat tissues and it is less expensive. In current clinical practice, quantification of the fat tissue is performed manually by an expert who has a good knowledge of the anatomy. It is a very time consuming and cumbersome process subject to inter and intra-observer variations. Thus, the development of a computer-assisted method which provides unbiased and consistent results with minimal human intervention is highly desirable.

The normal CT attenuation ranges for the fat tissues is defined as the interval within (−190<Hu<−30) [12]. However, the average Hounsfield units (Hu) for the fat tissue varies across subjects and it also depends on the CT scanner [12]. Thus, assessment of fat distribution requires a case-specific flexible attenuation range. Recent techniques estimate the abdominal fat distribution using a threshold within the mean plus-minus two standard deviations [12]. This method, called flexible threshold method (FTM), is independent of the relative spatial location of the pixel with the neighborhood pixels. As a result, this segmentation using an intensity-based threshold alone is not accurate. The Fuzzy Connectedness-Based Image Segmentation frame-work developed by Udupa and his collaborators [14] effectively captures the fuzzy "hanging togetherness" (perception of an object region in spite of heterogeneity of scene intensity) of image elements specified by their strength of connectedness. This framework was further extended to take into consideration object scale [11], relative strength of connectedness [9], and multiple objects [10]. A hybrid segmentation method [13] that combines fuzzy connectedness segmentation, Voronoi diagram classification, and de-formable model based smoothing algorithms was applied for the segmentation of adipose tissue from whole body MRI scans. In our previous work, we have presented a composite fuzzy affinity using dynamic weights for the affinity components [6].

In this section, we present an automatic tissue segmentation method which combines the intensity and texture information with local "hanging togetherness" within a tissue class. The fuzzy connectedness constraint for the object extraction in the frameworks presented in [6, 7, 14] is relaxed to allow global segmentation. Thus, instead of applying a space-invariant global threshold value, our computational framework adapts the threshold value locally to ac-count for the local "hanging togetherness" of the tissue to be segmented. Specifically, we present a hierarchical, multi-class, multi-feature, fuzzy affinity-based framework for tissue segmentation. The global class affinity is computed based on discrepancy measures of the given image element (spatial element—spel) pair with respect to the learned distributions of the prominent and neighboring objects in the image. We use the Mahalanobis metric as the discrepancy measure. The local fuzzy affinity between two spels is computed based on their spatial nearness as well as the similarity of their intensity and texture-based features. The Mahalanobis metric is used to compute the similarity of spels in the intensity and texture-based feature space. The most discriminant combination of texture features for specific object regions and for a specific modality are determined in the training phase of our framework. Specifically, during the training phase we compute the first order and second order statistics at various scales covering the entire scale spectrum of the image. The Fisher's criterion is used to quantize the discriminating power of combinations of texture features for the tissue classes of interest. The most discriminating feature combinations are determined based of the cumulative discriminating power of each feature.

The remainder of the section is organized as follows. Section 2 details the formulation of our method. In Section 3, we describe abdominal fat segmentation in CT images using our framework. In Section 4, we present results from our method and a comparison with previous methods.

2. Methods 2.1. Hierarchical Multi-Class Multi-Feature Fuzzy Affinity

In this section, we review our formulation of hierarchical, multi-class, multi-feature, fuzzy affinity using a required set of terminology, definitions, and framework introduced in [14]. An image is considered as a two-dimensional Euclidean space $R^2$ subdivided into spatial elements (spels) called pixels. A digital space $Z^2$, where the coordinates of pixel correspond to a point, is the set of all pixels of $R^2$. For any fuzzy relationship p, the strength of p between c and d is represented by a membership function $\mu_p(c, d)$. If a fuzzy relation $\alpha=\{((c,d),\mu_\alpha(c,d))|c,d \in Z^2\}$ is reflexive and symmetric, it is said to be a fuzzy spel adjacency, which de-scribes the spatial relationship between the two spels. For any pixels $c,d \in Z^2$, $\mu_\alpha(c,d)$ is assumed to be a hard adjacency relation, such that:

$$\mu_\alpha(c,d)=(1 \text{ iff} \|c-d\| \leq 1, 0 \text{ otherwise}),$$

where $\|c-d\|$ represents the Euclidean distance between c and d. The pair $(Z^2,\alpha)$, where a is a fuzzy spel adjacency is called a fuzzy digital space. The concept of fuzzy digital space characterizes the underlying digital grid system independent of any image related concepts. A scene over a fuzzy digital space $(Z^2,\alpha)$ is a pair $C=(C,f)$ where $C=\{c|-b_j \leq c_j \leq b_j\}$ for some $b \in Z^2$ is a finite two-dimensional rectangular array of pixels, f is a scene intensity function whose domain is C, called the scene domain, and the range is a set of integers [L,H]. If C is a scene over $Z^2$ in which the range of f is $\{0,1\}$, then C is called a binary scene over $(Z^2,\alpha)$. In an object class identification process the aim is to capture the local "hanging togetherness" of pixels.

2.1.1 Local Fuzzy Spel Affinity

Any fuzzy relation r. in C is said to be a fuzzy spel affinity in C if it is reflexive and symmetric. We define the local fuzzy spel affinity ($\mu_\kappa$) to consist of three primary components:

1) an object feature intensity component ($\mu_\varphi$), 2) an intensity homogeneity component ($\mu_\psi$), and 3) a texture feature component ($\mu_\phi$), as follows:

$$\mu_\kappa(c,d)=\mu_\alpha(c,d)g(\mu_\varphi(c,d),\mu_\psi(c,d),\mu_\phi(c,d)) \quad (1)$$

We combine the affinity components to form a composite local fuzzy spel affinity. Thus, the fuzzy relation κ in $Z^2$ indicates the degree of local "hanging togetherness" of pixels c and d in the vector space of feature vectors:

$$x = \left[\frac{1}{2}(f(c)+f(d)), f(c)-f(d), \frac{1}{2}(t(c)+t(d))\right]^T \quad (2)$$

where f(c) and f(d) are the image intensities, and t(c) and t(d) are the texture features at pixels c and d. The similarity of the pixels' feature vectors is computed using the Mahalanobis metric:

$$m_d^2 = (x_{(c \to d)} - \bar{x}_{(c \to d)})^T S_{x_{(c \to d)}}^{-1} (x_{(c \to d)} - \bar{x}_{(c \to d)}) \quad (3)$$

where $x_{(c \to d)}$, $\bar{x}_{(c \to d)}$, $S_{(c \to d)}$ are the feature vector, the mean feature vector, and the covariance matrix in the direction from c to d. The bias in intensity in a specific direction is thus accounted for by allowing different levels and signs of intensity homogeneities in different directions of adjacency. Thus, this formulation accounts for different levels of the change in intensity values in the horizontal (east, west) or vertical (north, south) directions. The advantage of using the Mahalanobis metric is that it weighs the differences in various feature dimensions by the range of variability. Another advantage of using the Mahalanobis metric for discrimination is that the distances are computed in units of standard deviation from the group mean. This allows us to assign a statistical probability to that measurement. The local fuzzy spel affinity is computed as:

$$\mu_\kappa(c, d) = \frac{1}{1 + m_d} \quad (4)$$

to ensure $\mu_\kappa(c,d) \in Z^2 \rightarrow [0,1]$ and it is reflexive and symmetric. Thus, $\mu_\kappa(c,d)$ defines th probability of the pixel pair belonging to the target object class. The thresh-old for the class identifier can be set based on the probability distribution of a specific feature space for a particular application.

2.1.2 Global Class Affinity

In our hierarchical fuzzy affinity, the local pixel affinities are assigned only if the probability of c and d belonging to the neighboring objects' classes is much less than 0.01. The neighboring objects are defined as the objects with common boundaries in Euclidean space. For a given pixel pair (c,d), we compute the discrepancy measure with respect to the learned distributions of neighboring classes. We compute the discrepancy measure of a pixel pair from a known class in terms of its Mahalanobis distance. Then, the minimum discrepancy measure which provides the probability of pixel pair belonging to a certain class is given by:

$$J(c, d) = \min_{1 \le i \le b} m_d(c, d) \quad (5)$$

where b is the number of neighboring classes to the target object. If $J(c,d)<3$ for any neighboring class distribution other than the target object class then the local pixel affinity $\mu_\kappa(c,d)$ is set to zero. Otherwise, its local pixel affinity is computed as described in Section 2.1.1.

In summary, our image segmentation framework consists of the following steps:

I. Training Phase
A. Estimate object-specific feature distributions using a training data set.
   Step 1: Compute relevant features for domain specific objects.
   Step 2: Compute the most discriminant features.
   Step 3: Construct a template (mean shape) using the landmark points in the training images for the seed region (Not applicable in all domains).
II. Deployment Phase
B. Initialize the target object seed region.
   Step 4: Compute the target object seed pixel using do-main specific knowledge.
C. Compute the fuzzy connectedness-based object.
   Step 5: Compute global class affinity for a given spel.
   Step 6: If the spel is not determined to be a member of non-target objects, then compute local fuzzy affinity.
   Step 7: Compute the global object affinity.
   Step 8: Compute the fuzzy extent of the target object.

3. Abdominal Fat Segmentation in Ct Images

Figure 46:
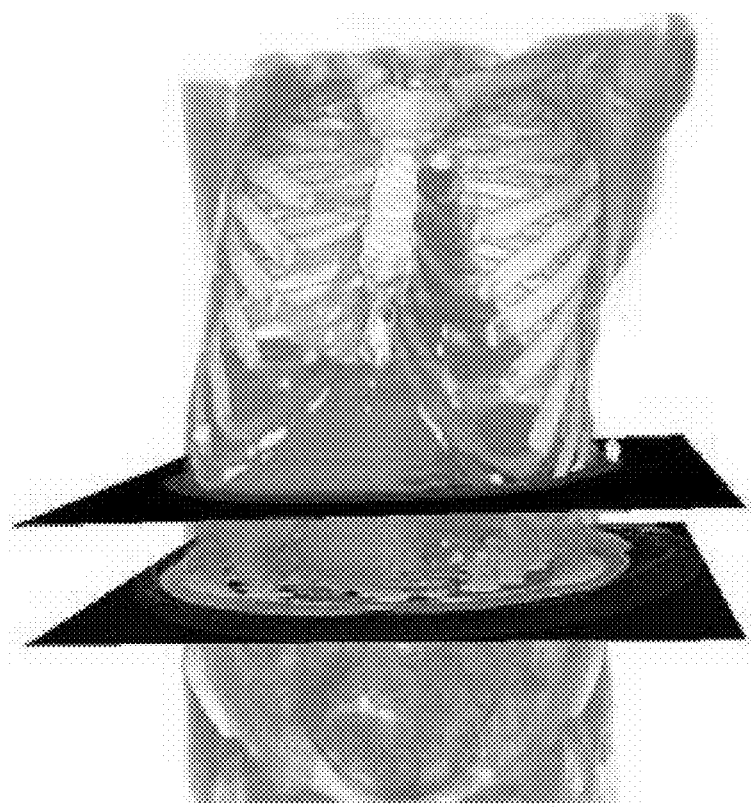
FIG. 46 depicts a visualization of a subject's CT data.

We apply our hierarchical, multi-class, multi-feature, fuzzy affinity framework for the automatic segmentation of the abdominal fat from CT images. The abdominal fat consists of visceral, retroperitoneal, and subcutaneous fat. FIG. 46 depicts a 3D visualization of a subjects's CT data with two CT slices depicted as orthoslices in a volume.

3.1. Experimental Data

The study population consisted of 80 randomly chosen subjects with 5 CT scan images per patient. The data were obtained by a CT abdominal scan between the fourth and fifth lumbar vertebrae (L4-L5) (i.e., at the level of umbilicus). Scanning was performed at 130 kV and 200 mA and the field of view ranged from 30 to 50 cm. Slice thickness was 6.0 mm in all subjects. We divided the data into 40 training and 40 test data sets.

3.2. Steps 1-2: Training Phase

The average CT value for the fat tissue is well separated from the rest of the tissue. However, the variance of the average CT value for fat for a specific subject and for a specific scanner is unknown. In addition, the intensity-based discrimination of fat from non-fat tissue does not capture the local spatial "hanging togetherness" of the fat. We use the texture features of the fat and its neighboring non-fat tissue types to increase the discriminating power. Specifically, first we computed Laws' features [4] and Gabor's texture features [5] for the abdominal CT images. In the training phase, we used 25 Laws' features and a Gabor filter bank consisting of 4 scales and 6 orientations. We manually la-belled in the 200 slices the regions of fat, nonfat, and back-ground. We extracted pixel features for the classes fat and non-fat from the feature images. The most discriminating feature combinations were determined according to their cumulative discriminating power. We found that spot-spot (ss) and spot-level (sl) Laws' features are the most discriminating. The convolution of spot with spot, and spot with level kernels provides the ss and sl filters. Furthermore, the combination of intensity and § features provided the highest discrimination between fat and non-fat tissues. Thus, our feature vector consists of the pixel pair intensity and the ś Laws' feature in a neighborhood of 5×5 pixels. Since the average CT values for the fat tissue are well separated from other tissues we can separate the non-fat distribution into two distributions (−190<Hu<−30) [12]. These distributions were used to find the probability of pixel pair belonging to the non-fat class.

3.3. Steps 3-4: Automatic Seed Initialization

During the deployment phase of our framework, we obtain the sample statistics of a tissue by choosing a seed point and computing sample statistics around it. Selection of the seed point is very critical. We obviate the need of a manual seed selection by automatic seed initialization using Active Shape Models (ASM) [2].
Template Construction
We select the seed using a sub-cutaneous fat template. To that end, we construct a Point Distribution Model for selected landmark points around the subcutaneous fat area. We first threshold the original images within the threshold range of (−190<Hu<−30) to obtain the fat region. Then, we label (n=36) landmark points −($x_1$,$y_1$), ($x_2$,$y_2$), ..., ($x_n$, $y_n$)—in each binary image. We create a subcutaneous fat template by selecting 36 landmark points based on the anatomy of the abdominal region. Landmarks points are selected based on the curvature of the boundary of the subcutaneous fat area. Each template is represented as:

$$x = \{x_1, x_2 x_n, y_1, y_2, \ldots y_n\}^T \quad (6)$$

Corresponding points are then aligned to remove affine differences in the images using Procrustes analysis [8], before obtaining the mean shape $$\bar{x} = \frac{1}{s}\sum_{i=1}^{s} x_i.$$

Figure 47:
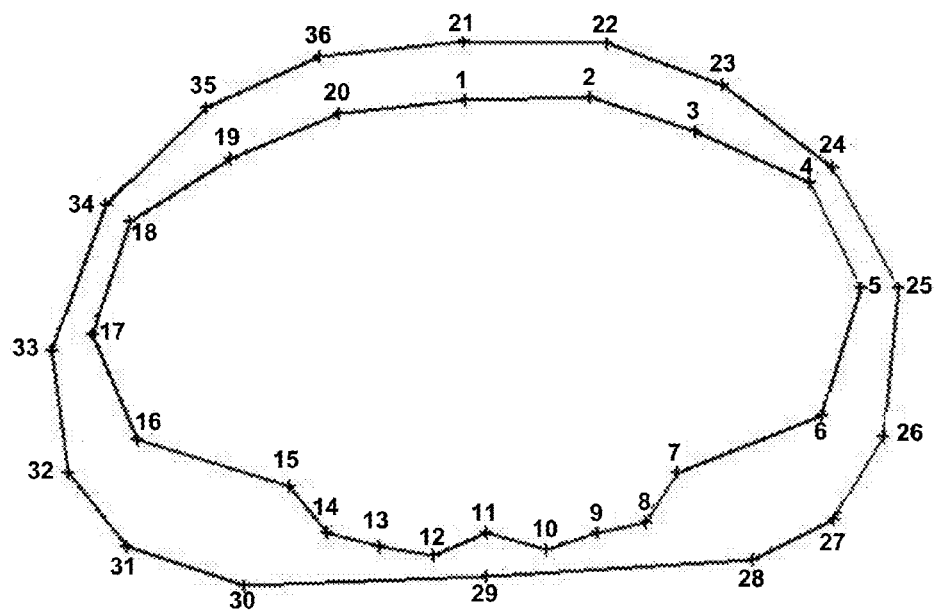
FIG. 47 depicts a mean shape of the subcutaneous fat template.

FIG. 47 depicts the mean shape of the subcutaneous fat template. To obtain the typical modes of variation of the shape, Principal Component Analysis is applied and only the first t eigenvectors corresponding to the largest t eigenvalues accounting for a specified percentage of the variation (95%) are retained. Any shape in the class can thus be represented as:

$$x = \bar{x} + \Phi b$$

where b is a vector of weights for each variation mode and $\Phi$ is the matrix consisting of t principal modes of variation. To construct a gray-level appearance model, we obtain a gray level profile of intensities along the normal to each landmark. Then, the mean normalized derivative as well as the covariance of each profile is computed across all images.

Seed Initialization

Figure 48:
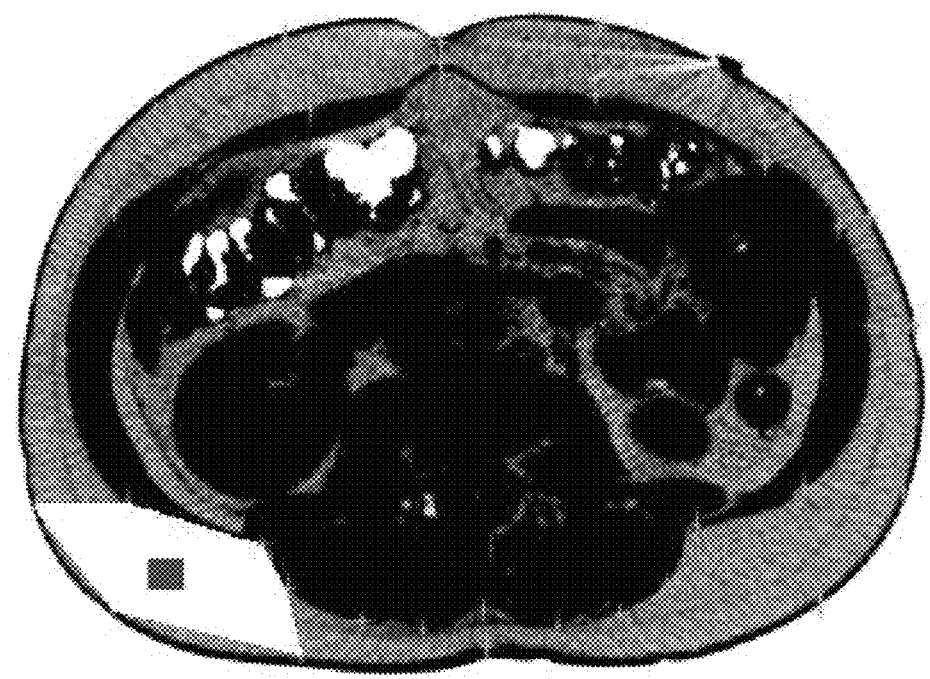
FIG. 48 depicts an automatic seed initialization using ASM fitting.

During the deployment phase of our framework, we select the seed region by fitting the subcutaneous fat template to the thresholded CT image. Specifically, the seed point is chosen as the centroid of the region enclosed by the landmarks 14, 15, 16, 30, 31, and 32. FIG. 48 depicts the seed point and the location of the 36 land-marks after ASM fitting. Next, the subcutaneous and visceral fat is segmented by employing Steps 5-8 in our frame-work.

4. Results and Discussion

We evaluated the results of our method (UHAFS: University of Houston Automatic Fat Segmentation) against expert manual segmentations of subcutaneous and visceral fat for 20 subjects. Experienced physicians/radiologists delineated the fat region in the CT slices which were used as gold standard. The qualitative results of our algorithm for Subjects 1-5 are depicted in FIGS. 50A-H and FIGS. 52A-L. We evaluated the results of our algorithm by computing the three measures of accuracy recommended by [13]. Specifically, we compute the false negatives (FN), false positives (FP), true negatives (TN), and true positives (TP) by computing the number of pixels that were classified as the background and the region of interest (ROI), both correctly and incorrectly. The true positive rate is defined as the percentage of correctly classified object (i.e., fat tissue) pixels to the total number of object pixels. The true negative rate is defined as the percentage of correctly identified non-object (i.e., non-fat tissue and back-ground) to the total number of non-object pixels. Accuracy is defined as the percentage of correctly classified pixels (in object and non-object) with respect to the total number of pixels in the images. Accuracy denotes the degree to which the segmentation agrees with the ground truth.

Figure 49:
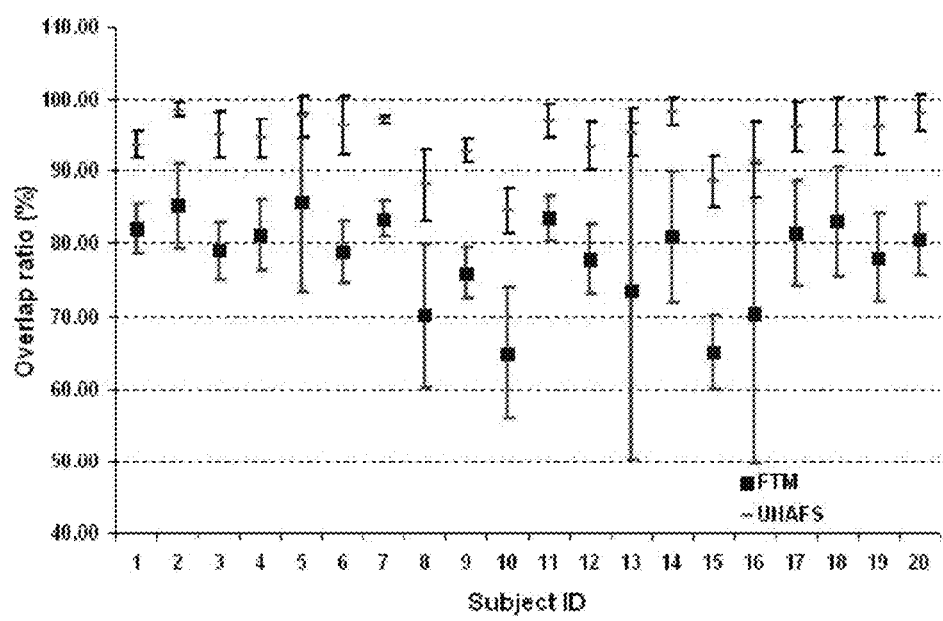
FIG. 49 depicts a comparison of the overlap ratios obtained by applying FTM and UHAFS to the data from 20 subjects, where the 95% confidence levels are shown.
Figure 50A:
FIGS. 50A-H depict a series of CT images: (A,E) Original CT images from subject-1 and subject-2, respectively; (B,F) Manually segmented images (white pixels denote fat tissue); (C,G) Segmentation results using FTM; and (D,H) Segmentation results using our method.
Figure 50B:
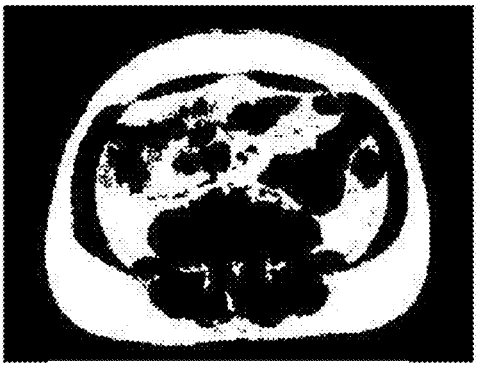
Figure 50C:
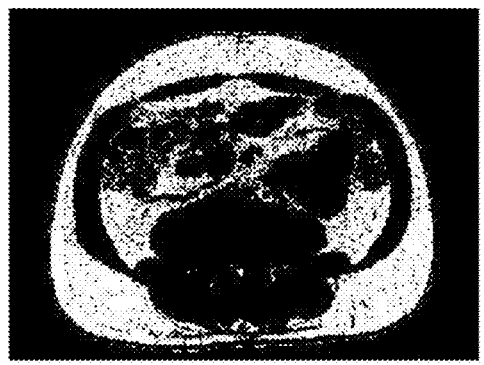
Figure 50D:
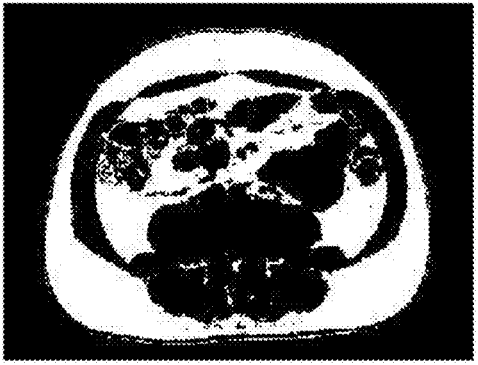
Figure 50E:
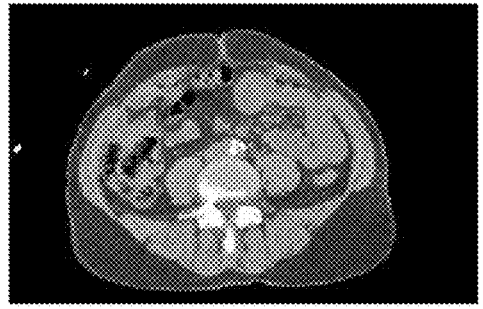
Figure 50F:
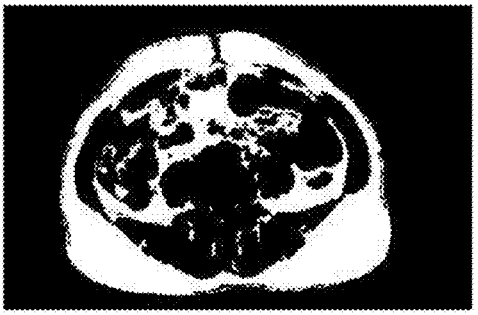
Figure 50G:
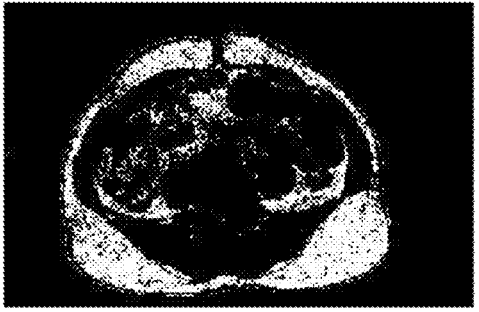
Figure 50H:
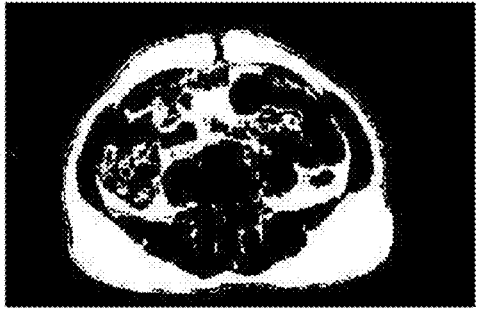
Figure 53A:
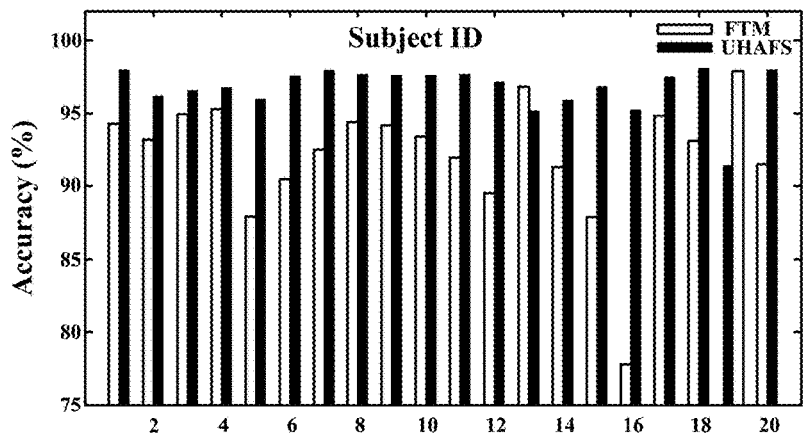
FIGS. 53A-C depict performance evaluation of UHAFS and FTM: (A) accuracy (%), (B) true positive rate (%), and (C) true negative rate (%)
Figure 53B:
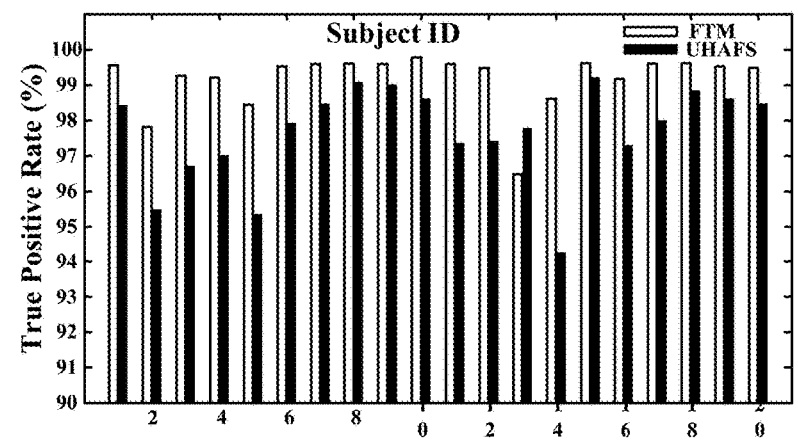
Figure 53C:
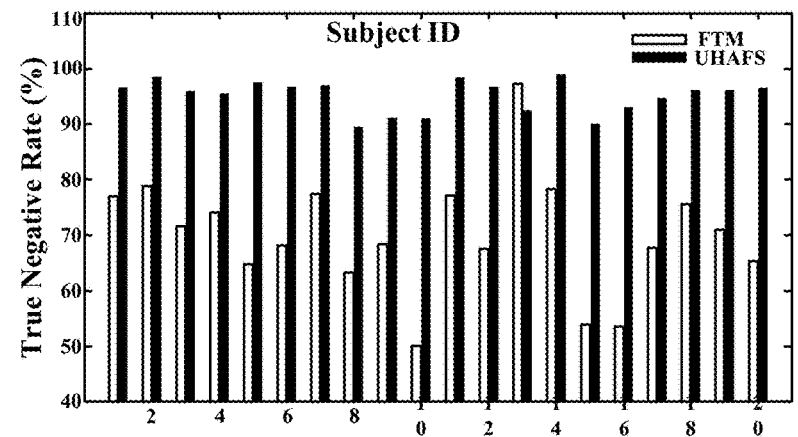
Figures 54A, 54B, 54C:
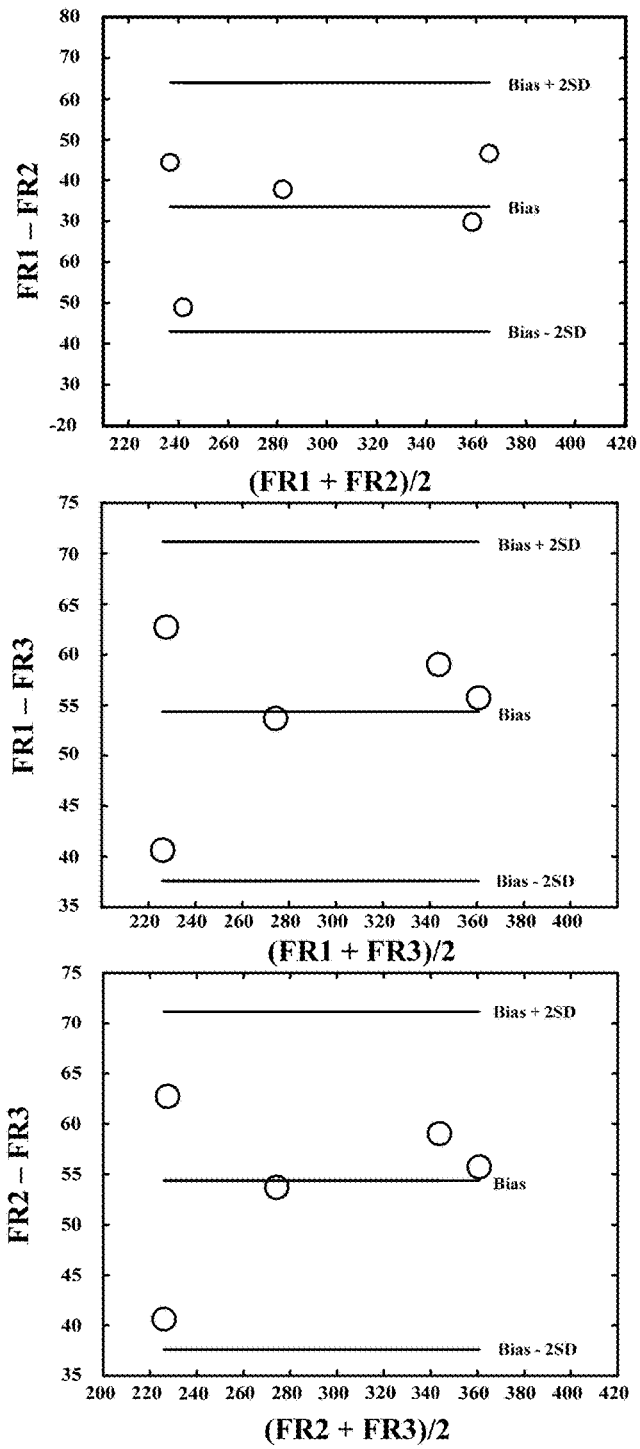
FIGS. 54A-C depict Bland-Altman analyses pertaining to the manual segmentation.
Figure 55A:
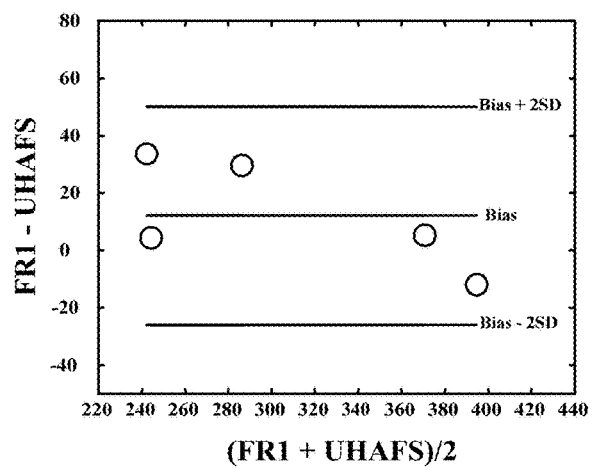
FIGS. 55A-C depict Bland-Altman analyses pertaining to the results obtained using UHAFS.
Figure 55B:
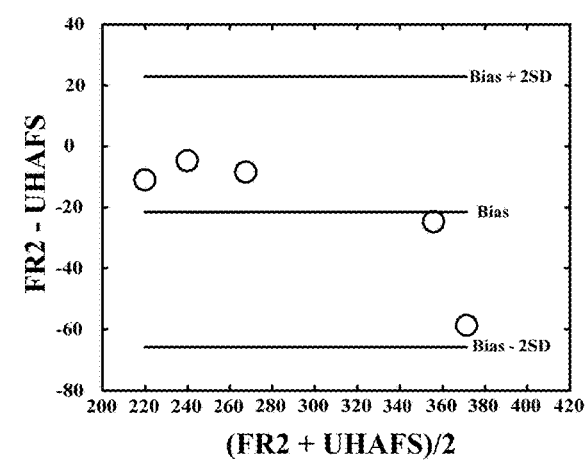
Figure 55C:
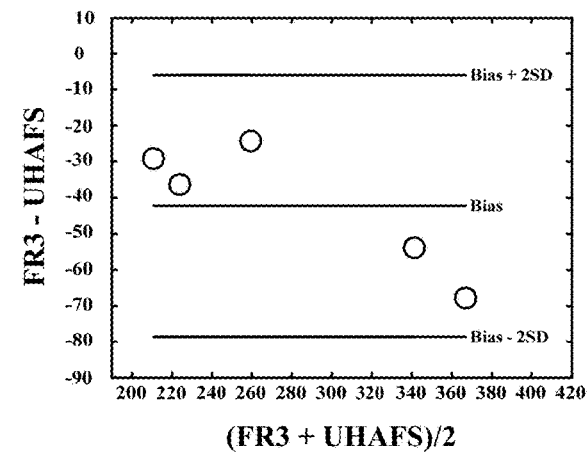
Figure 56A:
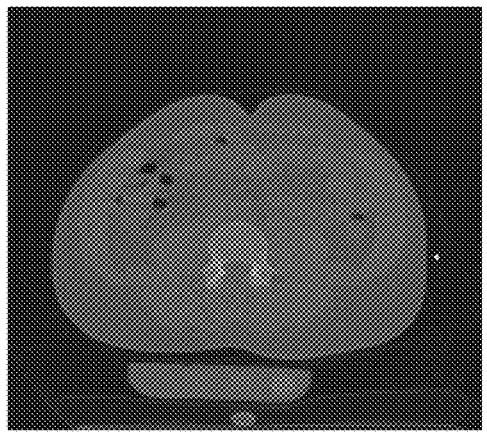
FIG. 56A-F depict a series of CT images: (A,D) Original CT images from Subject-1 and Subject-2, respectively; (B,E) Thresholded image after background removal; and (C,F) largest component of the thresholded image.
Figure 56B:
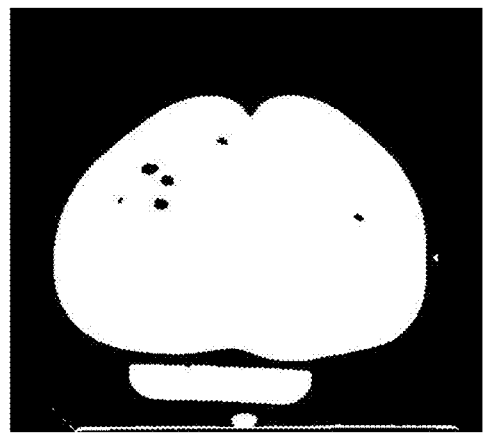
Figure 56C:
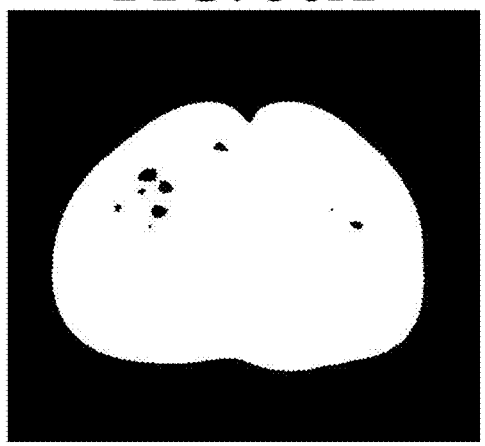
Figure 56D:
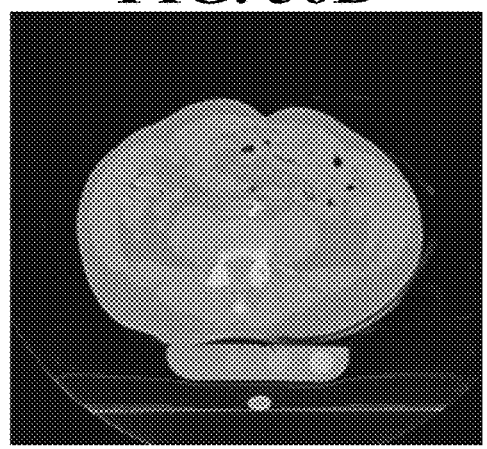
Figure 56E:
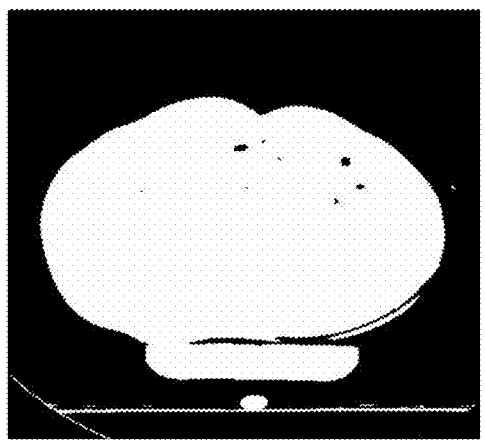
Figure 56F:
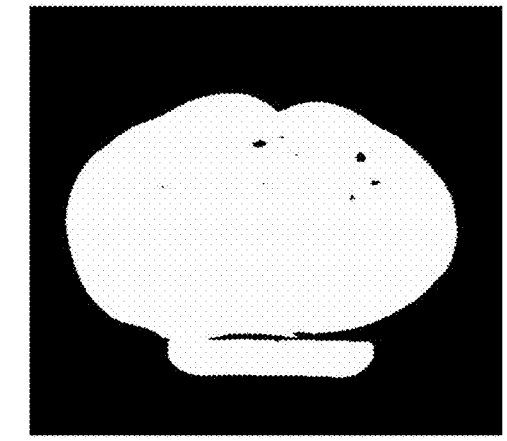

FIGS. 53A-C depicts the accuracy, the true positive rate, and the true negative rate obtained using FTM and UHAFS. Note that the true positive rates of the two methods are comparable, but UHAFS has a higher true negative rate and it is more accurate. FIG. 49 depicts the overlap ratio within the 95% confidence intervals obtained by applying the two algorithms 10 times in each image.

Figure 51A:
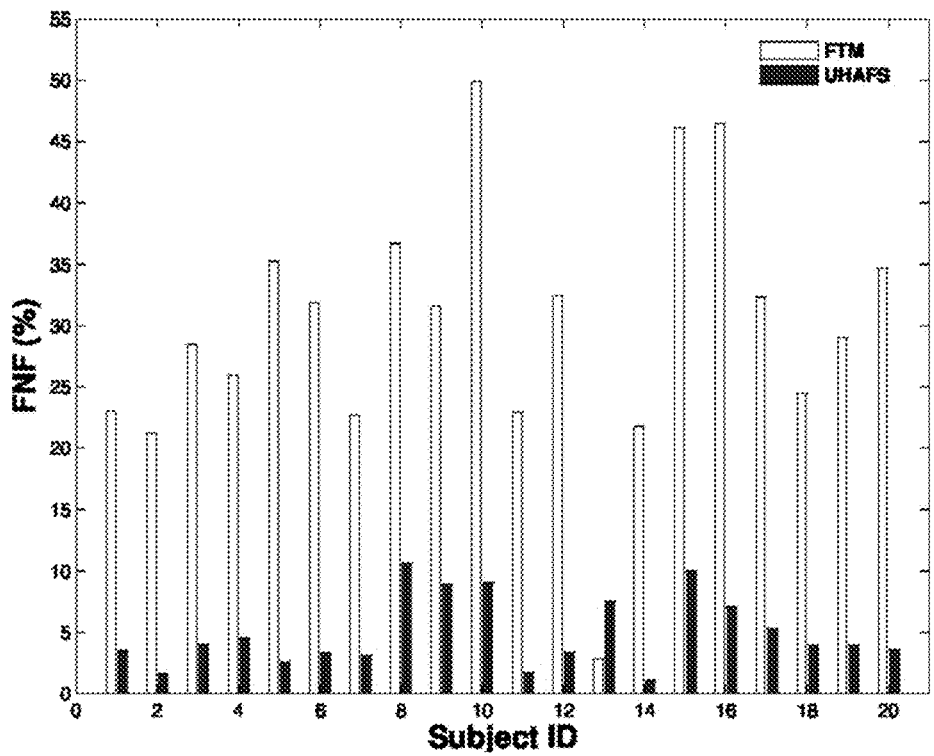
FIGS. 51A-B depict (A) False negative fraction and (B) false positive fraction for UHAFS and FTM.
Figure 51B:
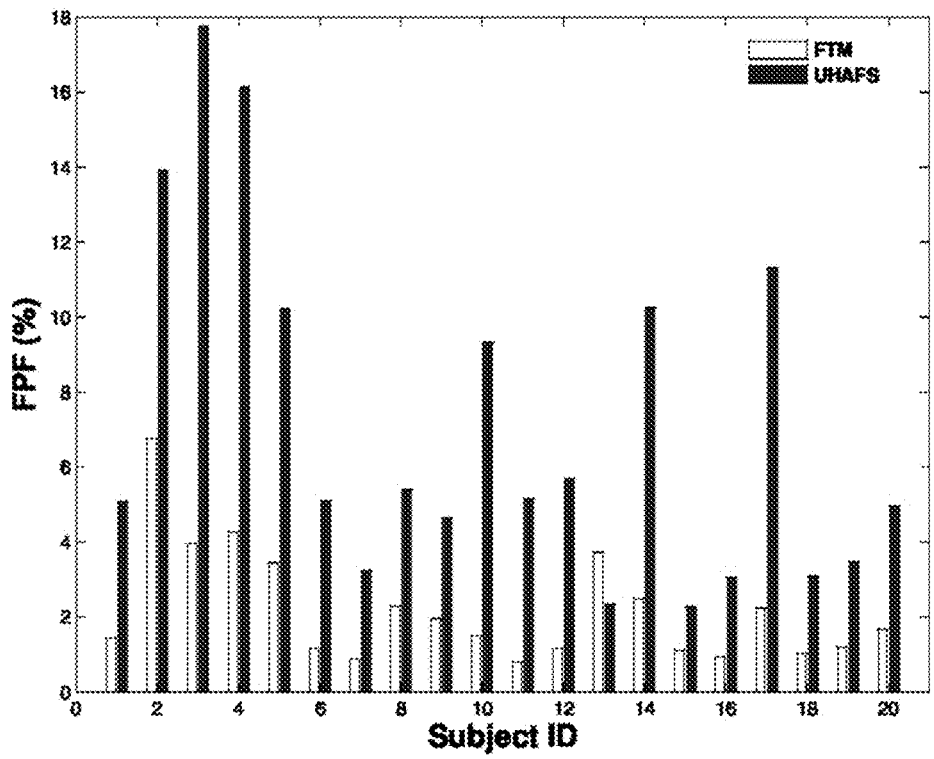
Figure 52A:
FIGS. 52A-L depict a series of CT images: (A,E,I) Original CT images from subject-3, subject-4, and subject-5, respectively; (B,F,J) Manually segmented images (white pixels denote fat tissue); (C,G,K) Segmentation results using FTM; and (D,H,L) Segmentation results using UHAFS.
Figure 52B:
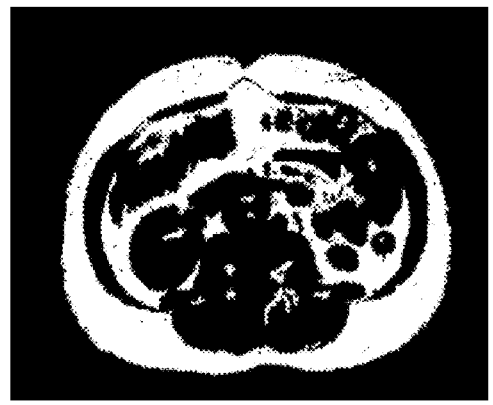
Figure 52C:
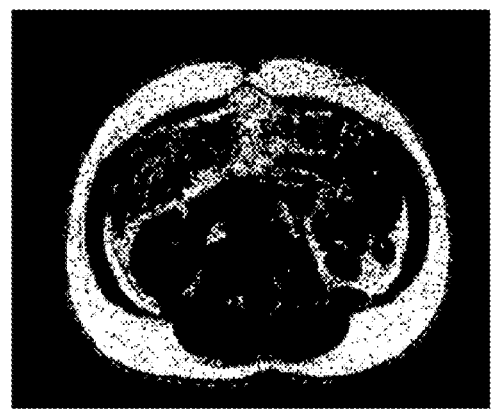
Figure 52D:
Figure 52E:
Figure 52F:
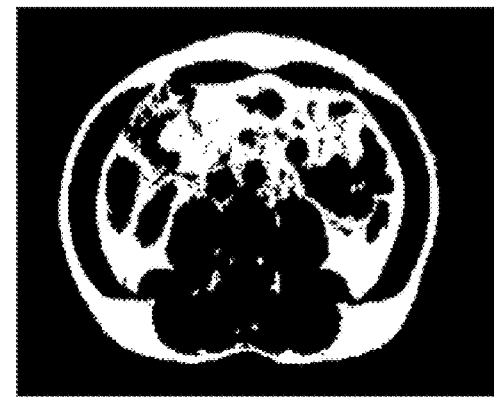
Figure 52G:
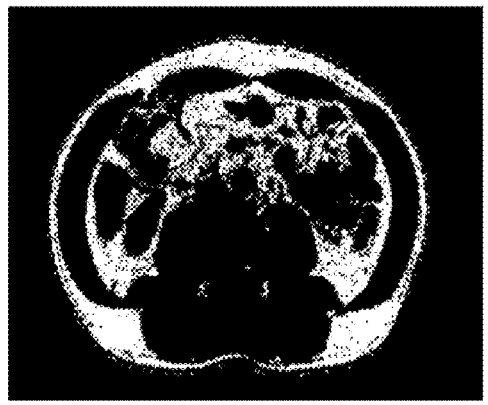
Figure 52H:
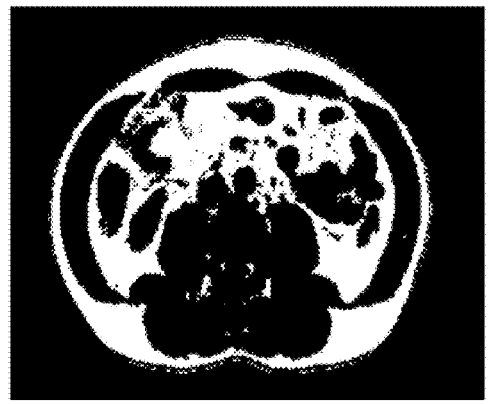
Figure 52I:
Figure 52J:
Figure 52K:
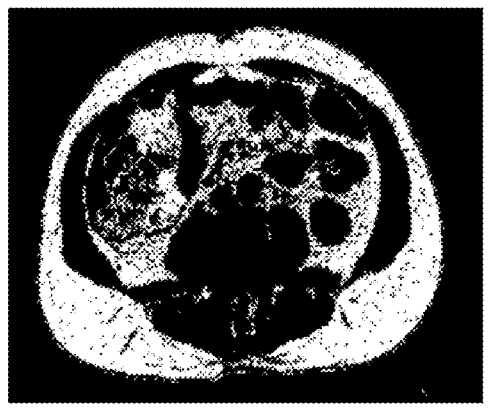
Figure 52L:
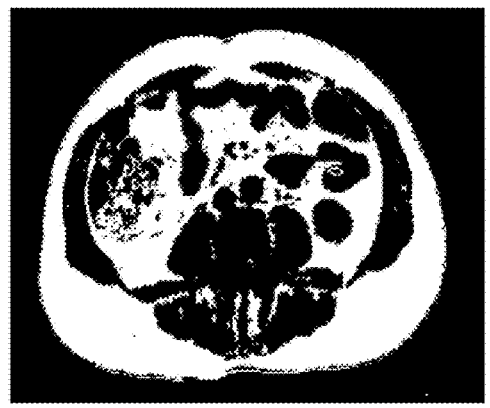

We define the false negative fraction (FNF) to indicate the fraction of tissue that is included in the ground truth but missed by the method: FNF=100*FN/(TP+FN). The false positive fraction (FPF) indicates the amount of tissue falsely identified by the method as a fraction of the total amount of tissue in the ground truth: FPF=100*FP/(TP+FN). FIGS. 51A-B reveals a significant decrease in the FNF and a slight increase in the FPF obtained by UHAFS as compared to FTM pointing to the reliability of our method.

The agreement between the expert manual segmentations and UHAFS for the fat area computation as well as the inter-observer variability were assessed according to the method described by Bland and Altman [1]. Let FR1 de-note the fat area labelled by the first reader, FR2 denote the fat area labeled by the second reader, and FR3 denote the fat area labelled by the third reader. The inter-observer and UHAFS mean biases and variabilities for the first reader, the second reader, and the third reader, for the fat area estimation are depicted in FIGS. 54A-C and FIGS. 55A-C. Finally, our method exhibits a considerable reduction in time as compared to manual tracing (from 5-10 mins to less than 10 seconds).

5. Conclusions

In this section, we have presented an automatic and robust segmentation method for quantifying abdominal fat in CT images across subjects and across scanners. We have also successfully applied our framework for automatic extraction of endocardial and epicardial contours of the left ventricle in cine bFFE MR images [7].

6. References

The following references were cited in the Automatic Segmentation of Abdominal Fat from CT Data section.

[1] J. M. Bland and D. G. Altman. Statistical methods for assessing agreement between two methods of clinical measurement. Lancet, 1:307-310, 1986.

[2] T. F. Cootes, C. J. Taylor, D. H. Cooper, and J. Graham. Active shape models their training and application. Computer Vision, Graphics and Image Processing, 61(1):38-59, January 1995.

[3] K. M. Flegal, M. D. Carroll, C. L. Ogden, and C. L. John-son. Prevalence and trends in obesity among US adults, 1999-2000. Journal of the American Medical Association, 288:1723-7, 2002.

[4] K. Laws. Texture Image Segmentation. PhD thesis, USC, 1980.

[5] B. S. Manjunath and W. Y. Ma. Texture features for browsing and retrieval of image data. IEEE Trans-actions on Pattern Analysis and Machine Intelligence, 18(8):837-842. August 1996.

[6] A. S. Pednekar, U. Kurkure, and I. A. Kakadiaris. Adaptive fuzzy connectedness-based medical image segmentation. In Proceedings of the Indian Conference on Computer Vision, Graphics, and Image Processing, pages 457-462, Ahmedabad, India, Dec. 16-18 2002.

[7] A. S. Pednekar, U. Kurkure, I. A. Kakadiaris, R. Muthupillai, and S. D. Flamm. Left ventricular segmentation in MR using hierarchical multi-class multi-feature fuzzy connectedness. In Proceedings of the 7th International Conference on Medical Image Computing and Computer-Assisted Intervention, pages 402-410, Saint-Malo, France, September 26-30 2004.

[8] A. Rangarajan, H. Chui, and F. L. Bookstein. The soft assign procrustes matching algorithm. In Proceedings of the 15th International Conference on Information Processing in Medical Imaging, pages 29-42, June 09-13 1997.

[9] P. K. Saha and J. K. Udupa. Relative fuzzy connectedness among multiple objects: theory, algorithms, and applications in image segmentation. Computer Vision and Image Understanding, 82:42-56, 2000.

[10] P. K. Saha and J. K. Udupa. Fuzzy connected object delineation: Axiomatic path strength definition and the case of multiple seeds. Computer Vision and Image Understanding, 83:275-295, 2001.

[11] P. K. Saha, J. K. Udupa, and D. Odhner. Scale-based fuzzy connected image segmentation: theory, algorithms, and validation. Computer Vision and Image Understanding, 77:145-174, April 2000.

[12] Y. Tohru, N. Tadashi, Y. Mitsukazu, H. Abdul, M. Masakazu. Y. Kouichi. A. Takeshi, K. Kazuaki, F. Tohru, Y. Shizuya, and M. Yuji. Abdominal fat: Standardized technique for measurement at CT. Radiology, 211:283-286, 1999.

[13] J. K. Udupa, Y. Jin, C. Imielinska, A. Laine, W. Shen, and S. B. Heymsfield. Segmentation and evaluation of adipose tissue from whole body mri scans. In Proceedings of the 6th International Conference on Medical Image Computing and Computer-Assisted Intervention, pages 635-642, Montreal, Canada, Nov. 15-18 2003.

[14] J. K. Udupa and S. Samarasekera. Fuzzy connectedness and object definition: theory, algorithms, and applications in image segmentation. Graphical Models and Image Processing, 58(3):246-261, May 1996.

Evaluation of Abdominal Fat Burden Quantification in CT

Abdominal fat accumulation is an important cardiovascular risk factor. In clinical practice, delineation of subcutaneous and visceral fat is performed manually by an expert. This procedure is labor intensive, time consuming, and subject to inter- and intra-observer variability. In this section, we present an extension of our previous work on automatic fat burden quantification and classification. Our improved method automatically differentiates abdominal fat into subcutaneous and visceral fat components and removes equipment-related artifacts. We evaluated the performance of our method using data from 40 subjects with very encouraging results.

I. Introduction

In modern medicine fat tissue is no longer viewed as a simple energy storehouse of the body; instead it is considered an active organ with critical metabolic and immune regulatory functions. Abdominal fat, both visceral and subcutaneous, has been shown as an important cardiovascular risk factor. Computed Tomography (CT) and Magnetic Resonance Imaging (MRI) are popular imaging modalities used to quantify abdominal fat distribution. However, CT is less expensive and provides better contrast between fat and non-fat tissues. In current clinical practice, fat burden is quantified by manually tracing a region of interest over the subcutaneous and abdominal fat regions by an expert. This is a very time consuming and cumbersome process subject to human error and variability. Thus, the development of a computer-assisted method which provides unbiased and consistent results automatically with minimal human intervention is highly desirable.

The normal CT attenuation range for fat tissues (in Hounsfield units (Hu)) is defined as the interval within ($-190<Hu<-30$) [6]. The average Hu for fat tissue varies across subjects and also depends on the CT scanner [6]. Consequently, assessment of fat distribution requires a case-specific flexible attenuation range. A recent technique called the flexible threshold method (FTM) [6] estimates the abdominal fat distribution based on a interactively defined attenuation range. First, a region of interest (ROI) of the subcutaneous fat layer is defined by manually tracing its contour on each scan, and the attenuation range for fat tissue is computed on the basis of mean attenuation plus or minus 2 standard deviation. Then, intraperitoneal tissue was defined by manually tracing its contour on the scan; within that ROI, all pixels in the computed attenuation range are classified to be visceral fat. This method is independent of the relative spatial location of the pixel with its neighborhood pixels. As a result, segmentation using solely an intensity-based threshold is not very accurate. The presence of equipment-related artifacts adds a new dimension of difficulty.

In our previous work [9], we have developed a framework for automatic segmentation and quantification of abdominal fat in CT. In this section, we present an extension of this work (AFACT: Automatic Fat Analysis in Computed Tomography) which incorporates: 1) automatic differentiation of abdominal fat into subcutaneous and visceral, and 2) automatic removal of equipment-related artifacts.

The rest of the section is organized as follows. In Section II, we review and outline the extensions to our previous work. In Section III, we present results from our method and a comparison with previous methods, while in Section IV we present our conclusions.

II. Materials and Methods

Our work is based on a hierarchical, multi-class, multi-feature, fuzzy affinity-based framework [9], which combines the intensity and texture information with local "hanging togetherness" within a fat class. The fuzzy connectedness constraint for the object extraction presented in [4], [5], [8] is relaxed to allow global segmentation. Thus, instead of applying a space-invariant global threshold value, our computational framework adapts the threshold value locally to account for the local "hanging togetherness" of the tissue to be segmented. The Mahalanobis metric is used to compute the similarity of pixels in the intensity- and texture-based feature space. The most discriminating combination of texture features for specific object regions (fat, nonfat, and background classes) is determined in the training phase of our framework.

A. Experimental Data

The study population consists of 40 subjects. The data were obtained by a CT abdominal scan between the fourth and fifth lumbar vertebrae (L4-L5) (i.e., at the level of umbilicus) with 5 CT scan images per patient. Slice thickness was 6.0 mm in all subjects, scanning was performed at 130 kV and 200 mA, and the field of view ranged from 30 to 50 cm.

B. AFACT Methodology Overview

The AFACT methodology is set forth below in outline format.

I. Training Phase
  A. Estimate object-specific (fat, non-fat, background classes) distributions using a training data set.
    Step 1: Compute relevant intensity and texture features.
    Step 2: Compute the most discriminant features.
  B. Construct a template using training data set. Step 3: Construct a subcutaneous fat template using the Active Shape Model (ASM) framework [1].
II. Deployment Phase
  C. Remove artifacts and initialize the target object seed region.
    Step 4: Remove equipment-related artifacts.
    Step 5: Initialize the seed point automatically using the subcutaneous fat template.
  D. Compute the fuzzy affinity-based object.
    Step 6: Compute the most discriminating features selected from Step 2 of training.
    Step 7: Compute the global object affinity using the Mahalanobis metric.
    Step 8: Compute the fat by thresholding the global object affinity image.

In this work, we have added Step 4 to our previous work for automatic equipment related artifact removal and have made modifications in Step 3 and Step 5 to report subcutaneous and visceral fat automatically.

C. AFACT Algorithm Description

1) Steps 1-3, Training Phase: Initially, Laws' features [2] and Gabor's texture features [3] for the abdominal CT images were computed. The most discriminating feature combinations were determined according to their cumulative discriminating power. Our feature vector consisted of two features, namely intensity and Laws' ss feature. Also, we constructed an ASM by manually selecting landmark points around the subcutaneous and visceral fat region. Landmark points are selected based on the curvature of the boundary of the fat region.

2) Step 4, Automatic removal of equipment-related artifacts: Many artifacts in the CT image (e.g., the patient table and wires) have intensity distributions very similar to that of the fat tissue. To correctly quantify the fat burden, it is important that such artifacts are removed from the image. We have added an artifact removal step in our method that automatically removes such artifacts. First, the background is automatically removed using Otsu's thresholding method. Largest component analysis is then performed on the resulting image. FIGS. 56A-F depicts the various steps of the automatic table removal for Subject-1 and Subject-2. Note that in the case of Subject-2, the table is not successfully removed by the largest component analysis. A geometric approach is then employed to successfully remove the table artifacts. Specifically, the bounding box of the largest component is first detected. Then, a ROI is created around the lowest part of the largest component with height of the bounding box defined by the maximum table height parameter. In this ROI, the left- and right-most contour profiles are analyzed. Clear maxima in the contour curvature profiles appear at the start of the table on both sides. The table is then automatically removed using this information.

Figure 57A:
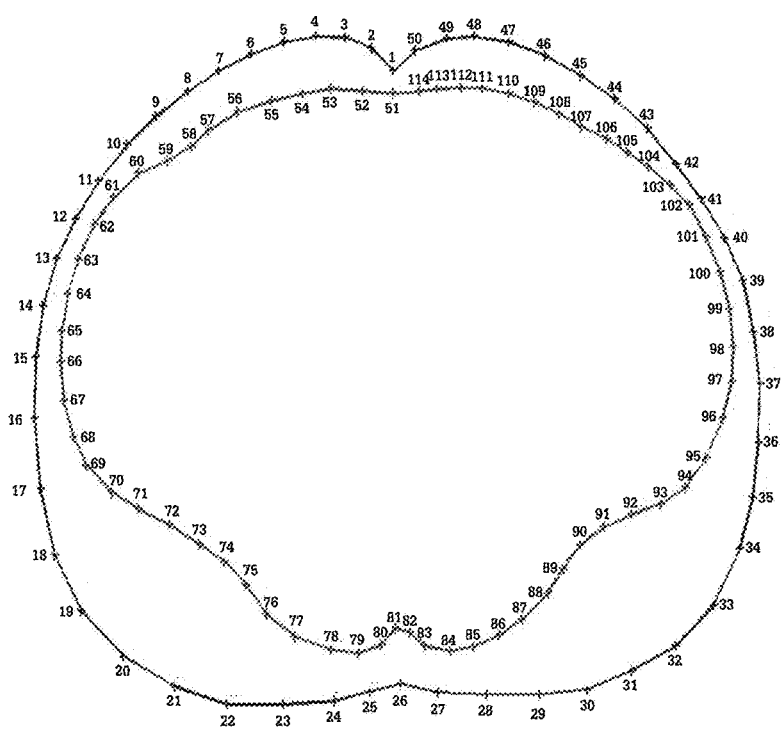
FIG. 57A-B depict ASM fitting of the subcutaneous fat template: (A) Mean shape of the subcutaneous fat template, and (B) initial fit.
Figure 57B:
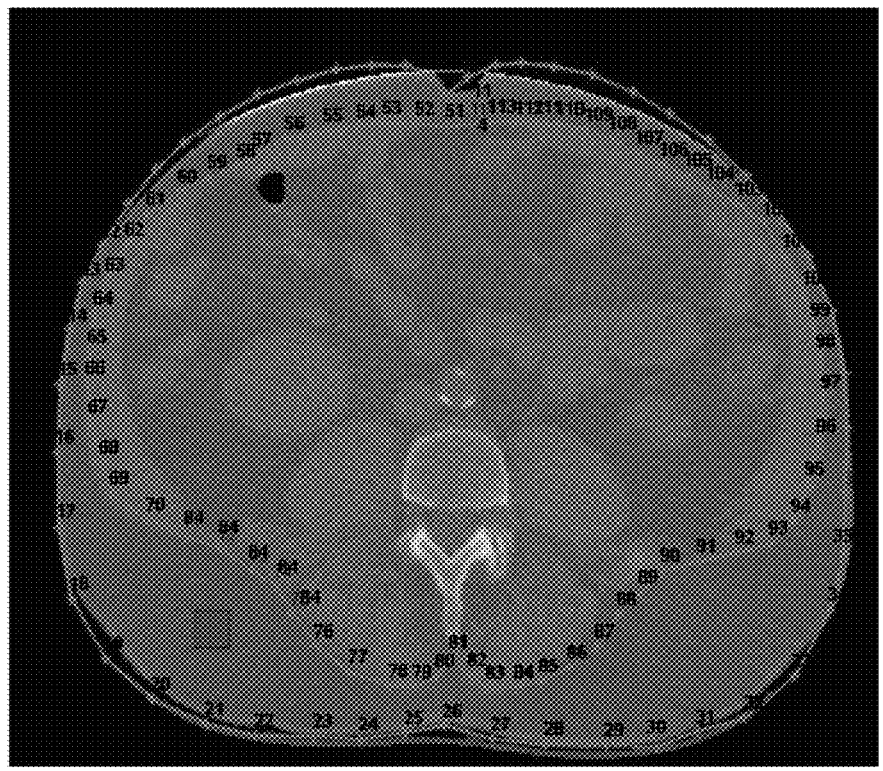
Figure 58A:
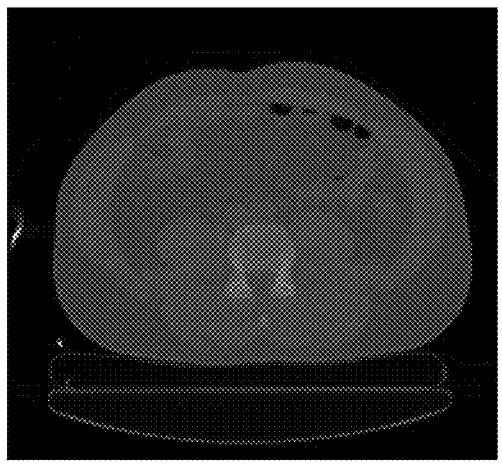
FIGS. 58A-H depict steps of the segmentation process: (A) original image, (B) automatic seed initialization using ASM fitting, (C) body mask after table removal, (D) visceral fat mask, (E) subcutaneous fat mask, (F) estimated visceral fat, (G) estimated subcutaneous fat, and (H) estimated total abdominal fat.
Figure 58B:
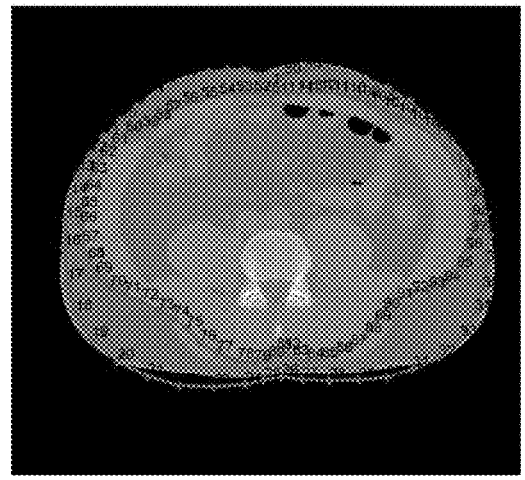
Figure 58C:
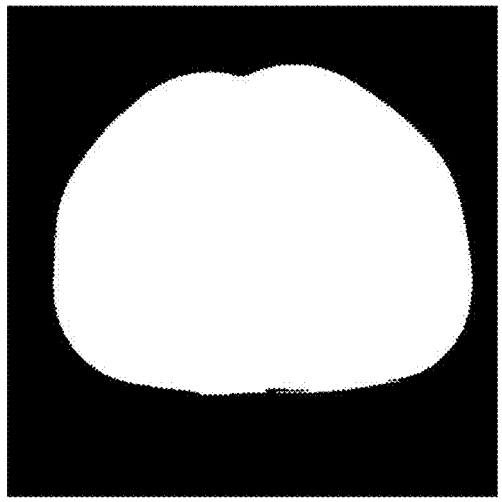
Figure 58D:
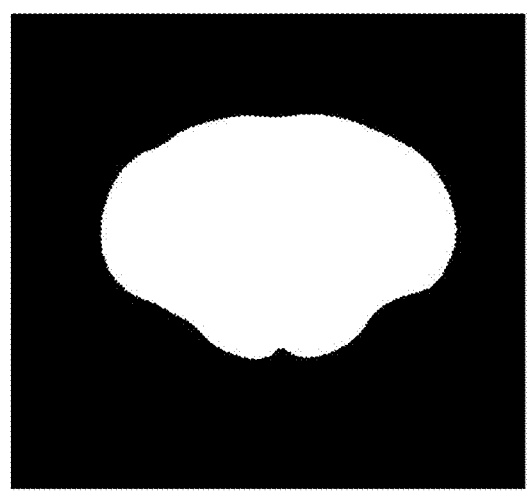
Figure 58E:
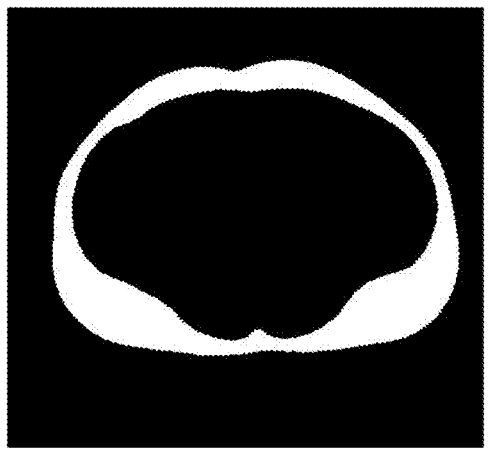
Figure 58F:
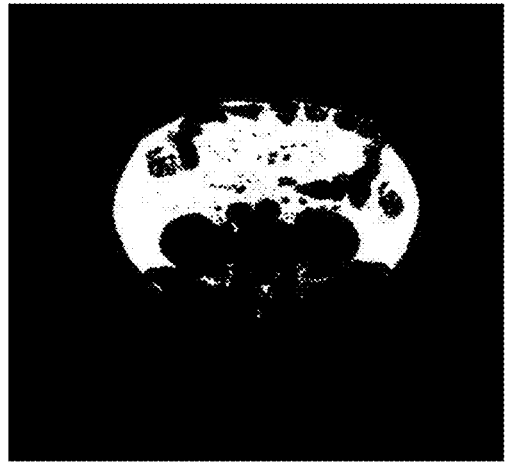
Figure 58G:
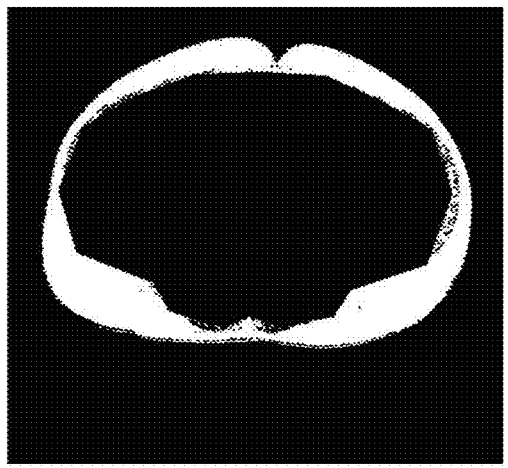
Figure 58H:
Figure 59A:
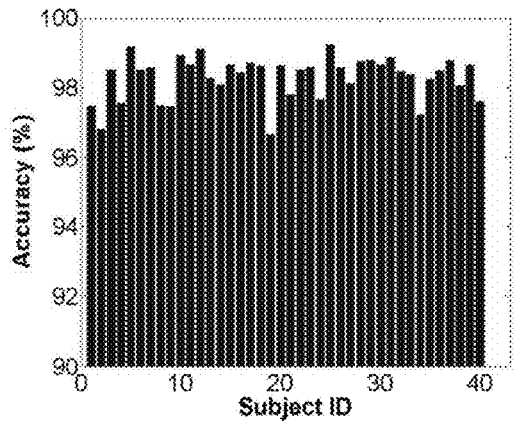
FIGS. 59A-F depict performance evaluation of AFACT for subcutaneous and visceral fat respectively: (A,B) accuracy, (C,D) true positive rate, and (E,F) true negative rate.
Figure 59B:
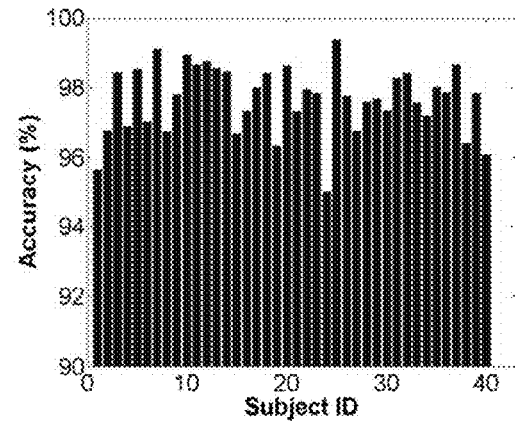
Figure 59C:
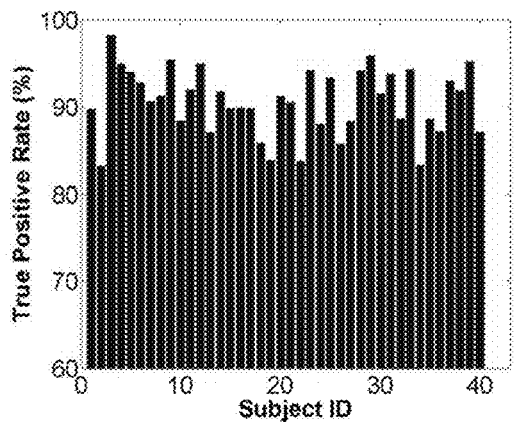
Figure 59D:
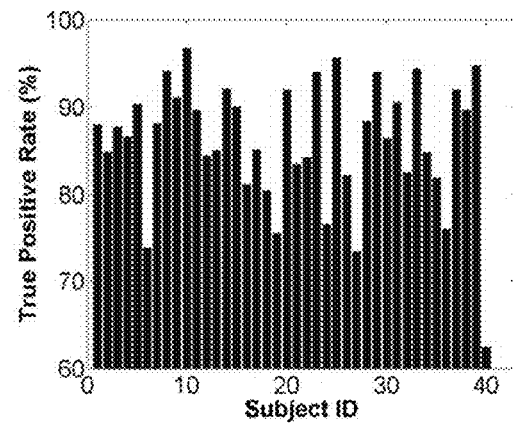
Figure 59E:
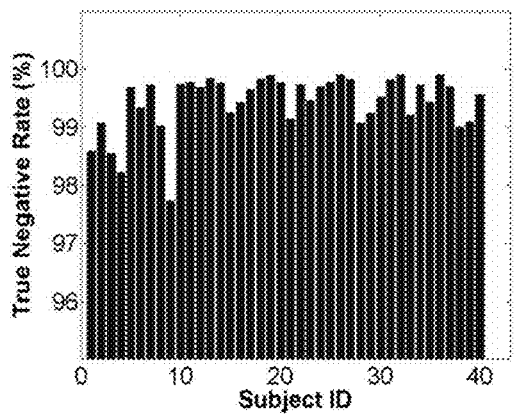
Figure 59F:
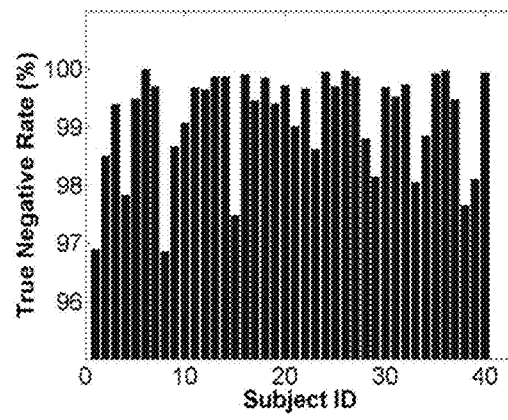

3) Step 5, Automatic seed initialization: During the deployment phase of our framework, we estimate the statistics of fat tissue by using a sample region around a seed point, hence the selection of the seed point is very critical. We obviated the need for manual seed selection by automatic seed initialization using ASM. We created a subcutaneous fat template by selecting 114 landmark points based on the anatomy of the abdominal region. To increase our accuracy to report subcutaneous and visceral fat automatically, we have added additional landmark points to the earlier template. FIG. 57A depicts the mean shape of the subcutaneous fat template. The seed region is selected by fitting the subcutaneous fat template to the CT image. Specifically, the seed point is chosen as the centroid of the region enclosed by landmarks 19, 22, 72, and 76. FIG. 57B depicts the seed point and the location of the 114 landmarks after ASM fitting.

4) Step 6-8, Segmentation of fat areas: First, the most discriminant features selected from Step 2 of training are computed for the current image. Then, the global object affinity is computed using the Mahalanobis metric. The global affinity image has values between 0 and 1; the higher the value, the higher the probability that the tissue belongs to the fat region. The fat areas are obtained by thresholding the global object affinity image. FIGS. 58A-H depict the steps of automatic fat segmentation.

III. Results and Discussion

We have compared the results of our method (AFACT) to expert manual segmentation of subcutaneous and visceral fat for 40 subjects. The manual delineation of the fat region in the CT images, performed by experienced physicians/radiologists was used as gold standard. We evaluated the results of our algorithm by computing the three measures of accuracy recommended by Udupa, et al. [7]. Specifically, we computed the false negatives (FN), false positives (FP), true negatives (TN), and true positives (TP) by computing the number of pixels that were classified as the background and the ROI, both correctly and incorrectly.

FIGS. 59A-F depict the accuracy, the true positive rate, and the true negative rate obtained by AFACT for subcutaneous (FIGS. 59A, 59C, 59E) and visceral fat (FIGS. 59B, 59D, 59F) quantification when compared with manual segmentation. The mean accuracy for subcutaneous and visceral fat was 98.29%±0.62% and 97.660% 0.98%, respectively. The mean true negative rate was 99.43%±0.49% and 99.14%±0.89%, respectively. Finally, the mean true positive rate was found to be 90.01%±3.77% and 86.14%±7.25%, respectively.

FIG. 60 depicts the accuracy, the true positive rate, and the true negative rate obtained using FTM and AFACT for the quantification of total fat. The mean accuracy for the 40 subjects using AFACT was 96.41%±1.24%, compared to FTM's mean accuracy of 94.93%±2.02%. The mean true negative rate using AFACT was 98.63%±1.36%, compared to FTM's mean accuracy of 99.24%±0.51%. The mean true positive rate for total fat using AFACT was 89.56%±4.55%, compared to FTM's mean accuracy of 81.44%±7.25%.

Figure 60A:
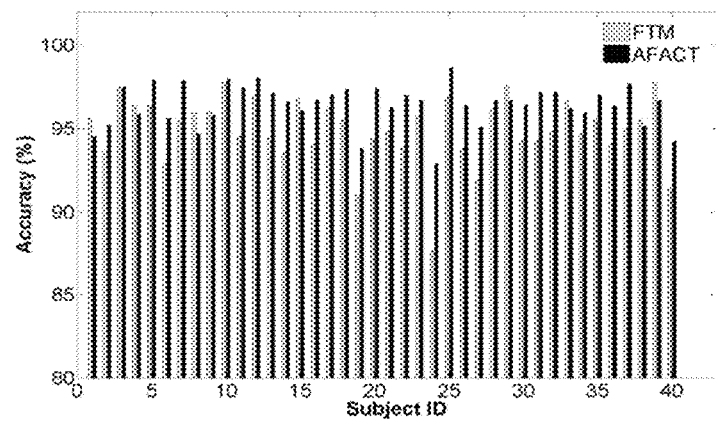
FIGS. 60A-C depict performance evaluation of AFACT for total fat segmentation: (A) accuracy, (B) true positive rate, and (C) true negative rate.
Figure 60B:
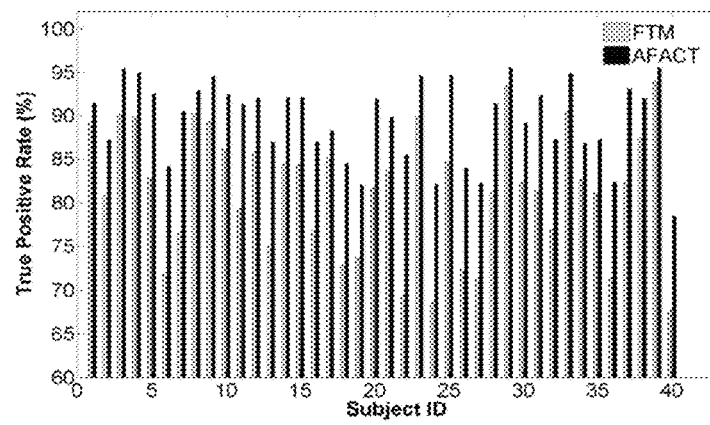
Figure 60C:
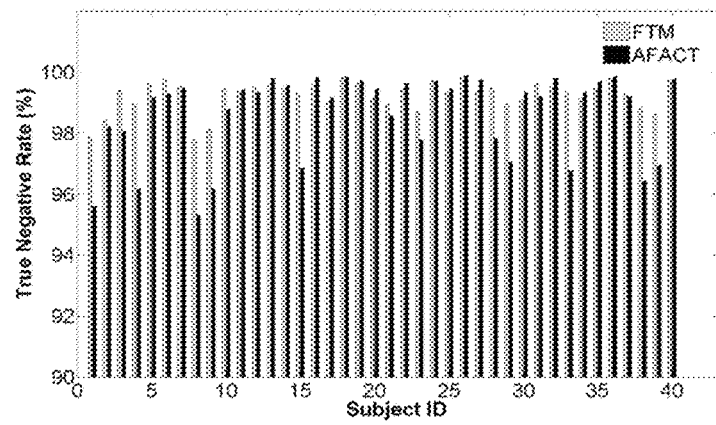
Figure 61E:
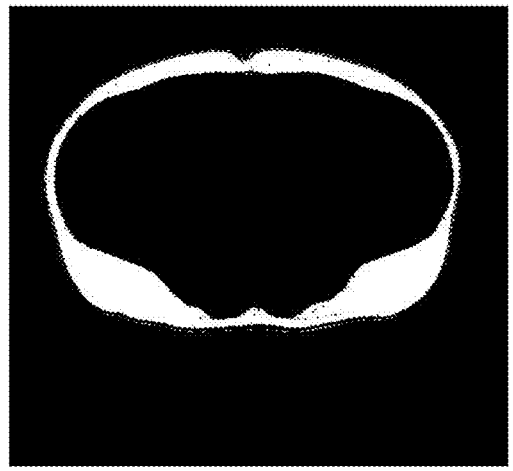
Figure 61F:
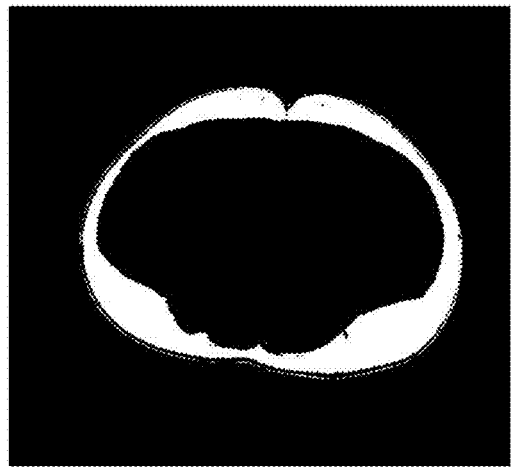
Figure 61G:
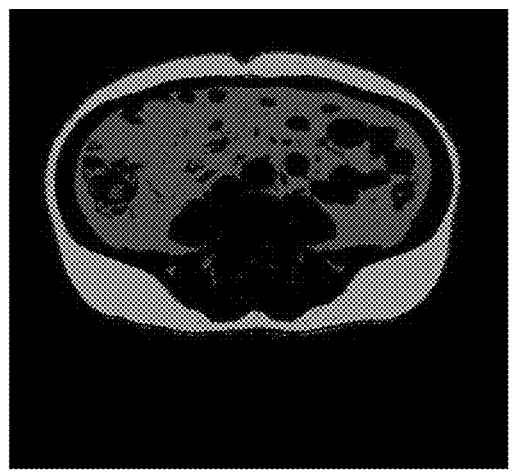
Figure 61H:
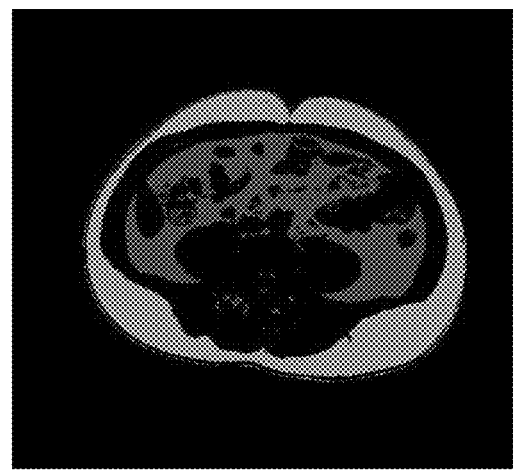

The qualitative results of our algorithm for Subjects 1 and 2 are depicted in FIGS. 61A-H. Although in total fat quantification the true negative rates of the two methods are comparable, AFACT achieves a higher true positive rate and a higher accuracy as depicted in FIGS. 60A-C.

IV. Conclusions

In this section, we have presented an extension of our previous work on abdominal fat quantification. We have successfully quantified and classified the visceral and subcutaneous fat burden in abdominal CT images and performed extensive evaluation against manual segmentations performed by experts. Our method for total fat quantification exhibits a comparable true negative rate and higher true positive rate and accuracy than the FTM method. It also achieves a comparable true negative rate and accuracy against manual delineations of subcutaneous and visceral fat. However, it is fully automatic and does not require any kind of seed initialization, in contrast to other existing methods. In addition, it exhibits a considerable reduction in time as compared to manual tracing (from 5-10 mins to less than a minute) and it could therefore be used at reading centers for clinical studies in order to minimize reading time.

REFERENCES

The following references were cited in the Evaluation of Abdominal Fat Burden Quantification in CT section.

[1] T. F. Cootes, C. J. Taylor, D. H. Cooper, and J. Graham. Active shape models—their training and application. Computer Vision, Graphics and Image Processing, 61(1): 38-59, January 1995.

[2] K. Laws. Texture Image Segmentation. PhD thesis, USC, 1980.

[3] B. S. Manjunath and W. Y. Ma. Texture features for browsing and retrieval of image data. IEEE Transactions on Pattern Analysis and Machine Intelligence, 18(8):837-842, August 1996.

[4] A. S. Pednekar and I. A. Kakadiaris. Image Segmentation based on fuzzy connectedness using dynamic weights. IEEE Transactions in Image Processing, 2005 (In Press).

[5] A. S. Pednekar, U. Kurkure, I. A. Kakadiaris. R. Muthupillai, and S. D. Flamm. Left ventricular segmentation in MR using hierarchical multi-class multi-feature fuzzy connectedness. Proc. 7th International Conference on Medical Image Computing and Computer-Assisted Intervention, pages 402-410, Saint-Malo, France, September 26-30 2004.

[6] Y. Tohru. N. Tadashi, Y. Mitsukazu, H. Abdul, M. Masakazu, Y. Kouichi, A. Takeshi, K. Kazuaki, F. Tohru, Y. Shizuya, and M. Yuji. Abdominal fat: Standardized technique for measurement at CT. Radiology, 211:283-286, 1999.

[7] J. K. Udupa, Y. Jin, C. Imielinska, A. Laine, W. Shen, and S. B. Heymsfield. Segmentation and evaluation of adipose tissue from whole body MRI scans. Proc. 6th International Conference on Medical Image Computing and Computer-Assisted Intervention, pages 635-642, Montreal, Canada, Nov. 15-18 2003.

[8] J. K. Udupa and S. Samarasekera. Fuzzy connectedness and object definition: theory, algorithms, and applications in image segmentation. Graphical Models and Image Processing, 58(3):246-261, May 1996.

[9] A. Pednekar, A. N. Bandekar, I. A. Kakadiaris, and M. Naghavi. Automatic segmentation of abdominal fat in CT. In Proc. IEEE Workshop on Applications of Computer Vision, pages 308-315, Colorado, Jan. 5-7, 2005.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for motion compensation comprising the steps of:

constructing a heart coordinate system derived from electron beam computerized tomography (EBCT) data and/or magnetic resonance imaging (MRI) data, wherein the heart coordinate system comprises an origin c corresponding to a center or a base of a heart of a patient, a $z_h$ axis pointing from the origin c towards an apex of the heart, a $y_h$ axis pointing from the origin c towards a right coronary artery, and a $x_h$ axis pointing from the origin c towards a left circumflex artery, capturing a set of locations of a left anterior descending coronary artery (LAD) from a set of EBCT slices through the patient's heart including the LAD, computing a parametric curved spine l(u) comprising a $9^{th}$ order polynomial capturing a global shape of a medial axis of the (LAD), constructing a local coordinate system associated with the spine l(u), wherein the local coordinate system comprises a tangent vector function T(u), a binormal vector function B(u) and a normal function N(u), wherein:

$$T(u) = \frac{\dot{l}(u)}{|\dot{l}(u)|},$$

$$B(u) = \frac{\dot{l}(u) \times \ddot{l}(u)}{|\dot{l}(u) \times \ddot{l}(u)|}, \text{ and}$$

$$N(u) = B(u) \times T(u),$$

computing changes in the parametric curved spine during N cardiac phases, wherein N is a number, constructing a tube-shaped deformable representation of the LAD, wherein a circle is determined at each of the locations along the spine curve l(u) to form the tube-shaped deformable representation, determining translation and orientation parameters $q_c$ and $q_R$;

estimating global reference shape parameters $q_e$, estimating a motion parameters $q_{T_i}$ and determining whether an LAD of a patient's heart corresponds to a vascular disease based on the tube-shaped deformable representation and the parameters $q_c$, $q_R$, $q_e$, and $q_{T_i}$.

2. The method of claim 1, wherein a number of the locations is between 25 and 35.

3. The method of claim 1, wherein a number of point on each circle is determine from 32 to 64 sample in the u parameter and 32 to 120 samples if the v parameter.

4. The method of claim 1, wherein N phases are the phases between ES to ED or ED to ES.

5. The method of claim 1, wherein the representation is a Frenet-Serret representation.

6. The method of claim 1, wherein the representation deforms during the cardiac phases and the deformations may be used to indicate diseases of the heart.

* * * * *